US009657435B2

(12) United States Patent
Frey et al.

(10) Patent No.: US 9,657,435 B2
(45) Date of Patent: May 23, 2017

(54) METAL FREE BLEACHING COMPOSITION

(75) Inventors: Markus Frey, Rheinfelden (CH); Hauke Rohwer, Lorrach (DE); Frederique Wendeborn, Ranspach-le-Haut (FR); Menno Hazenkamp, Riehen (CH)

(73) Assignee: BASF SE, Ludwigshafen (DE)

( * ) Notice: Subject to any disclaimer, the term of this patent is extended or adjusted under 35 U.S.C. 154(b) by 207 days.

(21) Appl. No.: 13/703,385

(22) PCT Filed: Jun. 21, 2011

(86) PCT No.: PCT/EP2011/060367
§ 371 (c)(1),
(2), (4) Date: Jan. 30, 2013

(87) PCT Pub. No.: WO2012/000846
PCT Pub. Date: Jan. 5, 2012

(65) Prior Publication Data
US 2013/0117941 A1  May 16, 2013

Related U.S. Application Data

(60) Provisional application No. 61/358,965, filed on Jun. 28, 2010.

(30) Foreign Application Priority Data

Jun. 28, 2010 (EP) ..................... 10167513

(51) Int. Cl.
*C11D 3/39* (2006.01)
*C11D 3/395* (2006.01)
*C11D 7/54* (2006.01)
*D06L 3/02* (2006.01)
*C07C 225/06* (2006.01)
*C07C 225/22* (2006.01)
*C07C 317/32* (2006.01)
*C07C 323/32* (2006.01)
*C07C 381/12* (2006.01)
*C11D 3/30* (2006.01)
*C11D 3/34* (2006.01)
*C11D 7/32* (2006.01)
*C11D 7/34* (2006.01)

(52) U.S. Cl.
CPC ............ *D06L 3/021* (2013.01); *C07C 225/06* (2013.01); *C07C 225/22* (2013.01); *C07C 317/32* (2013.01); *C07C 323/32* (2013.01); *C07C 381/12* (2013.01); *C11D 3/30* (2013.01); *C11D 3/349* (2013.01); *C11D 3/3902* (2013.01); *C11D 3/3905* (2013.01); *C11D 3/3917* (2013.01); *C11D 7/3236* (2013.01); *C11D 7/3281* (2013.01); *C11D 7/34* (2013.01); *C07C 2101/14* (2013.01); *C11D 3/3915* (2013.01)

(58) Field of Classification Search
CPC .... C11D 3/28; C11D 3/30; C11D 3/34; C11D 3/3427; C11D 3/3902; C11D 3/3905; C11D 3/3915; C11D 3/3917; C11D 3/392; C11D 3/3942; C11D 3/3947; D06L 3/021; D06L 3/023; B08B 3/04
USPC ....... 510/220, 309, 311, 312, 313, 370, 375, 510/376, 499, 500; 8/111, 137; 134/25.2
See application file for complete search history.

(56) References Cited

U.S. PATENT DOCUMENTS

| | | | |
|---|---|---|---|
| 3,082,255 A | 3/1963 | Stevens et al. | |
| 4,318,791 A | 3/1982 | Felder et al. | |
| 4,582,862 A | 4/1986 | Berner et al. | |
| 4,992,547 A | 2/1991 | Berner et al. | |
| 5,049,481 A | 9/1991 | Okamoto et al. | |
| 5,919,745 A * | 7/1999 | Cala et al. | 510/340 |
| 6,022,906 A | 2/2000 | Ohwa et al. | |
| 6,034,045 A * | 3/2000 | Carr et al. | 510/361 |
| 6,277,808 B1 * | 8/2001 | Tcheou et al. | 510/417 |
| 6,303,563 B1 * | 10/2001 | De Buzzaccarini et al. | 510/504 |
| 7,125,832 B2 * | 10/2006 | Busch et al. | 510/305 |

(Continued)

FOREIGN PATENT DOCUMENTS

| | | |
|---|---|---|
| CN | 1634865 A | 7/2005 |
| FR | 2626880 | 8/1989 |
| GB | 2320027 A | 6/1998 |
| JP | S5499185 | 8/1979 |
| JP | S58157805 | 9/1983 |

(Continued)

OTHER PUBLICATIONS

"Photoinitiators for UV Curing—Key Products Selection Guide", Ciba Specialty Chemicals, p. 1-8, Oct. 2003.*

(Continued)

*Primary Examiner* — Gregory R Delcotto
(74) *Attorney, Agent, or Firm* — Marshall, Gerstein & Borun LLP

(57) ABSTRACT

The present invention relates to the use of a composition comprising specific a-amino-ketones, $H_2O_2$, a $H_2O_2$ precursor or a peracid and optionally an activator as a bleaching mixture for textile materials or dishes either manually or in an automatic washing machine or dish washer. Further aspects of the invention are the composition comprising specific a-aminoketones and $H_2O_2$, a $H_2O_2$ precursor or a peracid and a process for bleaching of stains or of soiling on textile materials or dishes in the context of a washing process either manually or in an automatic washing machine or dish washer. Also aspects of the invention are detergent formulations comprising such a composition and novel compounds.

7 Claims, No Drawings

(56) References Cited

U.S. PATENT DOCUMENTS

| | | |
|---|---|---|
| 7,928,049 B2 | 4/2011 | Wagner et al. |
| 2005/0176612 A1* | 8/2005 | Batchelor et al. ............ 510/302 |
| 2009/0289221 A1 | 11/2009 | Reinhardt et al. |
| 2009/0325840 A1 | 12/2009 | Preuschen |
| 2010/0184996 A1 | 7/2010 | Perboni et al. |
| 2012/0142793 A1 | 6/2012 | Frey et al. |
| 2012/0178844 A1 | 7/2012 | Frey et al. |

FOREIGN PATENT DOCUMENTS

| | | |
|---|---|---|
| JP | S6084248 | 5/1985 |
| JP | H02179643 | 7/1990 |
| JP | 2003505578 | 2/2003 |
| WO | 0107549 | 2/2001 |
| WO | 02/36723 A1 | 5/2002 |
| WO | WO02/36729 * | 5/2002 |
| WO | 2007/087259 A2 | 8/2007 |
| WO | 2008/014965 A1 | 2/2008 |
| WO | 2008/015443 A1 | 2/2008 |
| WO | 2008/155334 A2 | 12/2008 |
| WO | 2009/013163 | 1/2009 |
| WO | 2012/080088 A1 | 6/2012 |

OTHER PUBLICATIONS

Carroll et al., Journal of Medicinal Chemistry, American Chem. Soc. vol. 53, No. 5, Mar. 11, 2010 pp. 2204-2214.
Koehler et al., Royal Society of Chemistry, vol. 89, Jan. 1, 1991, pp. 163-181.
Kalendra et al., Journal of Organic Chemistry, vol. 2003, No. 68, Jan. 23, 2003 pp. 1594-1596.
Anonymous: "alpha-Aminoketone" ROMPP Online, Ver. 3.9, Dec. 31, 2007 pp. 1-2.
Anonymous: "Kat" ROMPP Online, Ver. 3.9, Mar. 31, 2002 pp. 1-1.
Abst. No. 2006-039895 of CN1634865.
Ermert et al., Journal of Labelled compounds and Radiopharmaceuticals, vol. 43, No. 14, Dec. 31, 2000, pp. 1345-1363.
Rutsch et al., "New Photoinitiators for Pigmented Systems", Organic Coatings, Science and Technology, 1986, vol. 8, pp. 175-195.
Osorio-Olivares et al., "MAO inhibition by arylisopropylamines: the effect of oxygen substituents at the B-position", Bioorganic & Medicinal Chemistry, 2004, vol. 12, pp. 4055-4056.
English language machine-generated translation of FR 2626880 (18 Pages); 1989.

* cited by examiner

METAL FREE BLEACHING COMPOSITION

The present invention relates to the use of a composition comprising specific α-aminoketones, $H_2O_2$, a $H_2O_2$ precursor or a peracid and optionally an activator as a bleaching mixture for textile materials or dishes either manually or in an automatic washing machine or dish washer. Further aspects of the invention are the composition comprising specific α-aminoketones and $H_2O_2$, a $H_2O_2$ precursor or a peracid and a process for bleaching of stains or of soiling on textile materials or dishes in the context of a washing process either manually or in an automatic washing machine or dish washer. Also aspects of the invention are detergent formulations comprising such a composition and novel compounds.

Peroxide-containing bleaching agents have long been used in washing and cleaning processes. They have an excellent action at a liquor temperature of 90° C. and above, but their performance noticeably decreases with lower temperatures. Various transition metal ions added in the form of suitable salts, and coordination compounds containing such cations are known to activate $H_2O_2$. In that manner it is possible for the bleaching effect, which is unsatisfactory at lower temperatures, of $H_2O_2$ or precursors that release $H_2O_2$ and of other peroxo compounds, to be increased. They are important for practical purposes, in that respect, especially combinations of transition metal ions and ligands of which the peroxide activation is manifested in an increased tendency towards oxidation in relation to substrates and not only in a catalase-like disproportionation. The latter activation, which in the present case tends rather to be undesirable, could even impair the bleaching effects, which are inadequate at low temperatures, of $H_2O_2$ and its derivatives.

In terms of $H_2O_2$ activation having effective bleaching action, mononuclear and polynuclear variants of manganese complexes having various ligands, especially 1,4,7-trimethyl-1,4,7-triazacyclononane and optionally oxygen-containing bridging ligands, are currently regarded as being especially effective. Such catalysts are adequately stable under practical conditions and, with $Mn^{n+}$, contain an ecologically acceptable metal cation, but their use is unfortunately associated with considerable damage to dyes and fibres.

Another well known possibility to improve the bleaching effect at lower temperature is the use of bleach activators together with precursors of $H_2O_2$. Typical bleach activators are tetraacetylethylenediamine, pentaacetylglucose, sodium octanoyloxybenzenesulfonate, sodium nonanoyloxybenzenesulfonate, sodium decanoyloxybenzenesulfonate, sodium undecanoyloxybenzenesulfonate, sodium dodecanoyloxybenzenesulfonate, octanoyloxybenzoic acid, nonanoyloxybenzoic acid, decanoyloxybenzoic acid, undecanoyloxybenzoic acid, dodecanoyloxybenzoic acid, octanoyloxybenzene, nonanoyloxybenzene, decanoyloxybenzene, undecanoyloxybenzene and dodecanoyloxybenzene.

In WO 2008/014965 it has recently been suggested to use dialkylaminoacetone derivatives or salts thereof as bleaching activators together with inorganic peroxo compounds, especially peroxomonosulfate (oxone, caroat) instead of the classical bleach activators described above.

The aim of the present invention is to further improve the bleach process and to extend the bleach efficiency towards higher pH values. Surprisingly it has been found that specific α-aminoketones, $H_2O_2$, a $H_2O_2$ precursor or a peracid and optionally a known activator provide a highly efficient bleach composition. Since the present bleach composition is free of metal complexes, no appreciable fiber damage occurs, although the action of peroxide compounds in the most varied fields of application is considerably enhanced.

One aspect of the invention is the use of a composition comprising
a) $H_2O_2$, a precursor of $H_2O_2$, or a peracid and
b) a compound of formula (1) or (2)

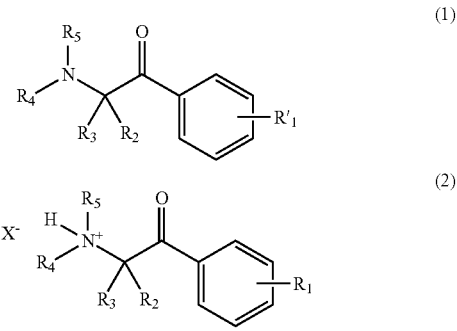

wherein
$X^-$ is the anion of an organic or inorganic acid;
$R_1$ is hydrogen, halogen, phenyl, phenoxy, phenylthio, phenyl-(SO)—, linear or branched $C_1$-$C_6$alkyl, $C_1$-$C_6$alkoxy, $C_1$-$C_6$alkylthio, $C_1$-$C_6$alkyl-S(O)—, $C_1$-$C_6$alkyl-SO$_2$—, which $C_1$-$C_6$alkyl is unsubstituted or substituted by OH or (CO)OR$_6$;
or $R_1$ is linear or branched $C_2$-$C_3$alkenyl which is unsubstituted or substituted by (CO)OR$_6$;
or $R_1$ is $S^+(R_7)(R_8)X'^-$;
$R_7$ and $R_8$ independently of each other are linear or branched $C_1$-$C_6$ alkyl;
or $R_7$ or $R_8$ is linear or branched $C_2$-$C_3$ alkenyl;
$X'^-$ has one of the definitions given for $X^-$ and is same or different;
or $R_1$ is $N^+(R_9)(R_{10})(R_{11})X''^-$;
$R_9$, $R_{10}$ and $R_{11}$ independently of each other are linear or branched $C_1$-$C_6$alkyl;
or $R_7$ or $R_8$ or $R_{11}$ is linear or branched $C_2$-$C_3$ alkenyl;
or $R_9$ and $R_{10}$ or $R_9$ and $R_{11}$ or $R_{10}$ and $R_{11}$ together with the Nitrogen atom to which they are bonded form a pyrrolidine, piperidine or morpholine group;
$X''^-$ has one of the definitions given for $X^-$ and $X'^-$ and is same or different;
$R'_1$ has one of the definitions given for $R_1$;
or $R'_1$ is linear or branched $C_1$-$C_6$alkyl, $C_1$-$C_6$alkoxy, $C_1$-$C_6$alkylthio, $C_1$-$C_6$alkyl-S(O)—, $C_1$-$C_6$alkyl-SO$_2$— which $C_1$-$C_6$alkyl is substituted by (CO)O$^-Z^+$;
or $R'_1$ is linear or branched $C_2$-$C_3$alkenyl substituted by (CO)O$^-Z^+$;
$R_2$ and $R_3$ independently of each other are hydrogen, linear or branched $C_1$-$C_6$alkyl which is unsubstituted or substituted by phenyl; or linear or branched $C_2$-$C_3$alkenyl;
or $R_2$ and $R_3$, together with the atom to which they are bonded form a cyclopentyl or cyclohexyl group;
$R_4$ and $R_5$ independently of each other are hydrogen, linear or branched $C_1$-$C_{12}$alkyl which is unsubstituted or substituted by 1 to 4 OH groups; unsubstituted $C_2$-$C_6$alkenyl, $C_1$-$C_6$alkyl which is interrupted by one or more O or $C_5$-$C_8$cycloalkyl;
or $R_4$ and $R_5$ together with the Nitrogen atom to which they are bonded form a pyrrolidine, piperidine or morpholine group or hexamethyleneimine;
$R_6$ is hydrogen or linear or branched $C_1$-$C_3$alkyl;
$Z^+$ is $Na^+$, $K^+$ or $NH_4^+$;

for the bleaching of stains or of soiling on textile materials or for the cleaning of dishes;

with the proviso that if in formulae (1) and (2) $R_1$, $R'_1$, $R_2$ and $R_3$ are hydrogen, $R_4$ and $R_5$ are not unsubstituted $C_1$-$C_{12}$alkyl or unsubstituted $C_2$-$C_6$alkenyl.

In a specific embodiment it is the use of a composition comprising
a) $H_2O_2$, a precursor of $H_2O_2$, a peracid and
b) a compound of formula (1) or (2)

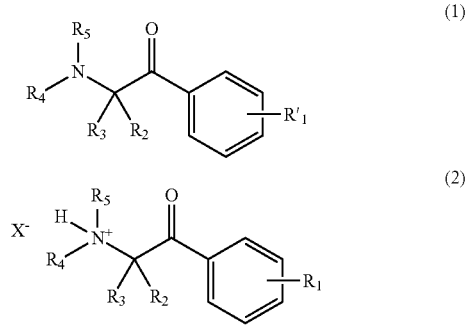

wherein
$X^-$ is the anion of an organic or inorganic acid;

$R_1$ is hydrogen, halogen, phenyl, phenoxy, phenylthio, phenyl-(SO)—, linear or branched $C_1$-$C_6$alkyl, $C_1$-$C_6$alkoxy, $C_1$-$C_6$alkylthio, $C_1$-$C_6$alkyl-S(O)—, $C_1$-$C_6$alkyl-SO$_2$—, which $C_1$-$C_6$alkyl is unsubstituted or substituted by OH or (CO)OR$_6$;

or $R_1$ is linear or branched $C_2$-$C_3$alkenyl which is unsubstituted or substituted by (CO)OR$_6$;

$R'_1$ has one of the definitions given for $R_1$;

or $R'_1$ is linear or branched $C_1$-$C_6$alkyl, $C_1$-$C_6$alkoxy, $C_1$-$C_6$alkylthio, $C_1$-$C_6$alkyl-S(O)—, $C_1$-$C_6$alkyl-SO$_2$— which $C_1$-$C_6$alkyl is substituted by (CO)O$^-$Z$^+$;

or $R'_1$ is linear or branched $C_2$-$C_3$alkenyl substituted by (CO)O$^-$Z$^+$;

$R_2$ and $R_3$ independently of each other are hydrogen, linear or branched $C_1$-$C_6$alkyl which is unsubstituted or substituted by phenyl; or linear or branched $C_2$-$C_3$alkenyl;

or $R_2$ and $R_3$, together with the atom to which they are bonded form a cyclopentyl or cyclohexyl group;

$R_4$ and $R_5$ independently of each other are hydrogen, linear or branched $C_1$-$C_{12}$alkyl which is unsubstituted or substituted by 1 to 4 OH groups; unsubstituted $C_2$-$C_6$alkenyl, $C_1$-$C_6$alkyl which is interrupted by one or more O or $C_5$-$C_8$cycloalkyl;

or $R_4$ and $R_5$ together with the Nitrogen atom to which they are bonded form a pyrrolidine, piperidine or morpholine group or hexamethyleneimine;

$R_6$ is hydrogen or linear or branched $C_1$-$C_3$alkyl;
$Z^+$ is Na$^+$, K$^+$ or NH$_4^+$;

for the bleaching of stains or of soiling on textile materials or for the cleaning of dishes; with the proviso that if in formulae (1) and (2) $R_1$, $R'_1$, $R_2$ and $R_3$ are hydrogen, $R_4$ and $R_5$ are not unsubstituted $C_1$-$C_{12}$alkyl or unsubstituted $C_2$-$C_6$alkenyl.

The inorganic or organic anion $X^-$ may be an anion such as RCOO$^-$, ClO$_4^-$, BF$_4^-$, PF$_6^-$, RSO$_3^-$, RSO$_4^-$, SO$_4^{2-}$, H$_2$PO$_4^-$, HPO$_4^{2-}$, OCN$^-$, SCN$^-$, NO$_3^-$, F$^-$, Cl$^-$, Br$^-$ or HCO$_3^-$, with R being hydrogen, optionally substituted $C_1$-$C_{24}$alkyl or optionally substituted aryl. Examples are lactic acid, citric acid, tartaric acid, succinic acid.

For anions with a charge greater than −1 the charge balance is established by additional cations, such as H$^+$, Na$^+$, K$^+$, NH$_4^+$, or the protonated form of a compound of formula (1).

Preferably $X^-$ is RCOO$^-$, ClO$_4^-$, BF$_4^-$, PF$_6^-$, RSO$_3^-$, RSO$_4^-$, SO$_4^{2-}$, NO$_3^-$, F$^-$, Cl$^-$, Br$^-$ and I$^-$ wherein R is linear or branched $C_1$-$C_{18}$alkyl or phenyl.

Preferably $R_4$ and $R_5$ together with the Nitrogen atom to which they are bonded form a pyrrolidine, piperidine, morpholine or heaxmethyleneimine group, in particular a morpholine group.

Preferably $R_2$ and $R_3$ are $C_1$-$C_4$alkyl, in particular methyl.

The various $C_1$-$C_6$ alkyl groups are, for example, methyl, ethyl, propyl, butyl, pentyl or hexyl and their various isomers.

The compounds are partially known and may be prepared according to standard procedures, such as for example described in GB 2 320 027.

Component a) of the composition may be $H_2O_2$, a precursor of $H_2O_2$ or a peracid, which are present in an aqueous washing process. Preferred are precursors of $H_2O_2$, such as peroxides or peracids outlined below. In particular preferred are inorganic peroxides.

As precursors of $H_2O_2$ peroxides come into consideration. I.e. every compound which is capable of yielding hydrogen peroxide in aqueous solutions, for example, the organic and inorganic peroxides known in the literature and available commercially that bleach textile materials at conventional washing temperatures, for example at from 10 to 95° C.

Preferably, however, inorganic peroxides are used, for example persulfates, perborates, percarbonates and/or persilicates.

Examples of suitable inorganic peroxides are sodium perborate tetrahydrate or sodium perborate monohydrate, sodium percarbonate, inorganic peroxyacid compounds, such as for example potassium monopersulphate (MPS). If organic or inorganic peroxyacids are used as the peroxygen compound, the amount thereof will normally be within the range of about 2-80 wt-%, preferably from 4-30 wt-%.

The organic peroxides are, for example, mono- or polyperoxides, urea peroxides, a combination of a $C_1$-$C_4$alkanol oxidase and $C_1$-$C_4$alkanol (Such as methanol oxidase and ethanol as described in WO95/07972), alkylhydroxy peroxides, such as cumene hydroperoxide and t-butyl hydroperoxide.

The peroxides may be in a variety of crystalline forms and have different water contents, and they may also be used together with other inorganic or organic compounds in order to improve their storage stability.

As oxidants, peroxo acids can also be used. One example are organic mono peracids of formula

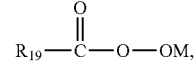

wherein
M signifies hydrogen or a cation,
$R_{19}$ signifies unsubstituted $C_1$-$C_{18}$alkyl; substituted $C_1$-$C_{18}$alkyl; unsubstituted aryl; substituted aryl; —(C$_1$-C$_6$alkylene)-aryl, wherein the alkylene and/or the alkyl group may be substituted; and phthalimidoC$_1$-$C_8$alkylene, wherein the phthalimido and/or the alkylene group may be substituted.

Preferred mono organic peroxy acids and their salts are those of formula

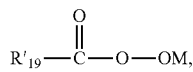

wherein

M signifies hydrogen or an alkali metal, and $R'_{19}$ signifies unsubstituted $C_1$-$C_4$alkyl; phenyl; —$C_1$-$C_2$alkylene-phenyl or phthalimido$C_1$-$C_8$alkylene.

Especially preferred is $CH_3COOOH$ and its alkali salts.

Especially preferred is also E-phthalimido peroxy hexanoic acid and its alkali salts.

Also suitable are diperoxyacids, for example, 1,12-diperoxydodecanedioic acid (DPDA), 1,9-diperoxyazelaic acid, diperoxybrassilic acid, diperoxysebasic acid, diperoxyisophthalic acid, 2-decyldiperoxybutane-1,4-diotic acid and 4,4'-sulphonylbisperoxybenzoic acid.

In some cases the use of an additional bleach activator may be of advantage.

In a specific embodiment component a) comprises a precursor of $H_2O_2$ and a bleach activator.

The weight ratio between the precursor of $H_2O_2$ and the bleach activator can vary from 10:1 to 1:1.

The term bleach activator is frequently used as a synonym for peroxyacid bleach precursor. All the above mentioned peroxy compounds may be utilized alone or in conjunction with a peroxyacid bleach precursor. Generally, the bleaching composition of the invention can be suitably formulated to contain from 0.25 to 60 wt-%, preferably from 0.5 to 30 wt-%, of the peroxy bleaching agent.

Such precursors are the corresponding carboxyacid or the corresponding carboxyanhydrid or the corresponding carbonylchlorid, or amides, or esters, which can form the peroxy acids on perhydrolysis. Such reactions are commonly known.

Peroxyacid bleach precursors are known and amply described in literature, such as in the British Patents 836988; 864,798; 907,356; 1,003,310 and 1,519,351; German Patent 3,337,921; EP-A-0185522; EP-A-0174132; EP-A-0120591; and U.S. Pat. Nos. 1,246,339; 3,332,882; 4,128,494; 4,412,934 and 4,675,393.

Suitable bleach activators include the bleach activators, that carry O- and/or N-acyl groups and/or unsubstituted or substituted benzoyl groups. Preference is given to polyacylated alkylenediamines, especially tetraacetylethylenediamine (TAED); acylated glycolurils, especially tetraacetyl glycol urea (TAG U), N,N-diacetyl-N,N-dimethylurea (DDU); sodium-4-benzoyloxy benzene sulphonate (SBOBS); sodium-1-methyl-2-benzoyloxy benzene-4-sulphonate; sodium-4-methyl-3-benzoloxy benzoate; trimethyl ammonium toluoyloxybenzene sulphonate; acylated triazine derivatives, especially 1,5-diacetyl-2,4-dioxohexahydro-1,3,5-triazine (DADHT); compounds of formula (6):

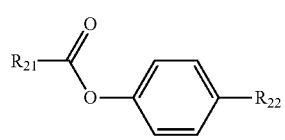

(10)

wherein $R_{22}$ is a sulfonate group, a carboxylic acid group or a carboxylate group, and wherein $R_{21}$ is linear or branched ($C_7$-$C_{15}$)alkyl, especially activators known under the names SNOBS, SLOBS and DOBA; acylated polyhydric alcohols, especially triacetin, ethylene glycol diacetate and 2,5-diacetoxy-2,5-dihydrofuran; and also acetylated sorbitol and mannitol and acylated sugar derivatives, especially pentaacetylglucose (PAG), sucrose polyacetate (SUPA), pentaacetylfructose, tetraacetylxylose and octaacetyllactose as well as acetylated, optionally N-alkylated glucamine and gluconolactone. It is also possible to use the combinations of conventional bleach activators known from German Patent Application DE-A-44 43 177. Nitrile compounds that form perimine acids with peroxides also come into consideration as bleach activators.

Another useful class of peroxyacid bleach precursors is that of the cationic i.e. quaternary ammonium substituted peroxyacid precursors as disclosed in U.S. Pat. Nos. 4,751,015 and 4,397,757, in EP-A0284292 and EP-A-331,229. Examples of peroxyacid bleach precursors of this class are: 2-(N,N,N-trimethyl ammonium) ethyl sodium-4-sulphonphenyl carbonate chloride—(SPCC), N-octyl,N,N-dimethyl-N10-carbophenoxy decyl ammonium chloride—(ODC), 3-(N,N,N-trimethyl ammonium) propyl sodium-4-sulphophenyl carboxylate and N,N,N-trimethyl ammonium toluoyloxy benzene sulphonate.

A further special class of bleach precursors is formed by the cationic nitriles as disclosed in EP-A-303,520, WO 96/40661 and in European Patent Specification No.'s 458, 396, 790244 and 464,880. These cationic nitriles also known as nitril quats have the formula

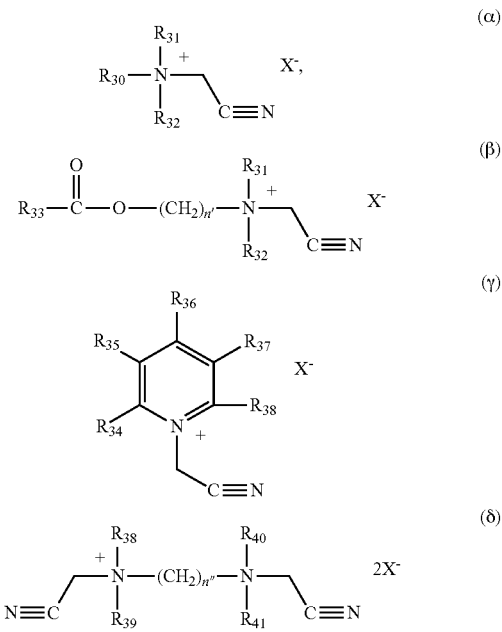

wherein $R_{30}$ is a $C_1$-$C_{24}$alkyl; a $C_1$-$C_{24}$alkenyl; an alkaryl having a $C_1$-$C_{24}$alkyl; a substituted $C_1$-$C_{24}$alkyl; a substituted $C_1$-$C_{24}$alkenyl; a substituted aryl, $R_{31}$ and $R_{32}$ are each independently a $C_1$-$C_3$alkyl; hydroxyalkyl having 1 to 3 carbon atoms, —$(C_2H_4O)_n$H, n being 1 to 6; —$CH_2$—CN $R_{33}$ is a $C_1$-$C_{20}$alkyl; a $C_1$-$C_{20}$alkenyl; a substituted $C_1$-$C_{20}$alkyl; a substituted $C_1$-$C_{20}$alkenyl; an alkaryl having a $C_1$-$C_{24}$alkyl and at least one other substituent, $R_{34}$, $R_{35}$, $R_{36}$, $R_{37}$ and $R_{38}$ are each independently hydrogen, a $C_1$-$C_{10}$alkyl, a $C_1$-$C_{10}$alkenyl, a substituted $C_1$-$C_{10}$alkyl, a substituted $C_1$-$C_{10}$alkenyl, carboxyl, sulfonyl or cyano $R_{38}$, $R_{39}$, $R_{40}$ and $R_{41}$ are each independently a $C_1$-$C_6$alkyl, n' is an integer from 1 to 3, n" is an integer from 1 to 16, and X is an anion.

Other nitril quats have the following formula

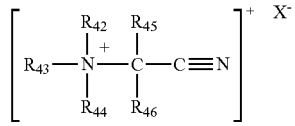

(ε)

wherein $R_{42}$ and $R_{43}$ form, together with the nitrogen atom to which they are bonded, a ring comprising 4 to 6 carbon atoms, this ring may also be substituted by $C_1$-$C_5$-alkyl, $C_1$-$C_5$-alkoxy, $C_1$-$C_5$-alkanoyl, phenyl, amino, ammonium, cyano, cyanamino or chloro and 1 or 2 carbon atom(s) of this ring may also be substituted by a nitrogen atom, by a oxygen atom, by a N—$R_{47}$-group and/or by a $R_{44}$—N—$R_{47}$-group, wherein $R_{47}$ is hydrogen, $C_1$-$C_5$-alkyl, $C_2$-$C_5$-alkenyl, $C_2$-$C_5$-alkinyl, phenyl, $C_7$-$C_9$-aralkyl, $C_5$-$C_7$-cycloalkyl, $C_1$-$C_5$-alkanoyl, cyanomethyl or cyano, $R_{44}$ is $C_1$-$C_{24}$-, preferably $C_1$-$C_4$-alkyl; $C_2$-$C_{24}$-alkenyl, preferably $C_2$-$C_4$-alkenyl, cyanomethyl or $C_1$-$C_4$-alkoxy-$C_1$-$C_4$-alkyl, $R_{45}$ and $R_{46}$ are independently from each other hydrogen; $C_1$-$C_4$-alkyl; $C_1$-$C_4$-alkenyl; $C_1$-$C_4$-alkoxy-$C_1$-$C_4$-alkyl; phenyl or $C_1$-$C_3$-alkylphenyl, preferably hydrogen, methyl or phenyl, whereby preferably the moiety $R_{45}$ signifies hydrogen, if $R_{46}$ is not hydrogen, and X⁻ is an anion.

Suitable examples of nitril quats of formula (ε) are

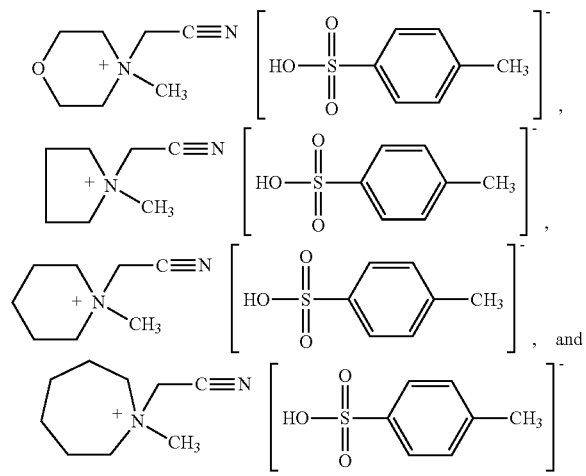

Other nitrile quats have the formula

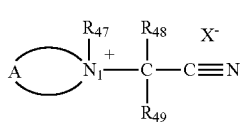

(φ)

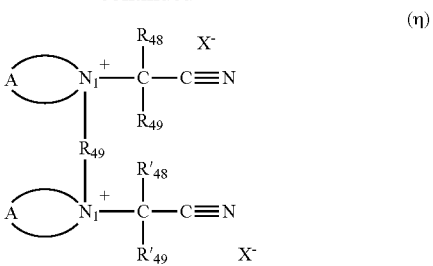

wherein

A is a saturated ring formed by a plurality of atoms in addition to the $N_1$ atom, the saturated ring atoms to include at least one carbon atom and at least one heteroatom in addition to the $N_1$ atom, the said one heteroatom selected from the group consisting of O, S and N atoms, the substituent $R_{47}$ bound to the $N_1$ atom of the Formula (φ) structure is (a) a $C_1$-$C_8$-alkyl or alkoxylated alkyl where the alkoxy is $C_{2-4}$, (b) a $C_4$-$C_{24}$cycloalkyl, (c) a $C_7$-$C_{24}$alkaryl, (d) a repeating or nonrepeating alkoxy or alkoxylated alcohol, where the alkoxy unit is $C_{2-4}$, or (e) —$CR_{50}R_{51}$—CN where $R_{50}$ and $R_{51}$ are each H, a $C_1$-$C_{24}$alkyl, cycloalkyl, or alkaryl, or a repeating or nonrepeating alkoxyl or alkoxylated alcohol where the alkoxy unit is $C_2$-$C_4$, in Formula (φ) at least one of the $R_{48}$ and $R_{49}$ substituents is H and the other of $R_{48}$ and $R_{49}$ is H, a $C_1$-$C_{24}$alkyl, cycloalkyl, or alkaryl, or a repeating or nonrepeating alkoxyl or alkoxylated alcohol where the alkoxy unit is $C_{2-4}$, and Y is at least one counterion.

In a preferred embodiment of the invention the compounds of formula (1) or (2) are used together with a peroxide or peroxide precursor and a bleach activator which is selected from the group consisting of tetraacetylethylenediamine, pentaacetylglucose, sodium α-tanoyloxybenzenesulfonate, sodium nonanoyloxybenzenesulfonate, sodium decanoyloxybenzenesulfonate, sodium undecanoyloxybenzenesulfonate, sodium dodecanoyloxybenzenesulfonate, octanoyloxybenzoic acid, nonanoyloxybenzoic acid, decanoyloxybenzoic acid, undecanoyloxybenzoic acid, dodecanoyloxybenzoic acid, octanoyloxybenzene, nonanoyloxybenzene, decanoyloxybenzene, undecanoyloxybenzene and dodecanoyloxybenzene.

The bleach activators (precursors) may be used in an amount of up to 12 wt-%, preferably from 2-10 wt-% based on the total weight of the composition.

It is also possible to use further bleach catalysts, which are commonly known, for example transition metal complexes as disclosed in EP 1194514, EP 1383857 or WO04/007657. Further bleach catalysts are disclosed in: US2001044401, EP0458397, WO9606154, EP1038946, EP0900264, EP0909809, EP1001009, WO9965905, WO0248301, WO0060045, WO02077145, WO0185717, WO0164826, EP0923635, DE 19639603, DE102007017654, DE102007017657, DE102007017656, US20030060388, EP0918840B1, EP1174491A2, EP0805794B1, WO9707192A1, U.S. Pat. No. 6,235,695B1, EP0912690B1, EP832969B1, U.S. Pat. No. 6,479,450B1, WO9933947A1, WO0032731A1, WO03054128A1, DE102004003710, EP1083730, EP1148117, EP1445305, U.S. Pat. No. 6,476, 996, EP0877078, EP0869171, EP0783035, EP0761809 and EP1520910.

Preferably the compound of formula (1) or (2) is water soluble.

Water soluble in the context of the present invention means a solubility in demineralised water at 25° C. and atmospheric pressure of at least 0.5 g in 100 g water.

Typically component a) is present in an amount of from 2 parts to 90 parts by weight and component b) is present in an amount of from 0.02 parts to 20 parts by weight; the sum being 100 parts.

Typically the composition is used for the bleaching of stains or of soiling on textile materials in the context of a washing process or by the direct application of a stain remover at a pH between 7 and 11.

For example the temperature of the washing process is between 5° C. and 95° C. Preferably the temperature is between 10° C. and 60° C., more preferably between 10° C. and 40° C. In particular 30° C.

For instance in formulae (1) and (2)

$X^-$ is the anion of an organic or inorganic acid;

$R_1$ is hydrogen, linear or branched $C_1$-$C_6$alkyl, $C_1$-$C_6$alkoxy, $C_1$-$C_6$alkylthio, $C_1$-$C_6$alkyl-S(O)—, $C_1$-$C_6$alkyl-SO$_2$—;

or $R_1$ is $S^+(R_7)(R_8)$ $X'^-$;

$R_7$ and $R_8$ independently of each other are linear or branched $C_1$-$C_6$ alkyl;

$X'^-$ has one of the definitions given for $X^-$ and is same or different;

or $R_1$ is $N^+(R_9)(R_{10})(R_{11})$ $X'''^-$;

$R_9$, $R_{10}$ and $R_{11}$ independently of each other are linear or branched $C_1$-$C_6$alkyl;

or $R_9$ and $R_{10}$ or $R_9$ and $R_{11}$ or $R_{10}$ and $R_{11}$ together with the Nitrogen atom to which they are bonded form a pyrrolidine, piperidine or morpholine group;

$X'''^-$ has one of the definitions given for $X^-$ and $X'^-$ and is same or different;

$R'_1$ has one of the definitions given for $R_1$;

$R_2$ and $R_3$ independently of each other are hydrogen or linear or branched $C_1$-$C_6$alkyl;

$R_4$ and $R_5$ independently of each other are hydrogen, linear or branched $C_1$-$C_{12}$alkyl which is unsubstituted or substituted by 1 to 4 OH groups; unsubstituted $C_2$-$C_6$alkenyl, $C_1$-$C_6$alkyl which is interrupted by one or more O or $C_5$-$C_8$cycloalkyl;

or $R_4$ and $R_5$ together with the Nitrogen atom to which they are bonded form a pyrrolidine, piperidine or morpholine group or hexamethyleneimine.

For example the compound of formula (1) or (2) conforms to a compound of formula (3)

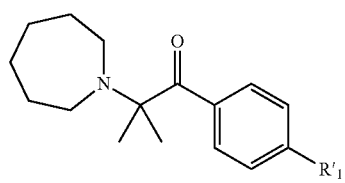

wherein $R'_1$ is $SCH_3$, $S(O_2)CH_3$, H, $CH_3$, $S(O)CH_3$, $(CH_3)_2S^+$ $BF_4^-$ or $(CH_3)_2S^+(CH_3O)S(O_2)O^-$; or to a compound of formula (4)

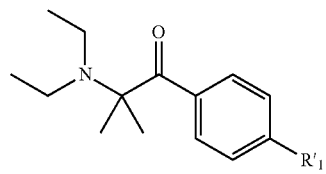

wherein $R'_1$ is H, $CH_3$, $SCH_3$, $S(O)CH_3$, $S(O_2)CH_3$, $(CH_3)_2S^+$ $BF_4^-$ or $(CH_3)_2S^+(CH_3O)S(O_2)O^-$; or to a compound of formula (5)

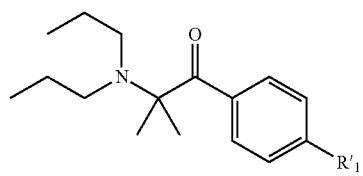

wherein $R'_1$ is $SCH_3$, $S(O_2)CH_3$, H, $CH_3$, $S(O)CH_3$, $(CH_3)_2S^+$ $BF_4^-$ or $(CH_3)_2S^+(CH_3O)S(O_2)O^-$; or to a compound of formula (6)

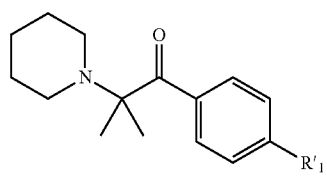

wherein $R'^1$=$SCH_3$, $S(O)CH_3$, $S(O_2)CH_3$, $(CH_3)_2S^+BF_4^-$ or $(CH_3)_2S^+(CH_3O)S(O_2)O^-$; or to a compound of formula (7)

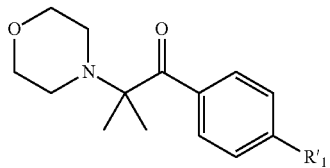

wherein $R'^1$=H, $SCH_3$, $S(O)CH_3$, $S(O_2)CH_3$, $(CH_3)(CH_3CH_2)S^+$ $(CH_3)_2S^+(CH_3)_2S^+PF_6^-$ or $(CH_3)_2S^+(CH_3O)S(O_2)O^-$; or to a compound of formula (8)

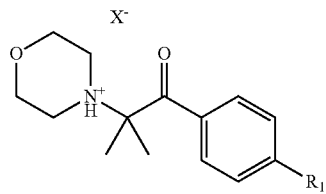

wherein $R_1$ is $SCH_3$ and $X^-$ is $Cl^-$ or $BF_4^-$.

Preferred are compounds of the formula (1) wherein $R_2$ and $R_3$=methyl, $R_4$ and $R_5$ together with the nitrogen atom to which they are bonded form a piperidine group and $R'_1$ is defined as described below:

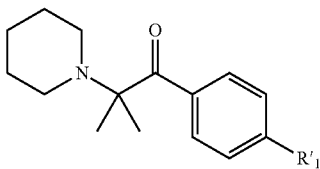

Formula (6)

$R'_1$=SCH$_3$ (compound 29), S(O)CH$_3$ (compound 40), S(O$_2$)CH$_3$ (compound 41), (CH$_3$)$_2$S$^+$BF$_4^-$ (compound 44) and (CH$_3$)$_2$S$^+$(CH$_3$O)S(O$_2$)O$^-$ (compound 43); or compounds of the formula (1) wherein $R_2$ and $R_3$=methyl, $R_4$ and $R_5$ together with the nitrogen atom to which they are bonded form a morpholine group and $R'_1$ is defined as described below:

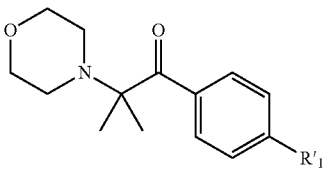

Formula (7)

$R'_1$=H (compound 7), SCH$_3$ (compound 1), S(O)CH$_3$ (compound 5), S(O$_2$)CH$_3$ (compound 6), (CH$_3$)(CH$_3$CH$_2$)S$^+$BF$_4^-$ (compound 13), (CH$_3$)$_2$S$^+$BF$_4^-$ (compound 28), (CH$_3$)$_2$S$^+$PF$_6^-$ (compound 27) and (CH$_3$)$_2$S$^+$(CH$_3$O)S(O$_2$)O$^-$ (compound 26);

or compounds of the formula (2) wherein $R_2$ and $R_3$=methyl, $R_4$ and $R_5$ together with the nitrogen atom to which they are bonded form a morpholine group, $R_1$=SCH$_3$ and X$^-$ is defined as described below:

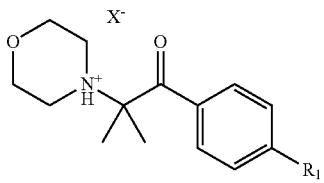

Formula (8)

X$^-$=Cl$^-$ (compound 3), BF$_4^-$ (compound 2).

Another aspect of the invention is a composition comprising a) H$_2$O$_2$ or a precursor of H$_2$O$_2$ or a peracid and b) a compound of formula (1) or (2)

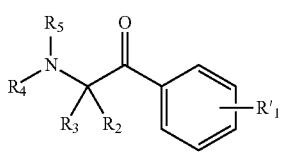

(1)

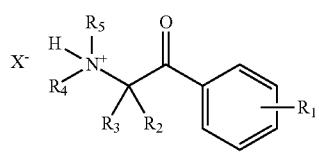

(2)

wherein

X$^-$ is the anion of an organic or inorganic acid;

$R_1$ is hydrogen, halogen, phenyl, phenoxy, phenylthio, phenyl-(SO)—, linear or branched $C_1$-$C_6$alkyl, $C_1$-$C_6$alkoxy, $C_1$-$C_6$alkylthio, $C_1$-$C_6$alkyl-S(O)—, $C_1$-$C_6$alkyl-SO$_2$—, which $C_1$-$C_6$alkyl is unsubstituted or substituted by OH or (CO)OR$_6$;

or $R_1$ is linear or branched $C_2$-$C_3$alkenyl which is unsubstituted or substituted by (CO)OR$_6$;

or $R_1$ is S$^+$(R$_7$)(R$_8$) X$'^-$;

$R_7$ and $R_8$ independently of each other are linear or branched $C_1$-$C_6$ alkyl;

or $R_7$ or $R_8$ is linear or branched $C_2$-$C_3$ alkenyl;

X$'^-$ has one of the definitions given for X$^-$ and is same or different;

or $R_1$ is N$^+$(R$_9$)(R$_{10}$)(R$_{11}$)X$''^-$;

$R_9$, $R_{10}$ and $R_{11}$ independently of each other are linear or branched $C_1$-$C_6$alkyl;

or $R_7$ or $R_8$ or $R_{11}$ is linear or branched $C_2$-$C_3$ alkenyl;

or $R_9$ and $R_{10}$ or $R_9$ and $R_{11}$ or $R_{10}$ and $R_{11}$ together with the Nitrogen atom to which they are bonded form a pyrrolidine, piperidine or morpholine group;

X$'''^-$ has one of the definitions given for X$^-$ and X$'^-$ and is same or different;

$R'_1$ has one of the definitions given for $R_1$;

or $R'_1$ is linear or branched $C_1$-$C_6$alkyl, $C_1$-$C_6$alkoxy, $C_1$-$C_6$alkylthio, $C_1$-$C_6$alkyl-S(O)—, $C_1$-$C_6$alkyl-SO$_2$— which $C_1$-$C_6$alkyl is substituted by (CO)O$^-$Z$^+$;

or $R'_1$ is linear or branched $C_2$-$C_3$alkenyl substituted by (CO)O$^-$Z$^+$;

$R_2$ and $R_3$ independently of each other are hydrogen, linear or branched $C_1$-$C_6$alkyl which is unsubstituted or substituted by phenyl; or linear or branched $C_2$-$C_3$alkenyl;

or $R_2$ and $R_3$, together with the atom to which they are bonded form a cyclopentyl or cyclohexyl group;

$R_4$ and $R_5$ independently of each other are hydrogen, linear or branched $C_1$-$C_{12}$alkyl which is unsubstituted or substituted by 1 to 4 OH groups; unsubstituted $C_2$-$C_6$alkenyl, $C_1$-$C_6$alkyl which is interrupted by one or more O or $C_5$-$C_8$cycloalkyl;

or R$^4$ and R$^5$ together with the Nitrogen atom to which they are bonded form a pyrrolidine, piperidine or morpholine group or hexamethyleneimine;

$R_6$ is hydrogen or linear or branched $C_1$-$C_3$alkyl;

Z$^+$ is Na$^+$, K$^+$ or NH$_4^+$;

for the bleaching of stains or of soiling on textile materials or for the cleaning of dishes; with the proviso that if in formulae (1) and (2) $R_1$, $R'_1$, $R_2$ and $R_3$ are hydrogen, $R_4$ and $R_5$ are not unsubstituted $C_1$-$C_{12}$alkyl or unsubstituted $C_2$-$C_6$alkenyl.

Also an aspect of the invention is a process for the bleaching of stains or of soiling on textile materials or dishes in the context of a washing process or by the direct application of a stain remover comprising treating a textile material or dishes in an aqueous medium either by hand or in an automatic washing machine or dishwasher, together with a mixture comprising a) H$_2$O$_2$, a precursor of H$_2$O$_2$ or a peracid and b) a compound of formula (1) or (2)

wherein

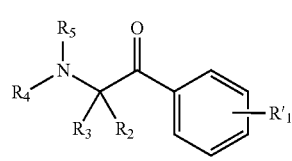

(1)

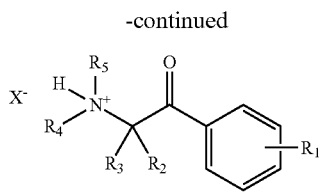

(2)

$X^-$ is the anion of an organic or inorganic acid;

$R^1$ is hydrogen, halogen, phenyl, phenoxy, phenylthio, phenyl-(SO)—, linear or branched $C_1$-$C_6$alkyl, $C_1$-$C_6$alkoxy, $C_1$-$C_6$alkylthio, $C_1$-$C_6$alkyl-S(O)—, $C_1$-$C_6$alkyl-$SO_2$—, which $C_1$-$C_6$alkyl is unsubstituted or substituted by OH or $(CO)OR_6$;

or $R_1$ is linear or branched $C_2$-$C_3$alkenyl which is unsubstituted or substituted by $(CO)OR_6$;

or $R_1$ is $S^+(R_7)(R_8)X'^-$;

$R_7$ and $R_8$ independently of each other are linear or branched $C_1$-$C_6$ alkyl;

or $R_7$ or $R_8$ is linear or branched $C_2$-$C_3$ alkenyl;

$X'^-$ has one of the definitions given for $X^-$ and is same or different;

or $R_1$ is $N^+(R_9)(R_{10})(R_{11})X''^-$;

$R_9$, $R_{10}$ and $R_{11}$ independently of each other are linear or branched $C_1$-$C_6$alkyl;

or $R_7$ or $R_8$ or $R_{11}$ is linear or branched $C_2$-$C_3$ alkenyl;

or $R_9$ and $R_{10}$ or $R_9$ and $R_{11}$ or $R_{10}$ and $R_{11}$ together with the Nitrogen atom to which they are bonded form a pyrrolidine, piperidine or morpholine group;

$X''^-$ has one of the definitions given for $X^-$ and $X'^-$ and is same or different;

$R'_1$ has one of the definitions given for $R_1$;

or $R'_1$ is linear or branched $C_1$-$C_6$alkyl, $C_1$-$C_6$alkoxy, $C_1$-$C_6$alkylthio, $C_1$-$C_6$alkyl-S(O)—, $C_1$-$C_6$alkyl-$SO_2$— which $C_1$-$C_6$alkyl is substituted by $(CO)O^-Z^+$;

or $R'_1$ is linear or branched $C_2$-$C_3$alkenyl substituted by $(CO)O^-Z^+$;

$R_2$ and $R_3$ independently of each other are hydrogen, linear or branched $C_1$-$C_6$alkyl which is unsubstituted or substituted by phenyl; or linear or branched $C_2$-$C_3$alkenyl;

or $R_2$ and $R_3$, together with the atom to which they are bonded form a cyclopentyl or cyclohexyl group;

$R_4$ and $R_5$ independently of each other are hydrogen, linear or branched $C_1$-$C_{12}$alkyl which is unsubstituted or substituted by 1 to 4 OH groups; unsubstituted $C_2$-$C_6$alkenyl, $C_1$-$C_6$alkyl which is interrupted by one or more O or $C_5$-$C_8$cycloalkyl;

or $R_4$ and $R_5$ together with the Nitrogen atom to which they are bonded form a pyrrolidine, piperidine or morpholine group or hexamethyleneimine;

$R_6$ is hydrogen or linear or branched $C_1$-$C_3$alkyl;

$Z^+$ is $Na^+$, $K^+$ or $NH_4^+$;

for the bleaching of stains or of soiling on textile materials or for the cleaning of dishes;

with the proviso that if in formulae (1) and (2) $R_1$, $R'_1$, $R_2$ and $R_3$ are hydrogen, $R_4$ and $R_5$ are not unsubstituted $C_1$-$C_{12}$alkyl or unsubstituted $C_2$-$C_6$alkenyl.

Since the subject of the invention is used for the bleaching of stains or of soiling on textile materials or dishes in the context of a washing process or by the direct application of a stain remover, a further aspect is a detergent, cleaning or bleaching composition comprising I) from 0.1 to 50 wt-%, based on the total weight of the composition, A) of at least one anionic surfactant and/or B) of a non-ionic surfactant, II) from 0 to 70 wt-%, based on the total weight of the composition, C) of at least one builder substance, III) from 0.02 to 80 wt-% of a composition as described above, IV) from 0-20 wt-%, based on the total weight of the composition, of at least one further additive.

The composition may optionally also contain water, or a filler material, such as $Na_2SO_4$. The sum of the components I) to IV) and optionally further components adds to 100%.

All wt-% are based on the total weight of the detergent, cleaning or bleaching composition.

The detergent, cleaning or bleaching compositions can be any kind of industrial or domestic cleaning or bleaching formulation.

The detergents may be in solid, liquid, gel-like or paste-like form. The detergents may also be in the form of powders or (super-)compact powders or granules, in the form of single- or multi-layer tablets (tabs), in the form of washing agent bars, washing agent blocks, washing agent sheets, washing agent pastes or washing agent gels, or in the form of powders, pastes, gels or liquids used in capsules or in pouches (sachets).

When the composition is used in a washing process the concentration of the $H_2O_2$ or its precursor, such as perborate or percarbonate may vary in the range from 0.05 g/L to 15 g/L, preferably 0.05 g/L to 8 g/L and more preferably from 0.05 g/L to 2 g/L. If an additional activator is used, the activator, such as tetraacetylethylenediamine may vary from 0.01 g/L to 5 g/L, preferably from 0.015 g/L to 3 g/L, more preferably from 0.015 g/L to 1 g/L. The compound of formula (1) or (2) may vary from 5 µmol/L to 1 mmol/L, preferably from 5 µmol/L to 0.5 mmol/L, more preferably from 20 µmol/L to 0.3 mmol/L.

It is also possible to use additional bleach catalysts, which are commonly known, for example transition metal complexes as disclosed in EP 1194514, EP 1383857 or WO04/007657.

When the detergent compositions according to the invention comprise a component A) and/or B), the amount thereof is preferably from 0.5 to 50 wt-%, especially from 0.5 to 30 wt-%.

When the detergent compositions according to the invention comprise a component C), the amount thereof is preferably from 1 to 70 wt-%, especially from 1 to 50 wt-%. Special preference is given to an amount of from 5 to 50 wt-% and especially an amount of from 10 to 50 wt-%.

The composition according to the invention can be, for example, a peroxide-containing heavy-duty detergent or a separate bleaching additive, or a stain remover that is to be applied directly. A bleaching additive is used for removing coloured stains on textiles in a separate liquor before the clothes are washed with a detergent. A bleaching additive can also be used in a liquor together with a detergent.

Stain removers can be applied directly to the textile in question and are used especially for pretreatment in the event of heavy local soiling.

The stain remover can be applied in liquid form, by a spraying method or in the form of a solid substance, such as a powder especially as a granule.

The anionic surfactant A) can be, for example, a sulfate, sulfonate or carboxylate surfactant or a mixture thereof. Preference is given to alkylbenzenesulfonates, alkyl sulfates, alkyl ether sulfates, olefin sulfonates, fatty acid salts, alkyl and alkenyl ether carboxylates or to an α-sulfonic fatty acid salt or an ester thereof.

Preferred sulfonates are, for example, alkylbenzenesulfonates having from 10 to 20 carbon atoms in the alkyl radical, alkyl sulfates having from 8 to 18 carbon atoms in the alkyl radical, alkyl ether sulfates having from 8 to 18 carbon atoms in the alkyl radical, and fatty acid salts derived from palm oil or tallow and having from 8 to 18 carbon atoms in the alkyl moiety. The average molar number of ethylene oxide units added to the alkyl ether sulfates is from 1 to 20, preferably from 1 to 10. The cation in the anionic surfactants is preferably an alkaline metal cation, especially sodium or potassium, more especially sodium. Preferred carboxylates are alkali metal sarcosinates of formula $R_{19}$—CON($R_{20}$)CH$_2$COOM$_1$ wherein $R_{19}$ is $C_9$-$C_{17}$alkyl or $C_9$-$C_{17}$alkenyl, $R_{20}$ is $C_1$-$C_4$alkyl and $M_1$ is an alkali metal, especially sodium.

The non-ionic surfactant B) may be, for example, a primary or secondary alcohol ethoxylate, especially a $C_8$-$C_{20}$ aliphatic alcohol ethoxylated with an average of from 1 to 20 mol of ethylene oxide per alcohol group. Preference is given to primary and secondary $C_{10}$-$C_{15}$ aliphatic alcohols ethoxylated with an average of from 1 to 10 mol of ethylene oxide per alcohol group. Non-ethoxylated non-ionic surfactants, for example alkylpolyglycosides, glycerol monoethers and polyhydroxyamides (glucamide), may likewise be used.

The total amount of anionic and non-ionic surfactants is preferably from 3 to 50 wt-%, especially from 5 to 40 wt-% and more especially from 5 to 30 wt-%. The lower limit of those surfactants to which even greater preference is given is 5 wt-%.

As builder substance C) there come into consideration, for example, alkali metal phosphates, especially tripolyphosphates, carbonates and hydrogen carbonates, especially their sodium salts, silicates, aluminum silicates, polycarboxylates, polycarboxylic acids, organic phosphonates, aminoalkylenepoly(alkylenephosphonates) and mixtures of such compounds.

Silicates that are especially suitable are sodium salts of crystalline layered silicates of the formula NaHSi$_t$O$_{2t+1}$·pH$_2$O or Na$_2$Si$_t$O$_{2t+1}$·pH$_2$O wherein t is a number from 1.9 to 4 and p is a number from 0 to 20.

Among the aluminum silicates, preference is given to those commercially available under the names zeolite A, B, X and HS, and also to mixtures comprising two or more of such components. Special preference is given to zeolite A.

Among the polycarboxylates, preference is given to polyhydroxycarboxylates, especially citrates, and acrylates, and also to copolymers thereof with maleic anhydride. Preferred polycarboxylic acids are nitrilotriacetic acid, ethylenediaminetetraacetic acid and ethylenediamine disuccinate either in racemic form or in the enantiomerically pure (S,S) form.

Biodegradable options are, for example, aminoacid acetates, such as Trilon M (BASF) and Dissolvine GL (AKZO), as well as asparaginic acid derivatives, such as Baypure CX (Lanxess).

Phosphonates or aminoalkylenepoly(alkylenephosphonates) that are especially suitable are alkali metal salts of 1-hydroxyethane-1,1-diphosphonic acid, nitrilotris(methylenephosphonic acid), ethylenediaminetetramethylenephosphonic acid and diethylenetriaminepentamethylenephosphonic acid, and also salts thereof. Also preferred polyphosphonates have the following formula

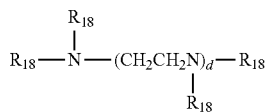

wherein $R_{18}$ is CH$_2$PO$_3$H$_2$ or a water soluble salt thereof and d is an integer of the value 0, 1, 2 or 3.

Especially preferred are the polyphosphonates wherein d is an integer of the value of 1.

The compositions may comprise, in addition to the combination according to the invention, one or more optical brighteners, for example from the classes bis-triazinylamino-stilbenedisulfonic acid, bis-triazolyl-stilbenedisulfonic acid, bis-styryl-biphenyl or bis-benzofuranylbiphenyl, α bis-benzoxalyl derivative, bis-benzimidazolyl derivative or coumarin derivative or a pyrazoline derivative.

The compositions may furthermore comprise one or more further additives. Such additives are, for example, dirt-suspending agents, for example sodium carboxymethylcellulose; pH regulators, for example alkali metal or alkaline earth metal silicates; foam regulators, for example soap; salts for adjusting the spray drying and the granulating properties, for example sodium sulfate; perfumes; and also, if appropriate, antistatics and softening agents such as, for example, smectite; bleaching agents; pigments; and/or toning agents. These constituents should especially be stable to any bleaching agent employed.

If the detergent composition is used in an automatic dishwasher it is also common to use silver-corrosion inhibitors.

Such auxiliaries are added in a total amount of from 0.1-20 wt-%, preferably from 0.5-10 wt-%, especially from 0.5-5 wt-%, based on the total weight of the detergent formulation.

Furthermore, the detergent may optionally also comprise enzymes. Enzymes can be added for the purpose of stain removal. The enzymes usually improve the action on stains caused by protein or starch, such as, for example, blood, milk, grass or fruit juices. Preferred enzymes are cellulases and proteases, especially proteases. Cellulases are enzymes that react with cellulose and its derivatives and hydrolyse them to form glucose, cellobiose and cellooligosaccharides. Cellulases remove dirt and, in addition, have the effect of enhancing the soft handle of the fabric.

Examples of customary enzymes include, but are by no means limited to, the following:

proteases as described in U.S. Pat. No. 6,242,405, column 14, lines 21 to 32;

lipases as described in U.S. Pat. No. 6,242,405, column 14, lines 33 to 46;

amylases as described in U.S. Pat. No. 6,242,405, column 14, lines 47 to 56; and cellulases as described in U.S. Pat. No. 6,242,405, column 14, lines 57 to 64.

Commercially available detergent proteases, such as Alcalase®, Esperase®, Everlase®, Savinase®, Kannase® and Durazym®, are sold e.g. by NOVOZYMES A/S.

Commercially available detergent amylases, such as Termamyl®, Duramyl®, Stainzyme®, Natalase®, Ban® and Fungamyl®, are sold e.g. by NOVOZYMES A/S.

Commercially available detergent cellulases, such as Celluzyme®, Carezyme® and Endolase®, are sold e.g. by NOVOZYMES A/S.

Commercially available detergent lipases, such as Lipolase®, Lipolase Ultra® and Lipoprime®, are sold e.g. by NOVOZYMES A/S.

Suitable mannanases, such as Mannanaway®, are sold by NOVOZYMES A/S.

Beside in laundry care products, in a dishwashing detergents, especially in a composition used in automatic dishwashers the following enzymes are also commonly used:

proteases, amylases, pullulanases, cutinases and lipases, for example proteases such as BLAP®, Optimase®, Opticlean®, Maxacal®, Maxapem®, Esperase® and/or Savinase®, amylases such as Termamyl®, Amylase-LT®, Maxamyl® and/or Duramyl®, lipases such as Lipolase®, Lipomax®, Lumafast® and/or Lipozym®. The enzymes which may be used can, as described e.g. in International Patent Applications WO 92/11347 and WO 94/23005, be adsorbed on carriers and/or embedded in encapsulating substances in order to safeguard them against premature inactivation. They are present in the cleaning formulations according to the invention preferably in amounts not exceeding 5 wt-%, especially in amounts of from 0.1 wt-% to 1.2 wt-%.

Amylases: The present invention preferably makes use of amylases having improved stability in detergents, especially improved oxidative stability. Such amylases are non-limitingly illustrated by the following: (a) An amylase according to WO 94/02597, Novo Nordisk A/S, published Feb. 3, 1994, as further illustrated by a mutant in which substitution is made, using alanine or threonine (preferably threonine), of the methionine residue located in position 197 of the *B. licheniformis* alpha-amylase, known as TERMAMYL®, or the homologous position variation of a similar parent amylase, such as *B. amyloliquefaciens, B. subtilis,* or *B. stearothermophilus*; (b) Stability-enhanced amylases as described by Genencor International in a paper entitled "Oxidatively Resistant alpha-Amylases" presented at the 207th American Chemical Society National Meeting, Mar. 13-17, 1994, by C. Mitchinson. Therein it was noted that bleaches in automatic dishwashing detergents inactivate alpha-amylases but that improved oxidative stability amylases have been made by Genencor from *B. licheniformis* NCIB8061. Any other oxidative stability-enhanced amylase can be used.

Proteases: Protease enzymes are usually present in preferred embodiments of the invention at levels between 0.001 wt-% and 5 wt-%. The proteolytic enzyme can be of animal, vegetable or microorganism (preferred) origin. More preferred is serine proteolytic enzyme of bacterial origin. Purified or nonpurified forms of enzyme may be used. Proteolytic enzymes produced by chemically or genetically modified mutants are included by definition, as are close structural enzyme variants. Suitable commercial proteolytic enzymes include Alcalase®, Esperase®, Durazyme®, Savinase®, Maxatase®, Maxacal®, and Maxapem® 15 (protein engineered Maxacal). Purafect® and subtilisin BPN and BPN' are also commercially available.

When present, lipases comprise from about 0.001 wt-% to about 0.01 wt-% of the instant compositions and are optionally combined with from about 1 wt-% to about 5 wt-% of a surfactant having limesoap-dispersing properties, such as an alkyldimethylamine N-oxide or a sulfobetaine. Suitable lipases for use herein include those of bacterial, animal and fungal origin, including those from chemically or genetically modified mutants.

When incorporating lipases into the instant compositions, their stability and effectiveness may in certain instances be enhanced by combining them with small amounts (e.g., less than 0.5 wt-% of the composition) of oily but non-hydrolyzing materials.

The enzymes, when used, may be present in a total amount of from 0.01 to 5 wt-%, especially from 0.05 to 5 wt-% and more especially from 0.1 to 4 wt-%, based on the total weight of the detergent formulation.

If the detergent formulation is a dishwashing detergent formulation, more preferably an automatic dishwashing detergent formulation, then it can optionally also comprise from about 0.001 wt-% to about 10 wt-%, preferably from about 0.005 wt-% to about 8 wt-%, most preferably from about 0.01 wt-% to about 6 wt-% of an enzyme stabilizing system. The enzyme stabilizing system can be any stabilizing system which is compatible with the detersive enzyme. Such a system may be inherently provided by other formulation actives, or be added separately, e.g., by the formulator or by a manufacturer of detergent-ready enzymes. Such stabilizing systems can, for example, comprise calcium ion, boric acid, propylene glycol, short chain carboxylic acids, boronic acids, and mixtures thereof, and are designed to address different stabilization problems depending on the type and physical form of the detergent composition.

In order to enhance the bleaching action, the compositions may, in addition to comprising the catalysts described herein, also comprise photocatalysts the action of which is based on the generation of singlet oxygen.

Further preferred additives to the compositions according to the invention are dye-fixing agents and/or polymers which, during the washing of textiles, prevent staining caused by dyes in the washing liquor that have been released from the textiles under the washing conditions. Such polymers are preferably polyvinylpyrrolidones, polyvinylimidazoles or polyvinylpyridine-N-oxides, which may have been modified by the incorporation of anionic or cationic substituents, especially those having a molecular weight in the range of from 5000 to 60 000, more especially from 10 000 to 50 000. Such polymers are usually used in a total amount of from 0.01 to 5 wt-%, especially from 0.05 to 5 wt-%, more especially from 0.1 to 2 wt-%, based on the total weight of the detergent formulation. Preferred polymers are those mentioned in WO-A-02/02865 (see especially page 1, last paragraph and page 2, first paragraph) and those in WO-A-04/05688.

When the inventive detergent composition is used as hardsurface cleaner, especially when the composition is used in automatic dishwasher formulation then, it has been found out, that it is preferable to avoid the use of simple calcium-precipitating soaps as antifoams in the present compositions as they tend to deposit on the dishware. Indeed, phosphate esters are not entirely free of such problems and the formulator will generally choose to minimize the content of potentially depositing antifoams in the instant compositions.

Other examples for foam suppressors are paraffin, paraffin/alcohol combinations, or bisfatty acid amides.

The dishwashing detergent formulations, more preferably automatic dishwashing detergent formulations herein may also optionally contain one or more heavy metal chelating agents, such as hydroxyethyldiphosphonate (HEDP). More generally, chelating agents suitable for use herein can be selected from the group consisting of amino carboxylates, amino phosphonates, polyfunctionally-substituted aromatic chelating agents and mixtures thereof. Other suitable chelating agents for use herein are the commercial DEQUEST series, and chelants from Nalco, Inc.

Aminocarboxylates useful as optional chelating agents include ethylenediaminetetracetates, N-hydroxyethylethylenediaminetriacetates, nitrilotriacetates, ethylenediamine tetraprorionates, triethylenetetraaminehexacetates, diethylenetriamine-pentaacetates, and ethanoldiglycines, alkali metal, ammonium, and substituted ammonium salts thereof and mixtures thereof.

Aminophosphonates are also suitable for use as chelating agents in the compositions of the invention when at least low levels of total phosphorus are permitted in detergent compositions, and include ethylenediaminetetrakis(methylenephosphonates).

Further biodegradable sequestrants are, for example, aminoacid acetates, such as Trilon M (BASF) and Dissolvine GL (AKZO), as well as asparaginic acid derivatives, such as Baypure CX.

Preferably, the aminophosphonates do not contain alkyl or alkenyl groups with more than about 6 carbon atoms.

A highly preferred biodegradable chelator for use herein is ethylenediamine disuccinate ("EDDS").

If utilized, these chelating agents or transition-metal selective sequestrants will generally comprise from about 0.001 wt-% to about 10 wt-%, more preferably from about 0.05 wt-% to about 1 wt-% of the dishwashing detergent formulations, more preferably automatic dishwashing detergent formulations herein.

Preferred dishwashing detergent formulations, more preferably automatic dishwashing detergent formulations herein may additionally contain a dispersant polymer. When present, a dispersant polymer is typically at levels in the range from 0 wt-% to about 25 wt-%, preferably from about 0.5 wt-% to about 20 wt-%, more preferably from about 1 wt-% to about 8 wt-% of the detergent composition. Dispersant polymers are useful for improved filming performance of the present dishwasher detergent compositions, especially in higher pH embodiments, such as those in which wash pH exceeds about 9.5. Particularly preferred are polymers, which inhibit the deposition of calcium carbonate or magnesium silicate on dishware.

Suitable polymers are preferably at least partially neutralized or alkali metal, ammonium or substituted ammonium (e.g., mono-, di- or triethanolammonium) salts of polycarboxylic acids. The alkali metal, especially sodium salts are most preferred. While the molecular weight of the polymer can vary over a wide range, it preferably is from about 1,000 to about 500,000, more preferably is from about 1,000 to about 250,000.

Unsaturated monomeric acids that can be polymerized to form suitable dispersant polymers include acrylic acid, maleic acid (or maleic anhydride), fumaric acid, itaconic acid, aconitic acid, mesaconic acid, citraconic acid and methylenemalonic acid. The presence of monomeric segments containing no carboxylate radicals such as methyl vinyl ether, styrene, ethylene, etc. is suitable provided that such segments do not constitute more than about 50 wt-% of the dispersant polymer.

Copolymers of acrylamide and acrylate having a molecular weight of from about 3,000 to about 100,000, preferably from about 4,000 to about 20,000, and an acrylamide content of less than about 50 wt-%, preferably less than about 20 wt-% of the dispersant polymer can also be used. Most preferably, such dispersant polymer has a molecular weight of from about 4,000 to about 20,000 and an acrylamide content of from about 0 wt-% to about 15 wt-%, based on the total weight of the polymer.

Particularly preferred dispersant polymers are low molecular weight modified polyacrylate copolymers. Such copolymers contain as monomer units: a) from about 90 wt-% to about 10 wt-%, preferably from about 80 wt-% to about 20 wt-% acrylic acid or its salts and b) from about 10 wt-% to about 90 wt-%, preferably from about 20 wt-% to about 80 wt-% of a substituted acrylic monomer or its salt and have the general formula: —[(C(R$_a$)C(R$_b$)(C(O)OR$_c$)] wherein the apparently unfilled valencies are in fact occupied by hydrogen and at least one of the substituents R$_a$, R$_b$, or R$_c$, preferably R$_a$ or R$_b$, is a 1 to 4 carbon alkyl or hydroxyalkyl group; R$_a$ or R$_b$ can be a hydrogen and R$_c$ can be a hydrogen or alkali metal salt. Most preferred is a substituted acrylic monomer wherein R$_a$ is methyl, R$_b$ is hydrogen, and R$_c$ is sodium.

A suitable low molecular weight polyacrylate dispersant polymer preferably has a molecular weight of less than about 15,000, preferably from about 500 to about 10,000, most preferably from about 1,000 to about 5,000. The most preferred polyacrylate copolymer for use herein has a molecular weight of about 3,500 and is the fully neutralized form of the polymer comprising about 70 wt-% acrylic acid and about 30 wt-% methacrylic acid.

Other dispersant polymers useful herein include the polyethylene glycols and polypropylene glycols having a molecular weight of from about 950 to about 30,000.

Yet other dispersant polymers useful herein include the cellulose sulfate esters such as cellulose acetate sulfate, cellulose sulfate, hydroxyethyl cellulose sulfate, methylcellulose sulfate, and hydroxypropylcellulose sulfate. Sodium cellulose sulfate is the most preferred polymer of this group.

Other suitable dispersant polymers are the carboxylated polysaccharides, particularly starches, celluloses and alginates.

Yet another group of acceptable dispersants are the organic dispersant polymers, such as polyaspartate.

Depending on whether a greater or lesser degree of compactness is required, filler materials can also be present in the instant dishwashing detergent formulations, more preferably automatic dishwashing detergent formulations. These include sucrose, sucrose esters, sodium sulfate, potassium sulfate, etc., in amounts up to about 70 wt-%, preferably from 0 wt-% to about 40 wt-% of the dishwashing detergent formulations, more preferably automatic dishwashing detergent formulations. Preferred filler is sodium sulfate, especially in good grades having at most low levels of trace impurities.

Sodium sulfate used herein preferably has a purity sufficient to ensure it is non-reactive with bleach; it may also be treated with low levels of sequestrants, such as phosphonates or EDDS in magnesium-salt form. Note that preferences, in terms of purity sufficient to avoid decomposing bleach, applies also to pH-adjusting component ingredients, specifically including any silicates used herein.

Organic solvents that can be used in the cleaning formulations according to the invention, especially when the latter are in liquid or paste form, include alcohols having from 1 to 4 carbon atoms, especially methanol, ethanol, isopropanol and tert-butanol, diols having from 2 to 4 carbon atoms, especially ethylene glycol and propylene glycol, and mixtures thereof, and the ethers derivable from the mentioned classes of compound. Such water-miscible solvents are present in the cleaning formulations according to the invention preferably in amounts not exceeding 20 wt-%, especially in amounts of from 1 wt-% to 15 wt-%.

Many dishwashing detergent formulations, more preferably automatic dishwashing detergent formulations herein will be buffered, i.e., they are relatively resistant to pH drop in the presence of acidic soils. However, other compositions herein may have exceptionally low buffering capacity, or may be substantially unbuffered. Techniques for controlling or varying pH at recommended usage levels more generally include the use of not only buffers, but also additional alkalis, acids, pH-jump systems, dual compartment containers, etc., and are well known to those skilled in the art.

Certain dishwashing detergent formulations, more preferably automatic dishwashing detergent formulations, comprise a pH-adjusting component selected from water-soluble alkaline inorganic salts and water-soluble organic or inorganic builders. The pH-adjusting components are selected so that when the dishwashing detergent formulation, more preferably automatic dishwashing detergent formulation is dissolved in water at a concentration of 1,000-5,000 ppm, the pH remains in the range of above about 8, preferably from about 9.5 to about 11. The preferred nonphosphate pH-adjusting component can be selected from the group consisting of:
(i) sodium carbonate or sesquicarbonate;
(ii) sodium silicate, preferably hydrous sodium silicate having $SiO_2:Na_2O$ ratio of from about 1:1 to about 2:1, and mixtures thereof with limited quantities of sodium metasilicate;
(iii) sodium citrate;
(iv) citric acid;
(v) sodium bicarbonate;
(vi) sodium borate, preferably borax;
(vii) sodium hydroxide; and
(viii) mixtures of (i)-(vii).

Preferred embodiments contain low levels of silicate (i.e. from about 3 wt-% to about 10 wt-% $SiO_2$).

Illustrative of highly preferred pH-adjusting component systems of this specialized type are binary mixtures of granular sodium citrate with anhydrous sodium carbonate, and three-component mixtures of granular sodium citrate trihydrate, citric acid monohydrate and anhydrous sodium carbonate.

The amount of the pH adjusting component in compositions used for automatic dishwashing is preferably from about 1 wt-% to about 50 wt-% of the composition. In a preferred embodiment, the pH-adjusting component is present in the composition in an amount from about 5 wt-% to about 40 wt-%, preferably from about 10 wt-% to about 30 wt-%.

For compositions herein having a pH between about 9.5 and about 11 of the initial wash solution, particularly preferred automatic dishwashing detergent formulations embodiments comprise, by weight of the automatic dishwashing detergent formulations, from about 5 wt-% to about 40 wt-%, preferably from about 10 wt-% to about 30 wt-%, most preferably from about 15 wt-% to about 20 wt-%, of sodium citrate with from about 5 wt-% to about 30 wt-%, preferably from about 7 wt-% to 25 wt-%, most preferably from about 8 wt-% to about 20 wt-% sodium carbonate.

The essential pH-adjusting system can be complemented (i.e. for improved sequestration in hard water) by other optional detergency builder salts selected from nonphosphate detergency builders known in the art, which include the various water-soluble, alkali metal, ammonium or substituted ammonium borates, hydroxysulfonates, polyacetates, and polycarboxylates. Preferred are the alkali metals, especially sodium, salts of such materials. Alternate water-soluble, non-phosphorus organic builders can be used for their sequestering properties. Examples of polyacetate and polycarboxylate builders are the sodium, potassium, lithium, ammonium and substituted ammonium salts of ethylenediamine tetraacetic acid; nitrilotriacetic acid, tartrate monosuccinic acid, tartrate disuccinic acid, oxydisuccinic acid, carboxymethoxysuccinic acid, mellitic acid, and sodium benzene polycarboxylate salts. Further biodegradable buildes are, for example, aminoacid acetates, such as Trilon M (BASF) and Dissolvine GL (AKZO), as well as asparaginic acid derivatives, such as Baypure CX.

The detergent formulations can take a variety of physical forms such as, for example, powder granules, tablets (tabs), gel and liquid. Examples thereof include, inter alia, conventional high-performance detergent powders, supercompact high-performance detergent powders and tabs. One important physical form is the so-called concentrated granular form, which is added to a washing machine.

Also of importance are so-called compact or supercompact detergents. In the field of detergent manufacture, there is a trend towards the production of such detergents that contain an increased amount of active substances. In order to minimize energy consumption during the washing procedure, compact or supercompact detergents need to act effectively at low washing temperatures, for example below 40° C., or even at room temperature (25° C.). Such detergents usually contain only small amounts of fillers or of substances, such as sodium sulfate or sodium chloride, required for detergent manufacture. The total amount of such substances is usually from 0 to 10 wt-%, especially from 0 to 5 wt-%, more especially from 0 to 1 wt-%, based on the total weight of the detergent formulation. Such (super)compact detergents usually have a bulk density of from 650 to 1000 g/l, especially from 700 to 1000 g/l and more especially from 750 to 1000 g/l.

The detergent formulations can also be in the form of tablets (tabs). The advantages of tabs reside in the ease of dispensing and convenience in handling. Tabs are the most compact form of solid detergent formulation and usually have a volumetric density of, for example, from 0.9 to 1.3 kg/liter. To achieve rapid dissolution, such tabs generally contain special dissolution aids:
  carbonate/hydrogen carbonate/citric acid as effervescents;
  disintegrators, such as cellulose, carboxymethyl cellulose or cross-linked poly(N-vinylpyrrolidone);
  rapidly dissolving materials, such as sodium (potassium) acetates, or sodium (potassium) citrates;
  rapidly dissolving, water-soluble, rigid coating agents, such as dicarboxylic acids.

The tabs may also comprise combinations of such dissolution aids.

The detergent formulation may also be in the form of an aqueous liquid containing from 5 wt-% to 50 wt-%, preferably from 10 wt-% to 35 wt-%, of water or in the form of a non-aqueous liquid containing no more than 5 wt-%, preferably from 0 wt-% to 1 wt-% of water. Non-aqueous liquid detergent formulations may comprise other solvents as carriers. Low molecular weight primary or secondary alcohols, for example methanol, ethanol, propanol and isopropanol, are suitable for that purpose. The solubilising surfactant used is preferably a monohydroxy alcohol but polyols, such as those containing from 2 to 6 carbon atoms and from 2 to 6 hydroxy groups (e.g., 1,3-propanediol, ethylene glycol, glycerol and 1,2-propanediol) can also be used. Such carriers are usually used in a total amount of from 5 wt-% to 90 wt-%, preferably from 10 wt-% to 50 wt-%, based on the total weight of the detergent formulation. The detergent formulations can also used in so-called "unit liquid dose" form.

Also an aspect of the invention is a granule comprising
  a) from 1-99 wt-%, based on the total weight of the granule, of a composition as described in claim 1;
  b) from 1-99 wt-%, based on the total weight of the granule, of at least one binder,
  c) from 0-20 wt-%, based on the total weight of the granule, of at least one encapsulating material,
  d) from 0-20 wt-%, based on the total weight of the granule, of at least one further additive and
  e) from 0-20 wt-% based on the total weight of the granule, of water; the sum of the percentage being 100%.

The granules according to the invention comprise a water-soluble organic polymer as binder. Such polymers may be used singly or in the form of mixtures of two or more polymers.

Water-soluble polymers that come into consideration are, for example, polyethylene glycols, copolymers of ethylene oxide with propylene oxide, gelatin, polyacrylates, polymethacrylates, polyvinylpyrrolidones, vinylpyrrolidones, vinyl acetates, polyvinylimidazoles, polyvinylpyridine-N-oxides, copolymers of vinylpyrrolidone with long-chain α-olefins, copolymers of vinylpyrrolidone with vinylimidazole, poly(vinylpyrrolidone/dimethylaminoethyl methacrylates), copolymers of vinylpyrrolidone/dimethylaminopropyl methacrylamides, copolymers of vinylpyrrolidone/dimethylaminopropyl acrylamides, quaternised copolymers of vinylpyrrolidones and dimethylaminoethyl methacrylates, terpolymers of vinylcaprolactam/vinylpyrrolidone/dimethylaminoethyl methacrylates, copolymers of vinylpyrrolidone and methacrylamidopropyl-trimethylammonium chloride, terpolymers of caprolactam/vinylpyrrolidone/dimethylaminoethyl methacrylates, copolymers of styrene and acrylic acid, polycarboxylic acids, polyacrylamides, carboxymethyl cellulose, hydroxymethyl cellulose, polyvinyl alcohols, polyvinyl acetate, hydrolysed polyvinyl acetate, copolymers of ethyl acrylate with methacrylate and methacrylic acid, copolymers of maleic acid with unsaturated hydrocarbons, and also mixed polymerisation products of the mentioned polymers.

Of those organic polymers, special preference is given to polyethylene glycols, carboxymethyl cellulose, polyacrylamides, polyvinyl alcohols, polyvinylpyrrolidones, gelatin, hydrolysed polyvinyl acetates, copolymers of vinylpyrrolidone and vinyl acetate, and also polyacrylates, copolymers of ethyl acrylate with methacrylate and methacrylic acid, and polymathacrylates.

Encapsulating materials include especially water-soluble and water-dispersible polymers and waxes. Of those materials, preference is given to polyethylene glycols, polyamides, polyacrylamides, polyvinyl alcohols, polyvinylpyrrolidones, gelatin, hydrolysed polyvinyl acetates, copolymers of vinylpyrrolidone and vinyl acetate, and also polyacrylates, paraffins, fatty acids, copolymers of ethyl acrylate with methacrylate and methacrylic acid, and polymethacrylates.

Further additives (d) that come into consideration are, for example, wetting agents, dust removers, water-insoluble or water-soluble dyes or pigments, and also dissolution accelerators, optical brighteners and sequestering agents. Examples have already been given above.

The compounds of formula 1 and 2 are partially new. Novel compounds are those which are ionic, i.e. the compound carries a positive or negative charge which is balanced by a counter ion.

Therefore, another aspect is a compound of formula (1a) or (2a)

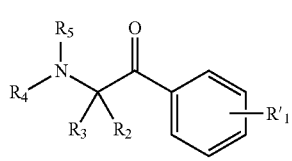

(1a)

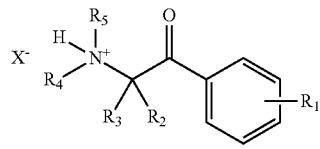

(2a)

wherein $X^-$ is the anion of an organic or inorganic acid;

$R_1$ is hydrogen, halogen, phenyl, phenoxy, phenylthio, phenyl-(SO)—, linear or branched $C_1$-$C_6$alkyl, $C_1$-$C_6$alkoxy, $C_1$-$C_6$alkylthio, $C_1$-$C_6$alkyl-SO$_2$—, which $C_1$-$C_6$alkyl is unsubstituted or substituted by OH or (CO)OR$_6$;

or $R_1$ is linear or branched $C_2$-$C_3$alkenyl which is unsubstituted or substituted by (CO)OR$_6$;

or $R_1$ is $S^+(R_7)(R_8)X'^-$;

$R_7$ and $R_8$ independently of each other are linear or branched $C_1$-$C_6$ alkyl;

or $R_7$ or $R_8$ is linear or branched $C_2$-$C_3$ alkenyl;

$X'^-$ has one of the definitions given for $X^-$ and is same or different;

or $R_1$ is $N^+(R_9)(R_{10})(R_{11})X''^-$;

$R_9$, $R_{10}$ and $R_{11}$ independently of each other are linear or branched $C_1$-$C_6$alkyl;

or $R_7$ or $R_8$ or $R_{11}$ is linear or branched $C_2$-$C_3$ alkenyl;

or $R_9$ and $R_{10}$ or $R_9$ and $R_{11}$ or $R_{10}$ and $R_{11}$ together with the Nitrogen atom to which they are bonded form a pyrrolidine, piperidine or morpholine group;

$X''^-$ has one of the definitions given for $X^-$ and $X'^-$ and is same or different;

$R'_1$ is linear or branched $C_1$-$C_6$alkyl, $C_1$-$C_6$alkoxy, $C_1$-$C_6$alkylthio, $C_1$-$C_6$alkyl-S(O)—, $C_1$-$C_6$alkyl-SO$_2$— which $C_1$-$C_6$alkyl is substituted by (CO)O$^-$Z$^+$;

or $R'_1$ is linear or branched $C_2$-$C_3$alkenyl substituted by (CO)O$^-$Z$^+$;

or $R'_1$ is $S+(R_7)(R_8)$ $X'^-$;

$R_7$ and $R_8$ independently of each other are linear or branched $C_1$-$C_6$ alkyl;

or $R_7$ or $R_8$ is linear or branched $C_2$-$C_3$ alkenyl;

$X'^-$ has one of the definitions given for $X^-$ and is same or different;

or $R'_1$ is $N^+(R_9)(R_{10})(R_{11})X''^-$;

$R_9$, $R_{10}$ and $R_{11}$ independently of each other are linear or branched $C_1$-$C_6$alkyl;

or $R_7$ or $R_8$ or $R_{11}$ is linear or branched $C_2$-$C_3$ alkenyl;

or $R_9$ and $R_{10}$ or $R_9$ and $R_{11}$ or $R_{10}$ and $R_{11}$ together with the Nitrogen atom to which they are bonded form a pyrrolidine, piperidine or morpholine group;

$X''^-$ has one of the definitions given for $X^-$ and $X'^-$ and is same or different;

$R_2$ and $R_3$ independently of each other are hydrogen, linear or branched $C_1$-$C_6$alkyl which is unsubstituted or substituted by phenyl; or linear or branched $C_2$-$C_3$alkenyl;

or $R_2$ and $R_3$, together with the atom to which they are bonded form a cyclopentyl or cyclohexyl group;

$R_4$ and $R_5$ independently of each other are hydrogen, linear or branched $C_1$-$C_{12}$alkyl which is unsubstituted or substituted by 1 to 4 OH groups; unsubstituted $C_2$-$C_6$alkenyl, $C_1$-$C_6$alkyl which is interrupted by one or more O or $C_5$-$C_8$cycloalkyl;

or $R_4$ and $R_5$ together with the Nitrogen atom to which they are bonded form a pyrrolidine, piperidine or morpholine group or hexamethyleneimine;

$R_6$ is hydrogen or linear or branched $C_1$-$C_3$alkyl;

$Z^+$ is $Na^+$, $K^+$ or $NH_4^+$;

with the proviso that if in formulae (1) and (2) $R_1$, $R_2$ and $R_3$ are hydrogen, $R_4$ and $R_5$ are not unsubstituted $C_1$-$C_{12}$alkyl or unsubstituted $C_2$-$C_6$alkenyl.

In a specific embodiment the compound is of formulae (1a) and (2a)

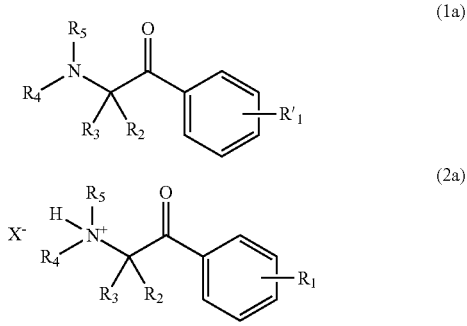

wherein $X^-$ is the anion of an organic or inorganic acid;

$R_1$ is hydrogen, halogen, phenyl, phenoxy, phenylthio, phenyl-(SO)—, linear or branched $C_1$-$C_6$alkyl, $C_1$-$C_6$alkoxy, $C_1$-$C_6$alkylthio, $C_1$-$C_6$alkyl-S(O)—, $C_1$-$C_6$alkyl-SO$_2$—, which $C_1$-$C_6$alkyl is unsubstituted or substituted by OH or (CO)OR$_6$;

or $R_1$ is linear or branched $C_2$-$C_3$alkenyl which is unsubstituted or substituted by (CO)OR$_6$;

$R'_1$ is linear or branched $C_1$-$C_6$alkyl, $C_1$-$C_6$alkoxy, $C_1$-$C_6$alkylthio, $C_1$-$C_6$alkyl-S(O)—, $C_1$-$C_6$alkyl-SO$_2$— which $C_1$-$C_6$alkyl is substituted by (CO)O$^-$Z$^+$;

or $R'_1$ is linear or branched $C_2$-$C_3$alkenyl substituted by (CO)O$^-$Z$^+$;

$R_2$ and $R_3$ independently of each other are hydrogen, linear or branched $C_1$-$C_6$alkyl which is unsubstituted or substituted by phenyl; or linear or branched $C_2$-$C_3$alkenyl;

or $R_2$ and $R_3$, together with the atom to which they are bonded form a cyclopentyl or cyclohexyl group;

$R_4$ and $R_5$ independently of each other are hydrogen, linear or branched $C_1$-$C_{12}$alkyl which is unsubstituted or substituted by 1 to 4 OH groups; unsubstituted $C_2$-$C_6$alkenyl, $C_1$-$C_6$alkyl which is interrupted by one or more O or $C_5$-$C_8$cycloalkyl;

or $R_4$ and $R_5$ together with the Nitrogen atom to which they are bonded form a pyrrolidine, piperidine or morpholine group or hexamethyleneimine;

$R_6$ is hydrogen or linear or branched $C_1$-$C_3$alkyl;

$Z^+$ is $Na^+$, $K^+$ or $NH_4^+$; with the proviso that if in formulae (1) and (2) $R_1$, $R'_1$, $R_2$ and $R_3$ are hydrogen, $R_4$ and $R_5$ are not unsubstituted $C_1$-$C_{12}$alkyl or unsubstituted $C_2$-$C_6$alkenyl.

Preferred are compounds of formula (2a) as defined above.

Definitions and preferences given above apply equally for all aspects of the invention.

The following examples illustrate the invention.

PREPARATION EXAMPLES

Compound 1

2-Methyl-1-(4-methylsulfanylphenyl)-2-morpholino-propan-1-one: The title compound is commercially available under the trade name Irgacure 907 [CAS 71868-10-5].

$^1$H-NMR (300 MHz, CDCl$_3$), δ [ppm]: 1.31 (s, 6H), 2.53 (s, 3H), 2.56-2.59 (m, 4H), 3.68-3.71 (m, 4H), 7.21-7.24 (m, d-like, 2H), 8.50-8.53 (m, d-like, 2H).

Compound 2

2-Methyl-1-(4-methylsulfanylphenyl)-2-morpholin-4-ium-4-yl-propan-1-one tetrafluoroborate: Tetrafluoroboric acid (54% in diethyl ether; 1.47 g, 9 mmol) is slowly added to an ice-cooled solution of 2-methyl-1-(4-methylsulfanyl-phenyl)-2-morpholino-propan-1-one (2.29 g, 8.2 mmol) in diethyl ether (65 ml). The resulting suspension is stirred for two hours and then filtered. The filter cake is washed with diethyl ether and dried to afford the title compound as a white solid (3 g).

$^1$H-NMR (300 MHz, CD$_3$OD), δ [ppm]: 1.75 (broad s, 6H), 2.46 (s, 3H), 3.21 (broad s, 4H), 3.85 (broad s, 2H), 4.00 (broad s, 2H), 7.27-7.29 (m, d-like, 2H), 7.86 (broad s, 2H).

Compound 3

2-Methyl-1-(4-methylsulfanylphenyl)-2-morpholin-4-ium-4-yl-propan-1-one chloride: Hydrochloric acid (32% in water; 0.57 g, 5 mmol) is added to a warm solution of 2-methyl-1-(4-methylsulfanylphenyl)-2-morpholino-propan-1-one (1.4 g, 5 mmol) in n-propanol (15 ml). The resulting mixture is stirred one hour and then concentrated on a rotary evaporator to afford the title compound as a white solid (1.58 g).

$^1$H-NMR (300 MHz, DMSO-d$_6$), δ [ppm]: 1.83 (broad s, 6H), 2.55 (s, 3H), 3.33 (broad s, 4H), 4.01 (broad s, 4H), 7.36-7.39 (m, d-like, 2H), 7.90 (broad s, 2H), 10.73 (broad s, 1H).

Compound 4

1-(4-Butylsulfanylphenyl)-2-methyl-2-morpholino-propan-1-one: The title compound is synthesized according to the published procedure (EP 88050 A2).

$^1$H-NMR (300 MHz, CDCl$_3$), δ [ppm]: 0.97 (t, J=7.35 Hz; 3H), 1.32 (s, 6H), 1.46-1.55 (m, 2H), 1.68-1.75 (m, 2H), 2.57-2.60 (m, 4H), 3.00-3.03 (m, t-like, 2H), 3.69-3.72 (m, 4H), 7.25-7.27 (m, d-like, 2H), 8.49-8.51 (m, d-like, 2H).

GLC/MS (pos. CI), m/z (%): found 322.12 (100); calcd. for $C_{18}H_{27}NO_2S$: 321.

Compound 5

2-Methyl-1-(4-methylsulfinylphenyl)-2-morpholino-propan-1-one: 3-Chloroper-oxybenzoic acid (70%; 0.84 g, 3.41 mmol), dissolved in dichloromethane (10 ml), is slowly added to an ice-cooled solution of 2-methyl-1-(4-methylsulfanylphenyl)-2-morpholino-propan-1-one (0.95 g, 3.4 mmol) in dichloromethane (10 ml). The reaction mixture is stirred for 2.5 hours and then filtered. The filtrate is washed with sodium hydroxide (2 mol/L in water), the organic phase separated off and the solvent evaporated on a rotary evaporator to afford the title compound as slightly yellow oil which solidified upon storage in a refrigerator (1.06 g).

$^1$H-NMR (300 MHz, CDCl$_3$), δ [ppm]: 1.33 (s, 6H), 2.57-2.60 (m, 4H), 2.77 (s, 3H), 3.68-3.71 (m, 4H), 7.68-7.71 (m, d-like, 2H), 8.68-8.71 (m, d-like, 2H).

LC/MS (pos. APCI), m/z (area %): found 296.0 (99); calcd. for $C_{15}H_{21}NO_3S$: 295.

Compound 6

2-Methyl-1-(4-methylsulfonylphenyl)-2-morpholino-propan-1-one: 1-(4-Fluoro-phenyl)-2-methyl-2-morpholin-4-yl-propan-1-one (prepared according to DE19753655; 5 g, 19.9 mmol) is dissolved in DMSO (25 ml) followed by the addition of sodium methanesulfinate (12.08 g, 118.3 mmol). The reaction mixture is brought to 140° C. and stirred for 30 hours, affording an orange suspension. The mixture is poured on toluene/water, the organic phase separated off, washed with water, dried over magnesium sulfate and the solvent evaporated under reduced pressure to yield a solid (5.5 g). Re-crystallization from methanol afforded the title compound (4.4 g).

$^1$H-NMR (300 MHz, CDCl$_3$), δ [ppm]: 1.33 (s, 6H), 2.57-2.60 (m, 4H), 3.09 (s, 3H), 3.69-3.72 (m, 4H), 7.98-8.01 (m, d-like, 2H), 8.69-8.72 (m, d-like, 2H).

GLC/MS (pos. CI), m/z (%): found 312 (100); calcd. for C$_{15}$H$_{21}$NO$_4$S: 311.

Compound 7

2-Methyl-2-morpholino-1-phenyl-propan-1-one: The title compound is synthesized according to the published procedure (Calvin L. Stevens, Charles Hung Chang *J. Org. Chem.* 1962, 27, 4392).

$^1$H-NMR (300 MHz, CDCl$_3$), δ [ppm]: 1.35 (s, 6H), 2.60-2.62 (m, 4H), 3.71-3.73 (m, 4H), 7.41-7.45 (m, 2H), 7.52-7.56 (m, 1H), 8.55 (m, d-like, 2H).

GLC/MS (pos. CI), m/z (%): found 234.04 (100); calcd. for C$_{14}$H$_{19}$NO$_2$: 233.

Compound 8

2-[4-(2-Methyl-2-morpholin-4-ium-4-yl-propanoyl)phenyl]sulfanylacetic acid chloride: A solution of methyl 2-[4-(2-methyl-2-morpholino-propanoyl)phenyl]sulfanylacetate (prepared as described below; 1.15 g, 3.4 mmol) in hydrochloric acid (2 mol/L in water; 10 g) is stirred at 25° C. overnight. The reaction mixture is filtered and the filtrate extracted with diethylether. The aqueous phase is separated off and concentrated on a rotary evaporator to afford the title compound as a yellow solid (1.2 g).

$^1$H-NMR (300 MHz, D$_2$O), δ [ppm]: 1.75 (s, 6H), 3.28-3.37 (m, 4H), 3.88 (s, 2H), 3.91-3.97 (m, 2H), 4.08-4.12 (m, 2H), 7.34-7.37 (m, d-like, 2H), 7.75-7.78 (m, d-like, 2H).

LC/MS (pos. APCI), m/z (area %): found 324.15 (83); calcd. for C$_{16}$H$_{21}$NO$_4$SxH$^+$: 324.

Methyl 2-[4-(2-methyl-2-morpholino-propanoyl)phenyl]sulfanylacetate: N,N-Diisopropylethylamine (98%; 1.27 g, 9.6 mmol), methyl mercaptoacetate (99%; 0.47 g, 4.38 mmol), tris(dibenzylideneacetone)dipalladium(0) (0.2 g, 0.22 mmol) and 4,5-bis(diphenylphosphino)-9,9-dimethylxanthene (97%; 0.25 g, 0.42 mmol) were added to a solution of 1-(4-bromophenyl)-2-methyl-2-morpholino-propan-1-one (prepared as described below; 1.36 g, 4.36 mmol) in 1,4-dioxane (9 ml). The solution is brought to reflux and stirred for 21 hours. The reaction mixture is cooled to 25° C., diluted with diethylether and then extracted with hydrochloric acid (2 mol/L in water). The aqueous phase is separated off, cooled with ice and then basified by slow addition of sodium hydroxide (2 mol/L in water). The precipitate is filtered off, the filter cake washed with water and dried in a vacuum oven. The resulting solid is washed with diethylether to afford, after drying, the title compound as an orange solid (1.2 g).

$^1$H-NMR (300 MHz, CDCl$_3$), δ [ppm]: 1.31 (s, 6H), 2.55-2.58 (m, 4H), 3.67-3.70 (m, 4H), 3.75 (s, 2H), 3.76 (s, 3H), 7.32-7.35 (m, d-like, 2H), 8.49-8.52 (m, d-like, 2H).

GLC/MS (pos. CI), m/z (%): found 338.09 (100); calcd. for C$_{17}$H$_{23}$NO$_4$S: 337.

1-(4-Bromophenyl)-2-methyl-2-morpholino-propan-1-one: 2-(4-Bromo-phenyl)-2-methoxy-3,3-dimethyl-oxirane (prepared as described below; 192 g, 0.75 mol) is added to morpholine (203 g, 2.33 mol). The resulting mixture is brought to 130° C. and stirred for 21 hours. The reaction mixture is evaporated under reduced pressure to afford a dark red oil (228 g) which is taken up in toluene (200 ml), filtered and washed with HCl (16% in water). The organic phase is separated off and the solvent evaporated under reduced pressure to afford the title compound (154 g).

$^1$H-NMR (300 MHz, CDCl$_3$) δ [ppm]: 1.31 (s, 6H), 2.55-2.58 (m, 4H), 3.67-3.70 (m, 4H), 7.54-7.57 (m, d-like, 2H), 8.43-8.46 (m, d-like, 2H).

GLC/MS (pos. CI), m/z (%): found 312 (100), 314 (ca. 95); calcd. for C$_{14}$H$_{18}$($^{79}$Br)NO$_2$: 311, for C$_{14}$H$_{18}$($^{81}$Br)NO$_2$: 313.

2-(4-Bromophenyl)-2-methoxy-3,3-dimethyl-oxirane: 2-Bromo-1-(4-bromo-phenyl)-2-methyl-propan-1-one (prepared as described below; 208 g, 0.68 mol), dissolved in a mixture of chlorobenzene (180 ml) and methanol (100 ml), is slowly added to sodium methylate (30% in methanol; 125 g, 0.69 mol) while keeping the reaction temperature below 20° C. After 1.5 hours, precipitated sodium bromide is filtered off and the filtrate evaporated under reduced pressure to afford the title compound (192 g) which is used without further purification.

$^1$H-NMR (300 MHz, CDCl$_3$) δ [ppm]: 1.00 (s, 3H), 1.53 (s, 3H), 3.20 (s, 3H), 7.16-7.35 (m, 2H; additional signals due to the presence of residual chlorobenzene), 7.52 (d, J=9 Hz, 2H).

2-Bromo-1-(4-bromophenyl)-2-methyl-propan-1-one: 1-(4-bromophenyl)-2-methyl-propan-1-one (prepared according to Gonzalo Blay et al, *Tetrahedron* 2001, 57, 1075) is brominated in chlorobenzene with bromine (1 eq) in the presence of chlorosulfonic acid at room temperature. The title compound is obtained as a yellow oil (208 g; still containing some chlorobenzene) and is used without further purification.

$^1$H-NMR (300 MHz, CDCl$_3$) δ [ppm]: 2.02 (s, 6H), 7.27-7.34 (m, chlorobenzene), 7.58 (d, J=9 Hz, 2H), 8.03 (d, J=9 Hz, 2H).

Compound 9

1-[4-(2-Hydroxyethylsulfanyl)phenyl]-2-methyl-2-morpholino-propan-1-one: The title compound is synthesized according to the published procedure (EP88050 A2).

$^1$H-NMR (300 MHz, CDCl$_3$), δ [ppm]: 1.31 (s, 6H), 2.55-2.59 (m, 4H), 3.20-3.24 (m, t-like, 2H), 3.68-3.71 (m, 4H), 3.83-3.87 (m, t-like, 2H), 7.32-7.34 (m, d-like, 2H), 8.49-8.52 (m, d-like, 2H).

GLC/MS (pos. CI), m/z (%): found 310 (100); calcd. for C$_{16}$H$_{23}$NO$_3$S: 309.

Compound 10

1-[4-(2-Hydroxyethylsulfinyl)phenyl]-2-methyl-2-morpholino-propan-1-one: The title compound is synthesized from compound 9 according to the procedure described for the preparation of compound 5.

$^1$H-NMR (300 MHz, CDCl$_3$), δ [ppm]: 1.33 (s, 3H), 1.34 (s, 3H), 2.57-2.60 (m, 4H), 2.87-2.94 (m, 1H), 3.07 (ca., broad s, 1H), 3.20-3.29 (m, 1H), 3.68-3.72 (m, 4H), 4.03-4.10 (m, 1H), 4.16-4.24 (m, 1H), 7.68-7.71 (m, d-like, 2H), 8.69-8.72 (m, d-like, 2H).

GLC/MS (pos. CI), m/z (%): found 326 (100); calcd. for C$_{16}$H$_{23}$NO$_4$S: 325.

Compound 11

1-[4-(2-Hydroxyethoxy)phenyl]-2-methyl-2-morpholino-propan-1-one: The title compound is synthesized according to the published procedure (WO9621167 and EP88050).

$^1$H-NMR (300 MHz, CDCl$_3$), δ [ppm]: 1.31 (s, 6H), 2.04 (ca., broad s, 1H), 2.56-2.59 (m, 4H), 3.68-3.71 (m, 4H), 3.98-4.01 (m, t-like, 2H), 4.14-4.17 (m, t-like, 2H), 6.90-6.93 (m, d-like, 2H), 8.58-8.61 (m, d-like, 2H).

GLC/MS (pos. CI), m/z (%): found 294.04 (100); calcd. for C$_{16}$H$_{23}$NO$_4$: 293.

Compound 12

3-[4-(2-methyl-2-morpholino-propanoyl)phenyl]propanoic acid: The title compound is prepared by hydrolysis of methyl 3-[4-(2-methyl-2-morpholino-propanoyl)phenyl]propanoate (prepared as described below).

¹H-NMR (300 MHz, CDCl₃), δ [ppm]: 1.31 (s, 6H), 2.56-2.59 (m, 4H), 2.69-2.74 (m, t-like, 2H), 2.98-3.03 (m, t-like, 2H), 3.68-3.71 (m, 4H), 5.84 (ca., broad s, 1H), 7.24-7.27 (m, d-like, 2H), 8.47-8.50 (m, d-like, 2H).

MS (pos. APCI), m/z (%): found 306.13 (100); calcd. $C_{17}H_{23}NO_4$: 305.

3-[4-(2-methyl-2-morpholino-propanoyl)phenyl]propanoate: The title compound is prepared according to the method described for the preparation of 1-(4-bromophenyl)-2-methyl-2-morpholino-propan-1-one from bromobenzene, but using ethyl 3-phenylpropanoate instead.

Compound 13

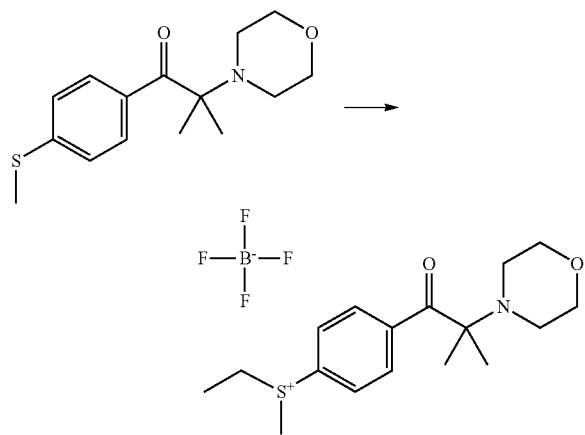

Ethyl-methyl-[4-(2-methyl-2-morpholino-propanoyl)phenyl]sulfonium tetrafluoroborate: Triethyloxonium tetrafluoroborate (97%; 0.45 g, 0.0023 mol), dissolved in dichloromethane (2 ml), is slowly added to a solution of 2-methyl-1-(4-methylsulfanylphenyl)-2-morpholinopropan-1-one (0.73 g, 0.0026 mol) in dichloromethane (6 ml) and the reaction mixture kept stirring for 5 hours at 25° C. Methanol (5 drops) is added and the resulting solution evaporated to dryness. The oily residue (1.2 g) is dissolved in acetone and then slowly added to stirred diethylether. Supernatants are decanted off and the precipitated oil dried on an oil pump to afford the title compound as a yellow solid (assay 90% by ¹H-NMR; 1.0 g).

¹H-NMR (300 MHz, CD₃CN), δ [ppm]: 1.30-1.35 (m, t-like, 3H), 1.33 (s, 6H), 2.56 (broad s, 4H), 3.20 (s, 3H), 3.52-3.70 (m, 2H), 3.64 (broad s, 4H), 7.95-7.97 (m, d-like, 2H), 8.71-8.73 (m, d-like, 2H);

MS (pos./neg. ESI), m/z (%): found 308.1 (100)/87.0 (100); calcd. for $[C_{17}H_{26}NO_2S]^+/[BF_4]^-$: 308/87.

Compound 14

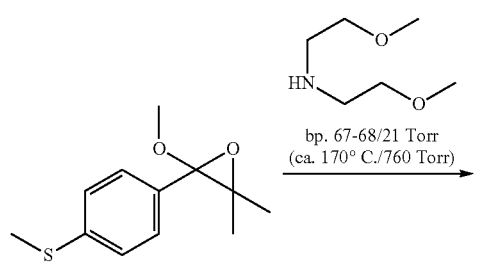

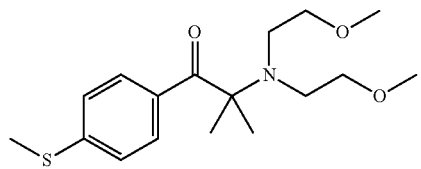

2-(Bis(2-methoxyethyl)amino)-2-methyl-1-(4-methylsulfanylphenyl)propan-1-one: The title compound is prepared from 2-methoxy-3,3-dimethyl-2-(4-methylsulfanylphenyl)oxirane (prepared according to EP88050A2) and bis(2-methoxyethyl)amine (6.4 equivalents) according to the preparation of compound 21 (160° C., 50 hours). Yellow liquid;

¹H-NMR (300 MHz, CDCl₃), δ [ppm]: 1.30 (s, 6H), 2.50 (s, 3H), 2.70-2.74 (m, t-like, 4H), 3.27 (s, 6H), 3.35-3.37 (m, t-like, 4H), 7.17-7.21 (m, d-like, 2H), 8.42-8.45 (m, d-like, 2H);

MS (CI), m/z (%): found 326 (100; MH⁺); calcd. for $C_{17}H_{27}NO_3S$: 325.

Compound 15

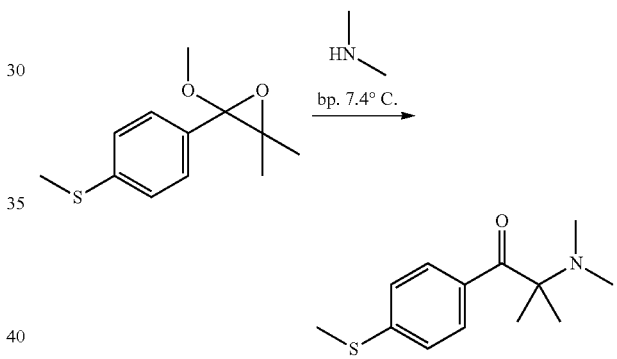

2-Dimethylamino-2-methyl-1-(4-methylsulfanylphenyl)propan-1-one: The title compound is prepared from 2-methoxy-3,3-dimethyl-2-(4-methylsulfanylphenyl)oxirane (prepared according to EP88050A2) and dimethylamine (4 equivalents) according to the preparation of compound 21 (150° C., 24 hours). Yellow liquid;

¹H-NMR (300 MHz, CDCl₃), δ [ppm]: 1.28 (s, 6H), 2.27 (s, 6H), 2.52 (s, 3H), 7.20-7.22 (m, d-like, 2H), 8.45-8.48 (m, d-like, 2H);

MS (CI), m/z (%): found 238 (100; MH⁺); calcd. for $C_{13}H_{19}NOS$: 237.

Compound 16

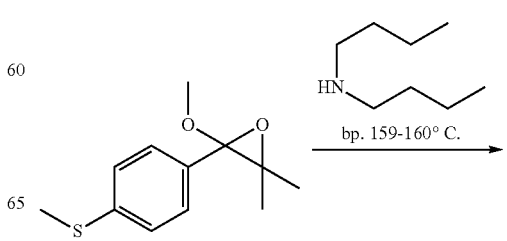

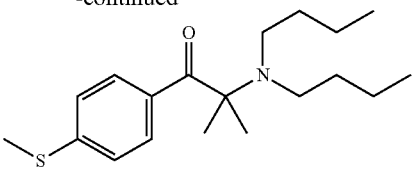

2-(Dibutylamino)-2-methyl-1-(4-methylsulfanylphenyl)propan-1-one: The title compound is prepared from 2-methoxy-3,3-dimethyl-2-(4-methylsulfanylphenyl)oxirane (prepared according to EP88050A2) and dibutylamine (4 equivalents) according to the preparation of compound 21 (ambient pressure, reflux, 160 hours). Yellow liquid;

$^1$H-NMR (300 MHz, CDCl$_3$), δ [ppm]: (ca.) 0.8-0.85 (m, t-like, 6H), 1.15-1.22 (m, 4H), 1.3 (s, 6H), 1.4-1.5 (m, 4H), 2.4-2.47 (m, 4H), 2.5 (s, 3H), 7.21-7.25 (m, d-like, 2H), 8.45-8.51 (m, d-like, 2H);

MS (CI), m/z (%): found 322 (100; MH$^+$); calcd. for C$_{19}$H$_{31}$NOS: 321.

Compound 17

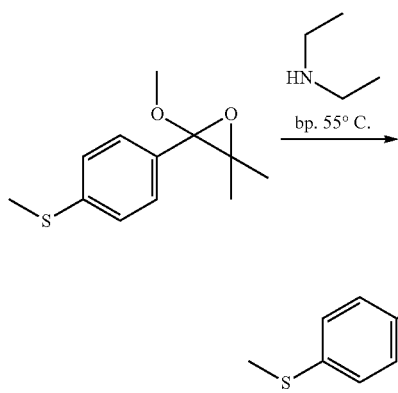

2-Diethylamino-2-methyl-1-(4-methylsulfanylphenyl)propan-1-one: The title compound is prepared from 2-methoxy-3,3-dimethyl-2-(4-methylsulfanylphenyl)oxirane (prepared according to EP88050A2) and dietylamine (4 equivalents) according to the preparation of compound 21 (150° C., 15 hours). Orange liquid;

$^1$H-NMR (300 MHz, CDCl$_3$), δ [ppm]: 1.04-1.09 (m, t-like, 6H), 1.33 (s, 6H), 2.54 (s, 3H), 2.54-2.62 (m, q-like, 4H), 7.21-7.24 (m, d-like, 2H), 8.54-8.57 (m, d-like, 2H);

MS (CI), m/z (%): found 266 (100; MH$^+$); calcd. for C$_{15}$H$_{23}$NOS: 265.

Compound 18

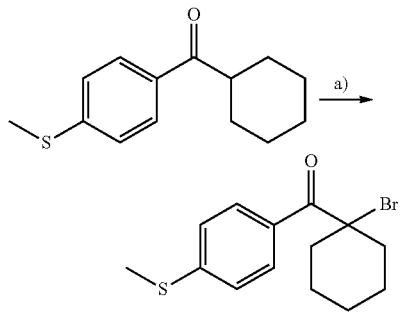

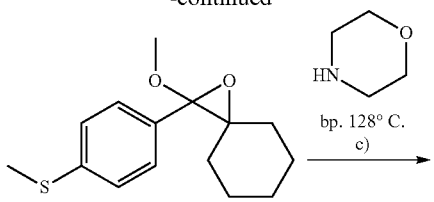

c) (4-Methylsulfanylphenyl)-(1-morpholinocyclohexyl)methanone: The title compound is prepared from 1-methoxy-1-(4-methylsulfanylphenyl)-2-oxaspiro[2.5]octane (prepared as described below) and morpholine (4 equivalents) according to the preparation of compound 21 (ambient pressure, reflux, 96 hours). Yellowish solid;

$^1$H-NMR (300 MHz, CDCl$_3$), δ [ppm]: 1.04-1.34 (m, 3H), 1.50-1.63 (m, 5H), 2.19-2.23 (m, 2H), 2.53 (s, 3H), 2.67-2.70 (m, 4H), 3.71-3.74 (m, 4H), 7.21-7.24 (m, d-like, 2H), 8.32-8.35 (m, d-like, 2H);

MS (CI), m/z (%): found 320 (100; MH$^+$); calcd. for C$_{18}$H$_{25}$NO$_2$S: 319.

b) 1-methoxy-1-(4-methylsulfanylphenyl)-2-oxaspiro[2.5]octane: Sodium methoxide (30% in methanol; 19.8 g, 0.11 mol) is slowly added to a solution of (1-bromocyclohexyl)-(4-methylsulfanylphenyl)methanone (prepared as described below; 98%, 31.9 g, 0.1 mol) in methanol (15 ml) and the reaction mixture stirred overnight at 25° C. Toluene and water are added, the organic phase split off and washed with water. Evaporation of the organic phase affords the title compound (25.6 g). Yellowish liquid;

$^1$H-NMR (300 MHz, CDCl$_3$), δ [ppm]: 1.14-1.34 (m, 3H), 1.39-1.68 (m, 4H), 1.76-1.88 (m, 2H), 1.94-2.01 (m, 1H), 2.52 (s, 3H), 3.21 (s, 3H), 7.25-7.28 (m, d-like, 2H), 7.39-7.41 (m, d-like, 2H);

MS (CI), m/z (%): found 265 (80; MH$^+$); calcd. for C$_{15}$H$_{20}$O$_2$S: 264.

a) (1-Bromocyclohexyl)-(4-methylsulfanylphenyl)methanone: Bromine (99%; 43.1 g, 0.267 mol) is slowly added at 19° C. to a suspension of cyclohexyl-(4-methylsulfanylphenyl)methanone (prepared according to U.S. Pat. No. 6,180,651; 63.3 g, 0.270 mol) in dichloroethane (200 ml) and the reaction mixture stirred overnight whilst bubbling some nitrogen below liquid level in order to constantly remove hydrogen bromide. The resulting solution is evaporated to dryness to afford the title compound (86.8 g). Orange liquid;

$^1$H-NMR (300 MHz, CDCl$_3$), δ [ppm]: 1.35-1.45 (m, 1H), 1.49-1.59 (m, 3H), 1.75-1.89 (m, 2H), 2.15-2.23 (m, 2H), 2.32-2.39 (m, 2H), 2.53 (s, 3H), 7.23 (m, d-like, 2H), 8.06-8.08 (m, d-like, 2H);

MS (CI), m/z (%): found 313 (90); calcd. for C$_{14}$H$_{17}$BrOS: 313.

Compound 19

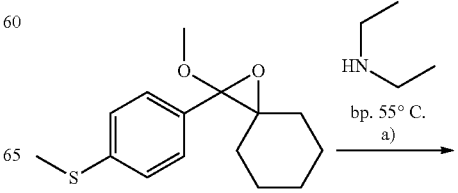

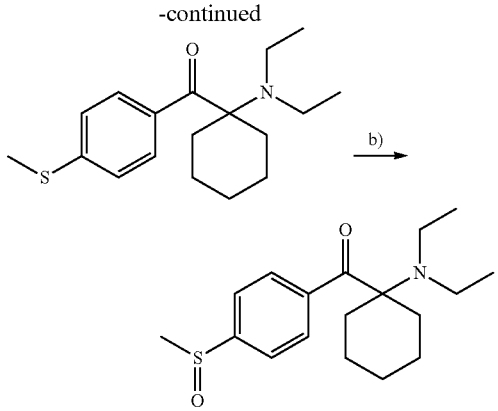

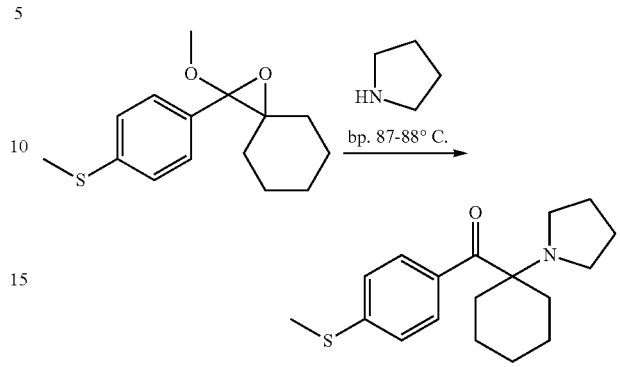

b) (1-Diethylaminocyclohexyl)-(4-methylsulfinylphenyl) methanone: The title compound is prepared from (1-diethylaminocyclohexyl)-(4-methylsulfanylphenyl)methanone (prepared as described below) and 3-chloroperoxybenzoic acid (1 equivalent) according to the preparation of compound 22 (reaction overnight; no further 3-chloroperoxybenzoic acid added and no post reaction). Orange liquid;

$^1$H-NMR (400 MHz, CDCl$_3$), δ [ppm]: 1.08-1.11 (m, t-like, 6H), 1.14-1.27 (m, 3H), 1.51-1.61 (m, 5H), 2.23-2.26 (m, 2H), 2.68-2.74 (m, q-like, 4H), 2.77 (s, 3H), 7.65-7.67 (m, d-like, 2H), 8.53-8.55 (m, d-like, 2H);

MS (CI), m/z (%): found 322 (100; MH$^+$); calcd. for C$_{18}$H$_{27}$NO$_2$S: 321.

a) (1-Diethylaminocyclohexyl)-(4-methylsulfanylphenyl) methanone: The title compound is prepared from 1-methoxy-1-(4-methylsulfanylphenyl)-2-oxaspiro[2.5]octane (intermediate for the preparation of compound 18) and dietylamine (5.5 equivalents) according to the preparation of compound 21 (150° C., 72 hours). Orange liquid;

$^1$H-NMR (300 MHz, CDCl$_3$), δ [ppm]: 1.06-1.11 (m, t-like, 6H), 1.16-1.36 (m, 3H), 1.47-1.60 (m, 5H), 2.25-2.29 (m, 2H), 2.52 (s, 3H), 2.64-2.72 (m, q-like, 4H), 7.20-7.22 (m, d-like, 2H), 8.37-8.40 (m, d-like, 2H);

MS (CI), m/z (%): found 306 (100; MH$^+$); calcd. for C$_{18}$H$_{27}$NOS: 305.

Compound 20

Diethyl-[2-(4-methoxyphenyl)-2-oxo-ethyl]ammonium chloride: Hydrochloric acid (1 mol/L in water; 8 ml, 8 mmol) is added to a dispersion of 2-diethylamino-1-(4-methoxyphenyl)-ethanone (prepared as described below; 88%; 2 g, 7.9 mmol) in water (8 ml). The resulting mixture is stirred at 25° C. for 20 minutes, filtered over a plug of hyflo and the filtrate evaporated on a rotary evaporator to afford the title compound as a viscous, brownish oil (1.3 g). The $^1$H-NMR spectrum (300 MHz, DMSO-d$_6$) corresponds to the structure of compound 20.

2-Diethylamino-1-(4-methoxyphenyl)ethanone: 2-Bromo-1-(4-methoxy-phenyl)ethanone (2.35 g, 10.3 mmol), dissolved in diethyl ether (10 ml), is slowly added to a solution of diethylamine (99%; 1.47 g, 19.9 mmol) in diethylether (8 ml). The reaction mixture is brought to reflux and stirred for 6 hours. The resulting suspension is cooled to 25° C., filtered and the filtrate evaporated on a rotary evaporator to afford the title compound as an orange oil (2.25 g).

$^1$H-NMR (300 MHz, DMSO-d$_6$), δ [ppm]: 0.93-0.98 (m, t-like, 6H), 2.51-2.58 (m, q-like, 4H), 3.77 (s, 2H), 3.83 (s, 3H), 7.00-7.02 (m, d-like, 2H), 7.99-8.01 (m, d-like, 2H).

GLC/MS (pos. CI), m/z (%): found 222 (100); calcd. for C$_{13}$H$_{19}$NO$_2$: 221.

Compound 21

(4-Methylsulfanylphenyl)-(1-pyrrolidin-1-ylcyclohexyl) methanone: 1-Methoxy-1-(4-methylsulfanylphenyl)-2-oxaspiro[2.5]octane (intermediate for the preparation of compound 18; 7 g, 0.0265 mol) and pyrrolidine (99%; 7.6 g, 0.1069 mol) are stirred together for 24 hours in an autoclave at 140° C. The autoclave is cooled down to 25° C., unloaded and excess pyrrolidine distilled off. Aqueous hydrochloric acid (2 mol/L; 20 ml) is added to the residue (8.1 g) and the resulting mixture extracted with diethylether. The aqueous phase is split off, basified by addition of conc. aqueous sodium hydroxide solution and extracted with diethylether. The organic phase is split off, dried over K$_2$CO$_3$, filtered and evaporated. Column chromatography (silica, hexane/ethylacetate) of the residue (6.6 g) affords the title compound as a yellow oil (3.2 g).

$^1$H-NMR (300 MHz, CDCl$_3$), δ [ppm]: 1.07-1.32 (m, 3H), 1.51-1.62 (m, 5H), 1.74 (broad s, 4H), 2.25-2.29 (m, d-like, 2H), 2.52 (s, 3H), 2.73 (broad s, 4H), 7.20-7.22 (m, d-like, 2H), 8.21-8.24 (m, d-like, 2H);

MS (CI), m/z (%): found 304 (100; MH$^+$); calcd. for C$_{18}$H$_{25}$NOS: 303.

Compound 22

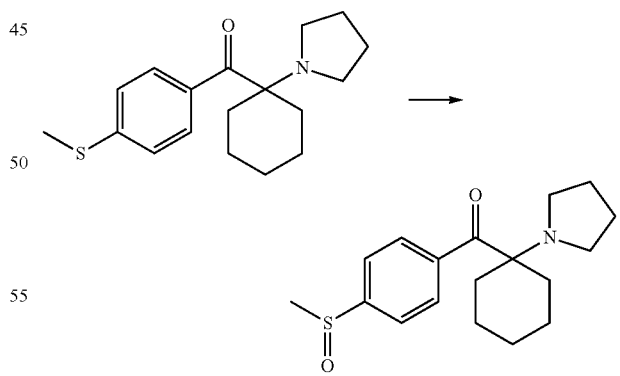

(4-Methylsulfinylphenyl)-(1-pyrrolidin-1-ylcyclohexyl) methanone: 3-Chloroperoxybenzoic acid (77%; 1.59 g, 0.0071 mol), dissolved in dichloromethane (15 ml), is slowly added to an ice-cooled solution of (4-methylsulfanylphenyl)-(1-pyrrolidin-1-ylcyclohexyl)methanone (compound 21; 2.15 g, 0.0071 mol) in dichloromethane (10 ml). The ice bath is removed and the reaction mixture stirred overnight. Another 3-chloroperoxybenzoic acid (77%; 0.24 g, 0.0011 mol) is added and the reaction mixture stirred for an additional 40 hours at 25° C. The resulting solution is sequentially washed with an aqueous solution of sodium hydroxide (2 mol/L) and brine, dried over MgSO$_4$, filtrated and then evaporated to dryness. Column chromatography (silica; hexane/ethylacetate) of the residue affords the title compound as a yellow solid.

$^1$H-NMR (300 MHz, CDCl$_3$), δ [ppm]: 1.10-1.29 (m, 3H), 1.53-1.62 (m, 5H), 1.76 (broad s, 4H), 2.21-2.24 (m, d-like, 2H), 2.73 (broad s, 4H), 2.76 (s, 3H), 7.64-7.66 (m, d-like, 2H), 8.35-8.37 (m, d-like, 2H);

MS (CI), m/z (%): found 320 (100; MH$^+$); calcd. for C$_{18}$H$_{25}$NO$_2$S: 319.

Compound 23

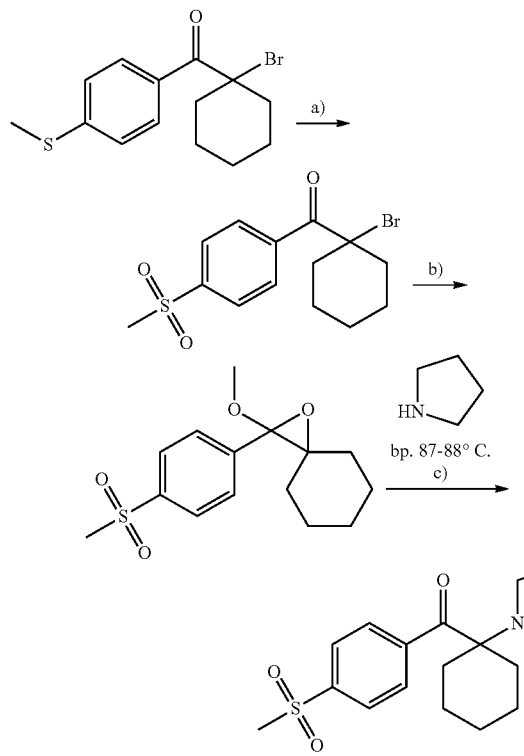

c) (4-methylsulfonylphenyl)-(1-pyrrolidin-1-ylcyclohexyl)methanone: The title compound is prepared from 2-methoxy-2-(4-methylsulfonylphenyl)-1-oxaspiro[2.5]octane (prepared as described below) and pyrrolidine (4 equivalents) according to the preparation of compound 21 (140° C., 48 hours). Yellow solid;

$^1$H-NMR (400 MHz, CDCl$_3$), δ [ppm]: 1.14-1.22 (m, 3H), 1.54-1.66 (m, 5H), 1.74-1.81 (m, 4H), 2.18-2.22 (m, 2H), 2.72-2.75 (m, 4H), 3.09 (s, 3H), 7.95-7.97 (m, d-like, 2H), 8.36-8.38 (m, d-like, 2H);

MS (CI), m/z (%): found 336 (100; MH$^+$); calcd. for C$_{18}$H$_{25}$NO$_3$S: 335.

b) 2-Methoxy-2-(4-methylsulfonylphenyl)-1-oxaspiro[2.5]octane: The title compound is prepared from (1-bromocyclohexyl)-(4-methylsulfonylphenyl)methanone (prepared as described below) and sodium methoxide according to the method described for the preparation of 2-methoxy-2-(4-methylsulfanylphenyl)-1-oxaspiro[2.5]octane (intermediate for the preparation of compound 18). Orange solid;

$^1$H-NMR (400 MHz, CDCl$_3$), δ [ppm]: 1.08-1.13 (m, 1H), 1.17-1.34 (m, 2H), 1.39-1.68 (m, 4H), 1.76-1.87 (m, 2H), 1.94-2.00 (m, 1H), 3.11 (s, 3H), 3.21 (s, 3H), 7.69-7.71 (m, d-like, 2H), 7.97-7.99 (m, d-like, 2H);

MS (CI), m/z (%): found 297 (100; MH$^+$); calcd. for C$_{15}$H$_{20}$O$_4$S: 296.

a) (1-Bromocyclohexyl)-(4-methylsulfonylphenyl)methanone: 3-Chloroperoxybenzoic acid (77%; 19.6 g, 0.0875 mol), dissolved in dichloromethane (120 ml), is slowly added to an ice-cooled solution of (1-bromocyclohexyl)-(4-methylsulfanylphenyl)methanone (intermediate for the preparation of compound 18; 13.4 g, 0.0428 mol) in dichloromethane (80 ml). The ice bath is removed and the reaction mixture stirred for 6 hours at 25° C. The resulting suspension is filtered and the filtrate washed with sodium carbonate solution (2 mol/L). The organic phase is split off, dried over MgSat, filtered and evaporated to dryness to afford the title compound (15.6 g) as a yellow solid.

$^1$H-NMR (400 MHz, CDCl$_3$), δ [ppm]: 1.38-1.46 (m, 1H), 1.50-1.65 (m, 3H), 1.77-1.88 (m, 2H), 2.14-2.19 (m, 2H), 2.28-2.34 (m, 2H), 3.11 (s, 3H), 8.01-8.03 (m, d-like, 2H), 8.21-8.23 (m, d-like, 2H);

LC/MS (pos. APCI), m/z (area %): found 344.8 (93); calcd. for C$_{14}$H$_{17}$BrO$_3$S: 345.

Compound 24

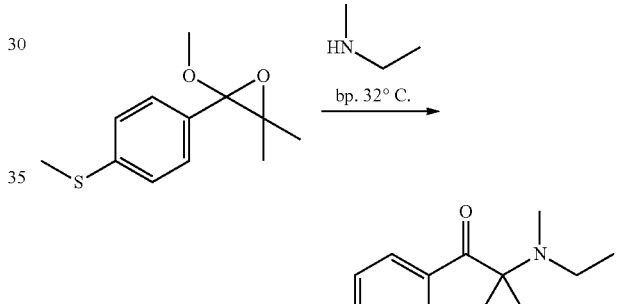

2-(Ethyl(methyl)amino)-2-methyl-1-(4-methylsulfanylphenyl)propan-1-one: The title compound is prepared from 2-methoxy-3,3-dimethyl-2-(4-methylsulfanylphenyl)oxirane (prepared according to EP88050A2) and N-ethylmethylamine (3 equivalents) according to the preparation of compound 21 (150° C., 48 hours). Yellow liquid;

$^1$H-NMR (300 MHz, CDCl$_3$), δ [ppm]: 0.99 (t, J=7.05 Hz, 3H), 1.29 (s, 6H), 2.26 (s, 3H), 2.40 (q, J=7.05 Hz, 2H), 2.53 (s, 3H), 7.21-7.24 (m, d-like, 2H), 8.50-8.53 (m, d-like, 2H);

MS (CI), m/z (%): found 252 (100; MH$^+$); calcd. for C$_{14}$H$_{21}$NOS: 251.

Compound 25

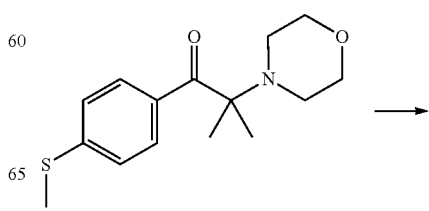

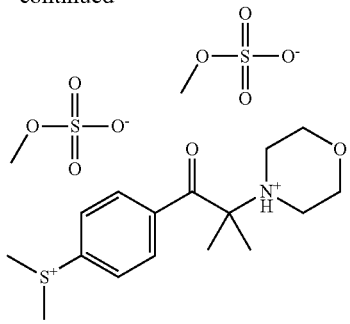

Dimethyl-[4-(2-methyl-2-morpholin-4-ium-4-yl-propanoyl)phenyl]sulfonium methyl sulfate: Dimethyl sulfate (99%; 24.5 g, 0.1923 mol) is slowly added at 25° C. to a solution of 2-methyl-1-(4-methylsulfanylphenyl)-2-morpholino-propan-1-one (5.4 g, 0.0193 mol) in acetonitrile (50 ml) containing water (0.35 g, 0.0194 mol). The reaction mixture is brought to 60° C. and stirred overnight. After cooling down to 25° C. toluene (40 ml) is added and the resulting dispersion allowed to settle. Supernatants are decanted and the remaining oil dried to afford the title compound (10.48 g). Yellow oil;

Elemental analysis (S and N only, %): found S 19.0, N 2.83, corresponding to a molar ratio S/N=2.9/1; calcd. S 18.6, N 2.71, corresponding to a molar ratio S/N=3/1;

MS (pos./neg. ESI), m/z (%): found 294.0 (100; M-H$^+$)/111.0 (100); calcd. for $[C_{16}H_{25}NO_2S]+/[CH_3O_4S]^-$: 295/111.

Compound 26

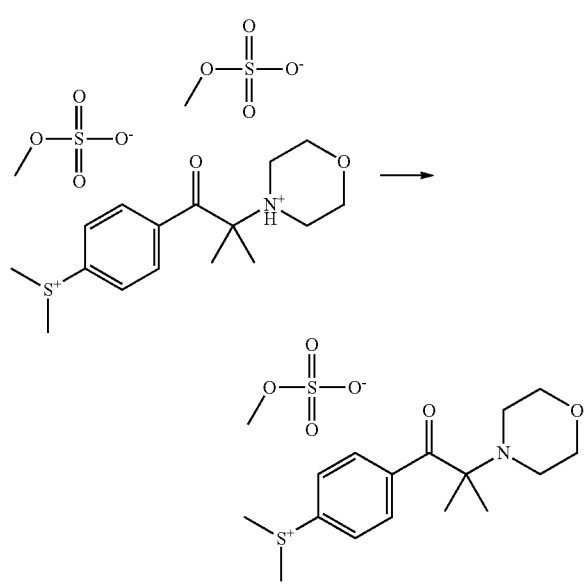

Dimethyl-[4-(2-methyl-2-morpholino-propanoyl)phenyl]sulfonium methyl sulfate: Dimethyl-[4-(2-methyl-2-morpholin-4-ium-4-yl-propanoyl)phenyl]sulfonium methyl sulfate (compound 25; 4.5 g, 0.0087 mol) is dissolved in an aqueous solution of sodium hydroxide (2 mol/L; 5 g, ca. 0.0093 mol). The resulting solution (pH ca. 4.5) is brought to pH 9.0 by portion wise addition of solid sodium carbonate (ca. 0.3 g) and then stirred at 25° C. for 30 minutes. Extraction with dichloromethane and evaporation of the organic solvent affords the title compound as a yellow solid (2.39 g).

$^1$H-NMR (300 MHz, CDCl$_3$), δ [ppm]: 1.31 (s, 6H), 2.55-2.58 (m, 4H), 3.55 (s, 6H), 3.69-3.72 (m, 4H), 3.70 (s, 3H), 8.16-8.19 (m, d-like, 2H), 8.76-8.79 (m, d-like, 2H);

MS (pos./neg. ESI), m/z (%): found 294.1 (100)/111.1 (100); calcd. for $[C_{16}H_{24}NO_2S]^+/[CH_3O_4S]^-$: 294/111.

Compound 27

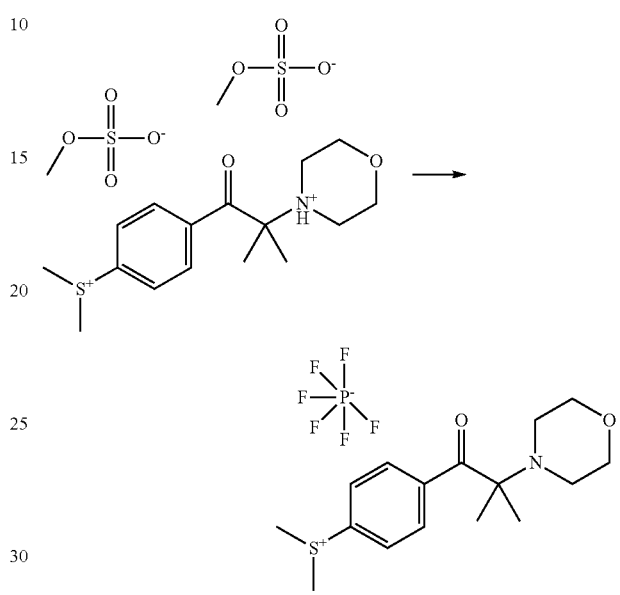

Dimethyl-[4-(2-methyl-2-morpholino-propanoyl)phenyl]sulfonium hexafluorophosphate: Sodium hexafluorophosphate (98%; 5.21 g, 0.0304 mol), dissolved in water (16 ml), is slowly added to a solution of dimethyl-[4-(2-methyl-2-morpholin-4-ium-4-yl-propanoyl)phenyl]sulfonium methyl sulfate (compound 25; 5.25 g, 0.0101 mol) in water (47 ml). The resulting solution (pH ca. 0.8) is brought to pH 9.2 by portion wise addition of an aqueous solution of sodium carbonate (2 mol/L; ca. 19.3 g). The precipitate is filtered, washed with water and dried to afford the title compound as a yellow solid (3.26 g).

$^1$H-NMR (400 MHz, CD$_3$CN), δ [ppm]: 1.32 (s, 6H), 2.55-2.57 (m, 4H), 3.19 (s, 6H), 3.63-3.65 (m, 4H), 7.97-7.99 (m, d-like, 2H), 8.71-8.73 (m, d-like, 2H);

MS (pos./neg. ESI), m/z (%): found 294.1 (100)/145.1 (100); calcd. for $[C_{16}H_{24}NO_2S]^+/[PF_6]^-$: 294/145.

Compound 28

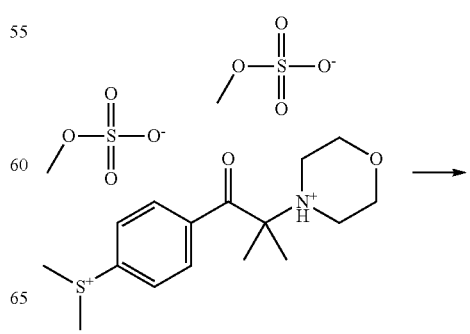

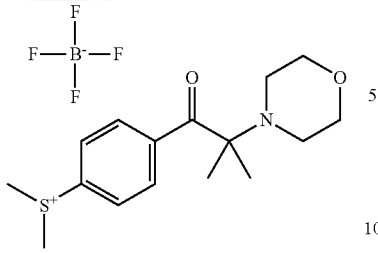

Dimethyl-[4-(2-methyl-2-morpholin-4-ium-4-yl-propanoyl)phenyl]sulfonium tetrafluoroborate: Dimethyl-[4-(2-methyl-2-morpholin-4-ium-4-yl-propanoyl)phenyl]sulfonium methyl sulfate (compound 25; 5.18 g, 0.01 mol) is dissolved in an aqueous solution of sodium hydroxide (2 mol/L; 5.4 g, ca. 0.01 mol). The resulting solution (pH ca. 4.6) is brought to pH 10.0 by portion wise addition of solid sodium carbonate (ca. 0.95 g) followed by the addition of a solution of sodium tetrafluoroborate (98%; 2.24 g, 0.02 mol) in water (9 ml). The precipitate is filtered, washed with water and dried to afford the title compound as a yellow solid (2.65 g).

$^1$H-NMR (400 MHz, CD$_3$CN), δ [ppm]: 1.32 (s, 6H), 2.55-2.58 (m, 4H), 3.21 (s, 6H), 3.63-3.67 (m, 4H), 7.98-8.01 (m, d-like, 2H), 8.71-8.74 (m, d-like, 2H);

MS (pos./neg. ESI), m/z (%): found 294 (100)/87 (100); calcd. for [C$_{16}$H$_{24}$NO$_2$S]$^+$/[BF$_4$]$^-$: 294/87.

Compound 29

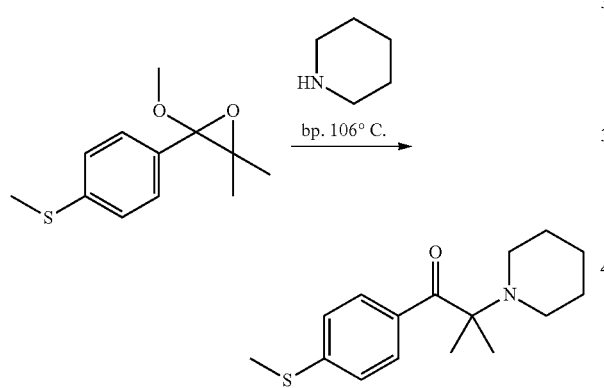

2-Methyl-1-(4-methylsulfanylphenyl)-2-(1-piperidyl)propan-1-one: The title compound is prepared from 2-methoxy-3,3-dimethyl-2-(4-methylsulfanylphenyl)oxirane (prepared according to EP88050A2) and piperidine according to EP88050A2. Yellowish solid;

$^1$H-NMR (300 MHz, CDCl$_3$), δ [ppm]: 1.29 (s, 6H), 1.46-1.51 (m, 2H), 1.51-1.59 (m, 4H), 2.49-2.52 (m, 4H), 2.54 (s, 3H), 7.22-7.25 (m, d-like, 2H), 8.57-8.60 (m, d-like, 2H);

MS (CI), m/z (%): found 278 (100; MH$^+$); calcd. for C$_{16}$H$_{23}$NOS: 277.

Compound 30

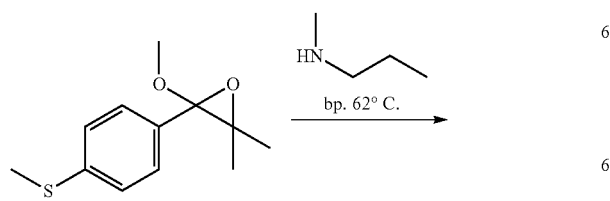

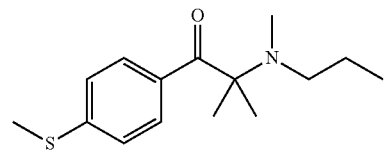

2-Methyl-2-(methyl(propyl)amino)-1-(4-methylsulfanylphenyl)propan-1-one: The title compound is prepared from 2-methoxy-3,3-dimethyl-2-(4-methylsulfanylphenyl)oxirane (prepared according to EP88050A2) and N-methylpropylamine (3 equivalents) according to the preparation of compound 21 (150° C., 22 hours). Yellow liquid;

$^1$H-NMR (300 MHz, CDCl$_3$), δ [ppm]: 0.82 (t, J=7.4 Hz, 3H), 1.30 (s, 6H), 1.40-1.52 (m, sextet-like, 2H), 2.22 (s, 3H), 2.31-2.36 (m, t-like, 2H), 2.53 (s, 3H), 7.20-7.23 (m, d-like, 2H), 8.49-8.51 (m, d-like, 2H);

MS (CI), m/z (%): found 266 (100; MH$^+$); calcd. for C$_{15}$H$_{23}$NOS: 265.

Compound 31

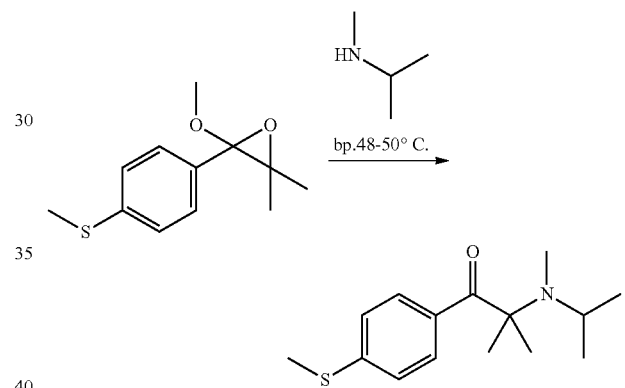

2-(Isopropyl(methyl)amino)-2-methyl-1-(4-methylsulfanylphenyl)propan-1-one: The title compound is prepared from 2-methoxy-3,3-dimethyl-2-(4-methylsulfanylphenyl)oxirane (prepared according to EP88050A2) and N-isopropylmethylamine (3 equivalents) according to the preparation of compound 21 (150° C., 23 hours). Yellow liquid;

$^1$H-NMR (300 MHz, CDCl$_3$), δ [ppm]: 0.99 (d, J=6.4 Hz, 6H), 1.34 (s, 6H), 2.24 (s, 3H), 2.53 (s, 3H), 3.03 (septet, J=6.4 Hz, 1H), 7.20-7.23 (m, d-like, 2H), 8.40-8.43 (m, d-like, 2H);

MS (CI), m/z (%): found 266 (100; MH$^+$); calcd. for C$_{15}$H$_{23}$NOS: 265.

Compound 32

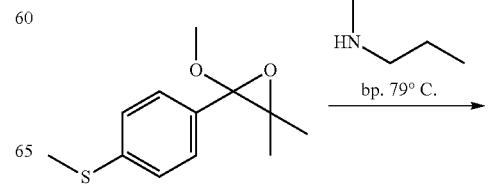

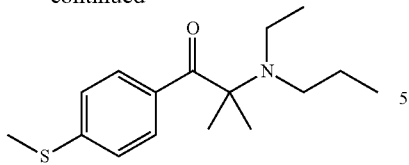

2-(Ethyl(propyl)amino)-2-methyl-1-(4-methylsulfanyl-phenyl)propan-1-one: The title compound is prepared from 2-methoxy-3,3-dimethyl-2-(4-methylsulfanylphenyl)oxirane (prepared according to EP88050A2) and N-ethylpropylamine (3 equivalents) according to the preparation of compound 21 (150° C., 70 hours). Yellow liquid;

$^{1}$H-NMR (300 MHz, CDCl$_3$), δ [ppm]: 0.82 (t, J=7.4 Hz, 3H), 1.03 (t, J=7.1 Hz, 3H), 1.33 (s, 6H), 1.47-1.60 (m, sextet-like, 2H), 2.43-2.48 (m, 2H), 2.52-2.59 (m, 2H), 2.53 (s, 3H), 7.21-7.23 (m, d-like, 2H), 8.53-8.55 (m, d-like, 2H);

MS (CI), m/z (%): found 280 (100; MH$^{+}$); calcd. for C$_{16}$H$_{25}$NOS: 279.

Compound 33

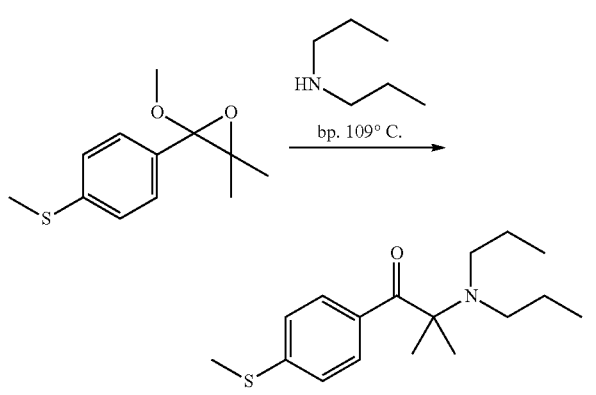

2-(Dipropylamino)-2-methyl-1-(4-methylsulfanylphenyl)propan-1-one: The title compound is prepared from 2-methoxy-3,3-dimethyl-2-(4-methylsulfanylphenyl)oxirane (prepared according to EP88050A2) and dipropylamine (3 equivalents) according to the preparation of compound 21 (150° C., 45 hours). Yellow liquid;

$^{1}$H-NMR (300 MHz, CDCl$_3$), δ [ppm]: 0.79 (t, J=7.4 Hz, 6H), 1.33 (s, 6H), 1.43-1.56 (m, sextet-like, 4H), 2.40-2.45 (m, 4H), 2.53 (s, 3H), 7.21-7.23 (m, d-like, 2H), 8.51-8.54 (m, d-like, 2H);

MS (CI), m/z (%): found 294 (100; MH$^{+}$); calcd. for C$_{17}$H$_{27}$NOS: 293.

Compound 34

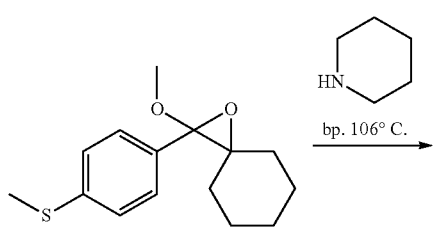

(4-Methylsulfanylphenyl)-[1-(1-piperidyl)cyclohexyl]methanone: The title compound is prepared from 1-methoxy-1-(4-methylsulfanylphenyl)-2-oxaspiro[2.5]octane (intermediate for the preparation of compound 18) and piperidine (4 equivalents) according to the preparation of compound 21 (150° C., 22 hours). Brownish oil;

$^{1}$H-NMR (300 MHz, CDCl$_3$), δ [ppm]: 1.06-1.16 (m, 1H), 1.20-1.35 (m, 2H), 1.42-1.52 (m, 2H), 1.52-1.61 (m, 9H), 2.14-2.18 (m, 2H), 2.53 (s, 3H), 2.61-2.64 (m, 4H), 7.20-7.23 (m, d-like, 2H), 8.39-8.41 (m, d-like, 2H);

MS (CI), m/z (%): found 318 (100; MH$^{+}$); calcd. for C$_{19}$H$_{27}$NOS: 317.

Compound 35

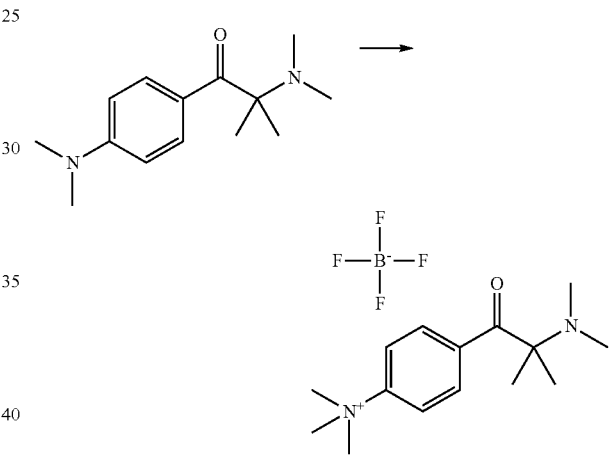

[4-(2-Dimethylamino-2-methyl-propanoyl)phenyl]-trimethyl-ammonium tetrafluoroborate: Dimethyl sulfate (99%; 26.7 g, 0.21 mol) is slowly added at 25° C. to a solution of 2-dimethylamino-1-(4-dimethylaminophenyl)-2-methyl-propan-1-one (prepared according to EP138754A2; 4.96 g, 0.021 mol) in acetonitrile (50 ml) containing water (0.38 g, 0.021 mol), the reaction mixture stirred at 25° C. for ca. 40 hours and the resulting suspension filtered. Toluene (50 ml) is added to the filtrate and supernatants decanted. The remaining oil (6.8 g) is dried and re-dissolved in water (6.8 ml). The resulting solution (pH ca. 0.3) is brought to pH 9.2 by portion wise addition of an aqueous solution of sodium carbonate (2 mol/L; ca. 5.5 g) followed by the addition of a solution of sodium tetrafluoroborate (98%; 4.24 g, 0.0378 mol) in water (8 ml). The resulting suspension (pH ca. 8.3) is brought again to pH 9.2 by further addition of solid sodium carbonate (2.5 g). The precipitate is filtered, washed with water and dried to afford the title compound as a yellow solid (1.8 g).

$^{1}$H-NMR (300 MHz, D$_2$O), δ [ppm]: 1.29 (s, 6H), 2.16 (s, 6H), 3.56 (s, 9H), 7.80-7.83 (m, d-like, 2H), 8.00-8.02 (m, d-like, 2H);

MS (pos./neg. ESI), m/z (%): found 249 (100)/87 (100); calcd. for [C$_{15}$H$_{25}$N$_2$O]+/[BF$_4$]$^{-}$: 249/87.

Compound 36

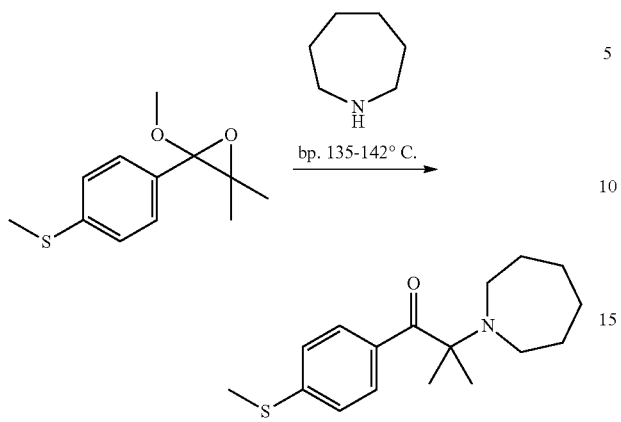

2-(Azepan-1-yl)-2-methyl-1-(4-methylsulfanylphenyl)propan-1-one: The title compound is prepared from 2-methoxy-3,3-dimethyl-2-(4-methylsulfanylphenyl)oxirane (prepared according to EP88050A2) and hexamethyleneimine (4 equivalents) according to the preparation of compound 21 (ambient pressure, 140° C., 18 hours). Brownish liquid;

$^1$H-NMR (300 MHz, CDCl$_3$), δ [ppm]: 1.32 (s, 6H), 1.48-1.64 (m, 8H), 2.54 (s, 3H), 2.62-2.65 (m, t-like, 4H), 7.22-7.23 (m, d-like, 2H), 8.53-8.56 (m, d-like, 2H);

MS (CI), m/z (%): found 293 (100; MH$_2^+$); calcd. for C$_{17}$H$_{25}$NOS: 291.

Compound 37

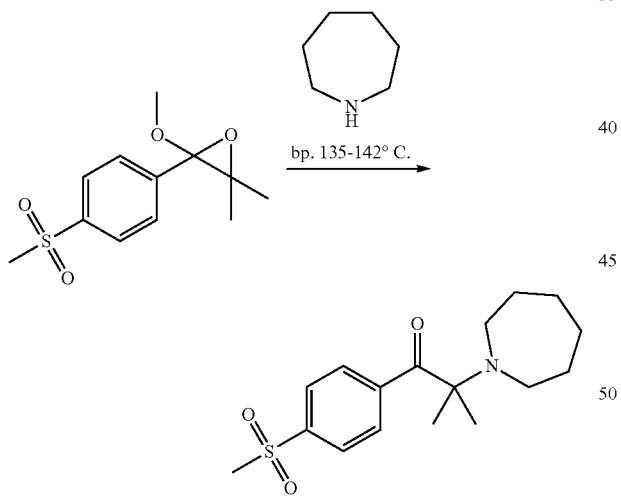

2-(Azepan-1-yl)-2-methyl-1-(4-methylsulfonylphenyl)propan-1-one: The title compound is prepared from 2-methoxy-3,3-dimethyl-2-(4-methylsulfonylphenyl)oxirane (intermediate for the preparation of compound 41) and hexamethyleneimine (4 equivalents) according to the preparation of compound 21 (ambient pressure, reflux, overnight). Yellow solid;

$^1$H-NMR (300 MHz, CDCl$_3$), δ [ppm]: 1.34 (s, 6H), 1.48-1.64 (m, 8H), 2.63-2.67 (m, t-like, 4H), 3.11 (s, 3H), 7.99-8.02 (m, d-like, 2H), 8.75-8.78 (m, d-like, 2H);

MS (CI), m/z (%): found 324.2 (100; MH$^+$); calcd. for C$_{17}$H$_{25}$NO$_3$S: 323.

Compound 40

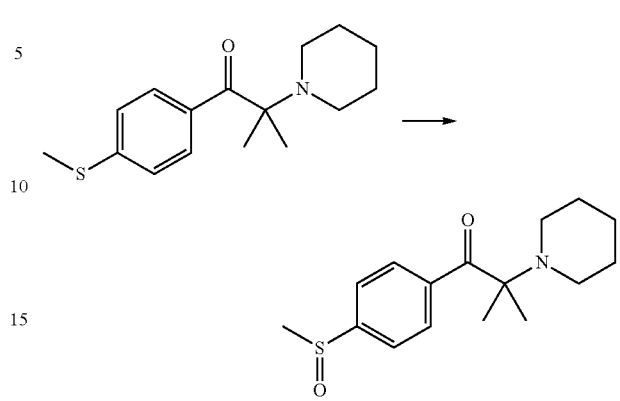

2-Methyl-1-(4-methylsulfinylphenyl)-2-(1-piperidyl)propan-1-one: The title compound is prepared from 2-methyl-1-(4-methylsulfanylphenyl)-2-(1-piperidyl)propan-1-one (compound 29) and 3-chloroperoxybenzoic acid (1 equivalent) according to the preparation of compound 22 (reaction overnight; no further 3-chloroperoxybenzoic acid added and no post reaction). Slightly yellow solid;

$^1$H-NMR (300 MHz, CDCl$_3$), δ [ppm]: 1.307 (s, 3H), 1.311 (s, 3H), 1.43-1.60 (m, 6H), 2.50-2.54 (m, t-like, 4H), 2.78 (s, 3H), 7.67-7.70 (m, d-like, 2H), 8.75-8.78 (m, d-like, 2H);

MS (CI), m/z (%): found 294 (100; MH$^+$); calcd. for C$_{16}$H$_{23}$NO$_2$S: 293.

Compound 41

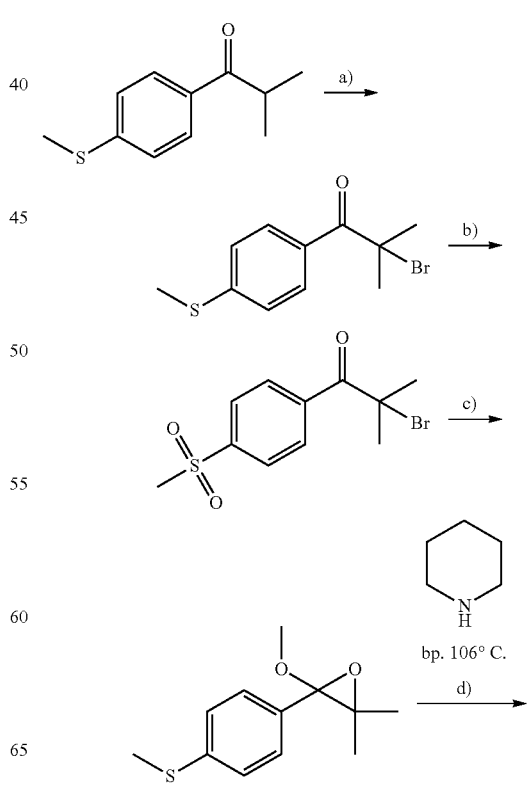

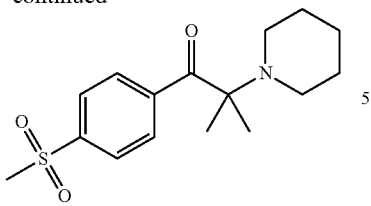

d) 2-Methyl-1-(4-methylsulfonylphenyl)-2-(1-piperidyl) propan-1-one: The title compound is prepared from 2-methoxy-3,3-dimethyl-2-(4-methylsulfonylphenyl)oxirane (prepared as described below) and piperidine (4 equivalents) according to the preparation of compound 21 (ambient pressure, reflux, overnight). Beige solid;

$^1$H-NMR (300 MHz, CDCl$_3$), δ [ppm]: 1.31 (s, 6H), 1.45-1.64 (m, 6H), 2.50-2.53 (m, 4H), 3.11 (s, 3H), 7.98-8.01 (m, d-like, 2H), 8.77-8.80 (m, d-like, 2H);

MS (CI), m/z (%): found 310 (100; MH$^+$); calcd. for C$_{16}$H$_{23}$NO$_3$S: 309.

c) 2-Methoxy-3,3-dimethyl-2-(4-methylsulfonylphenyl) oxirane: The title compound is prepared from 2-bromo-2-methyl-1-(4-methylsulfonylphenyl)propan-1-one (prepared as described below) and sodium methoxide according to the method described for the preparation of 2-methoxy-2-(4-methylsulfanylphenyl)-1-oxaspiro[2.5]octane (intermediate for the preparation of compound 18). Yellow to orange solid;

$^1$H-NMR (300 MHz, CDCl$_3$), δ [ppm]: 1.02 (s, 3H), 1.57 (s, 3H), 3.11 (s, 3H), 3.22 (s, 3H), 7.68-7.71 (m, d-like, 2H), 7.97-8.00 (m, d-like, 2H);

MS (CI), m/z (%): found 257 (100; MH$^+$); calcd. for C$_{12}$H$_{16}$O$_4$S: 256.

b) 2-Bromo-2-methyl-1-(4-methylsulfonylphenyl)propan-1-one: The title compound is prepared from 2-bromo-2-methyl-1-(4-methylsulfanylphenyl)propan-1-one (prepared as described below) and 3-chloroperoxybenzoic acid according to the method described for the preparation of (1-bromocyclohexyl)-(4-methylsulfonylphenyl)methanone (intermediate for the preparation of compound 23). White solid;

$^1$H-NMR (300 MHz, CDCl$_3$), δ [ppm]: 2.05 (s, 6H), 3.11 (s, 3H), 8.03-8.05 (m, d-like, 2H), 8.26-8.29 (m, d-like, 2H);

MS (CI), m/z (%): found 305 (100); calcd. for C$_{11}$H$_{13}$BrO$_3$S: 305.

a) 2-Bromo-2-methyl-1-(4-methylsulfanylphenyl)propan-1-one: The title compound is prepared from 2-methyl-1-(4-methylsulfanylphenyl)propan-1-one (prepared according to e.g. *Tetrahedron* 2003, 59, 7915-7920) and bromine according to the method described for the preparation of (1-bromocyclohexyl)-(4-methylsulfanylphenyl)methanone (intermediate for the preparation of compound 18). Orange liquid;

$^1$H-NMR (300 MHz, CDCl$_3$), δ [ppm]: 2.05 (s, 6H), 2.55 (s, 3H), 7.25-7.28 (m, d-like, 2H), 8.13-8.16 (m, d-like, 2H);

MS (CI), m/z (%): found 274.9 (100; MH$^+$); calcd. for C$_{11}$H$_{13}$BrOS: 273.

Compound 42

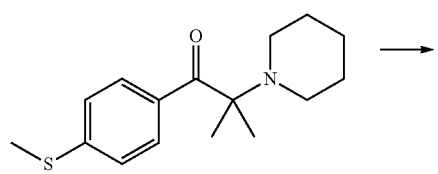

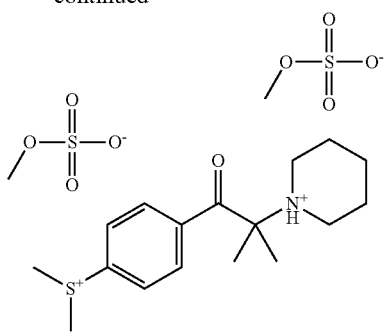

Dimethyl-[4-(2-methyl-2-piperidin-1-ium-1-yl-propanoyl)phenyl]sulfonium methyl sulfate: The title compound is prepared from 2-methyl-1-(4-methylsulfanylphenyl)-2-(1-piperidyl)propan-1-one (compound 29), water and dimethyl sulphate according to the preparation of compound 25. Orange liquid;

MS (pos./neg. ESI), m/z (%): found 292.0 (40; M-H$^+$)/ 111.0 (100); calcd. for [C$_{17}$H$_{27}$NOS]$^+$/[CH$_3$O$_4$S]$^-$: 293/111.

Compound 43

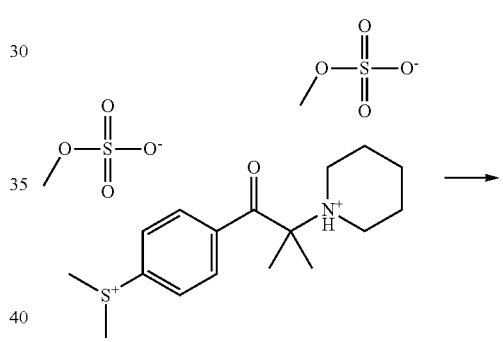

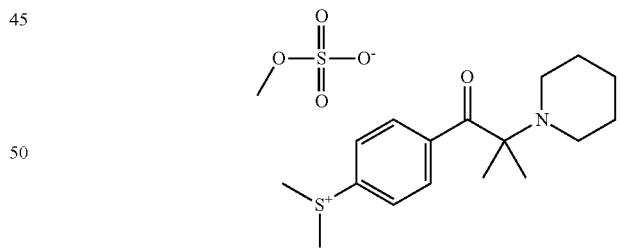

Dimethyl-[4-[2-methyl-2-(1-piperidyl)propanoyl]phenyl] sulfonium methyl sulfate: The title compound is prepared from dimethyl-[4-(2-methyl-2-piperidin-1-ium-1-yl-propanoyl)phenyl]sulfonium methyl sulfate (compound 42) according to the preparation of compound 26. Yellow solid;

$^1$H-NMR (300 MHz, D$_2$O), δ [ppm]: 1.22 (s, 6H), 1.29-1.49 (m, 6H), 2.39-2.48 (m, 4H), 3.19 (s, 6H), 3.64 (s, 3H), 7.91-7.94 (m, d-like, 2H), 8.36-8.38 (m, d-like, 2H);

MS (pos./neg. ESI), m/z (%): found 292.1 (30)/111.1 (100); calcd. for [C$_{17}$H$_{26}$NOS]$^+$/[CH$_3$O$_4$S]$^-$: 292/111.

Compound 44

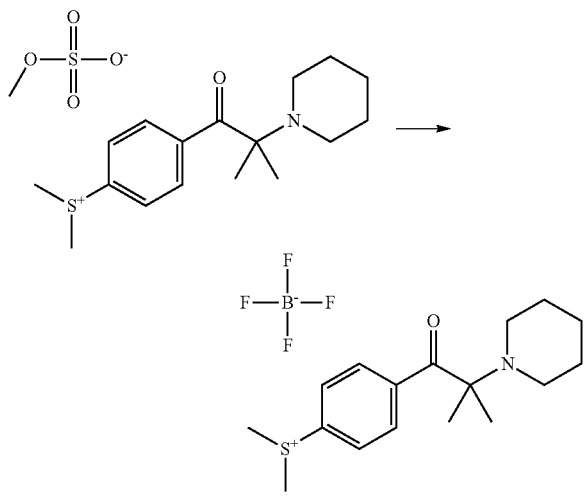

Dimethyl-[4-[2-methyl-2-(1-piperidyl)propanoyl]phenyl]sulfonium tetrafluoroborate: A suspension of dimethyl-[4-[2-methyl-2-(1-piperidyl)propanoyl]phenyl]sulfonium methyl sulfate (compound 43; 1.0 g, 0.0025 mol) in water (5.6 ml) is brought to pH 2.9 by portion wise addition of aqueous hydrochloric acid (4 mol/L) followed by the addition of a solution of sodium tetrafluoroborate (0.45 g, 0.0041 mol) in water (0.45 g). The resulting solution is brought to pH 9 by portion wise addition of aqueous sodium carbonate solution (2 mol/L). Filtration and drying of the filter-cake affords the title compound (0.76 g). Yellow solid;

$^1$H-NMR (300 MHz, D$_2$O), δ [ppm]: 1.24 (s, 6H), 1.29-1.39 (m, 2H), 1.39-1.49 (m, 4H), 2.42-2.50 (m, 4H), 3.18 (s, 6H), 7.90-7.93 (m, d-like, 2H), 8.32-8.35 (m, d-like, 2H);

MS (pos./neg. ESI), m/z (%): found 292 (30)/87 (100); calcd. for [C$_{17}$H$_{26}$NOS]+/[BF$_4$]$^-$: 292/87.

Compound 45

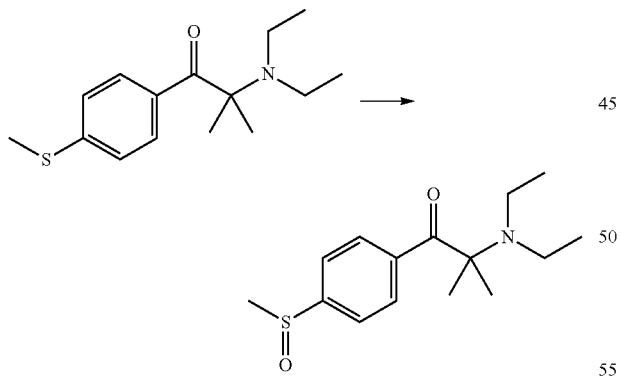

2-Diethylamino-2-methyl-1-(4-methylsulfinylphenyl)propan-1-one: The title compound is prepared from 2-diethylamino-2-methyl-1-(4-methylsulfanylphenyl)propan-1-one (compound 17) and 3-chloroperoxybenzoic acid (1 equivalent) according to the preparation of compound 22 (reaction overnight; no further 3-chloroperoxybenzoic acid added and no post reaction). Yellow liquid;

$^1$H-NMR (300 MHz, CDCl$_3$), δ [ppm]: 1.05 (t, J=7.1 Hz, 6H), 1.35 (s, 6H), 2.58 (q, J=7.1 Hz, 4H), 2.77 (s, 3H), 7.66-7.69 (m, d-like, 2H), 8.71-8.73 (m, d-like, 2H);

MS (CI), m/z (%): found 282 (100; MH$^+$); calcd. C$_{15}$H$_{23}$NO$_2$S: 281.

Compound 46

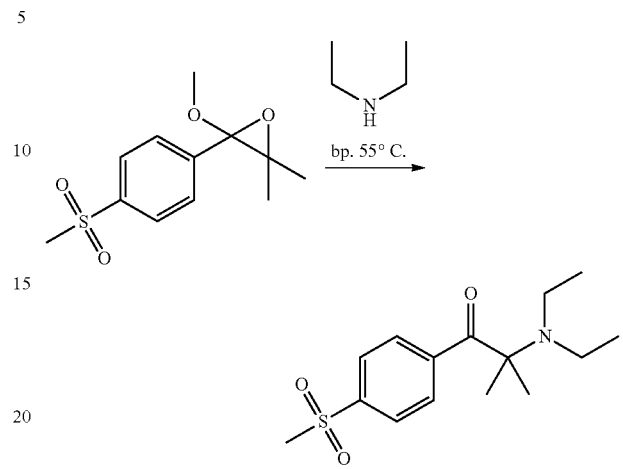

2-Diethylamino-2-methyl-1-(4-methylsulfonylphenyl)propan-1-one: The title compound is prepared from 2-methoxy-3,3-dimethyl-2-(4-methylsulfonylphenyl)oxirane (intermediate for the preparation of compound 41) and diethylamine (4 equivalents) according to the preparation of compound 21 (150° C., 44 hours). Yellow solid;

$^1$H-NMR (300 MHz, CDCl$_3$), δ [ppm]: 1.06 (t, J=7.1 Hz, 6H), 1.35 (s, 6H), 2.59 (q, J=7.1 Hz, 4H), 3.1 (s, 3H), 7.97-8.00 (m, d-like, 2H), 8.73-8.76 (m, d-like, 2H);

MS (CI), m/z (%): found 298.1 (100; MH$^+$); calcd. for C$_{15}$H$_{23}$NO$_3$S: 297.

Compound 47

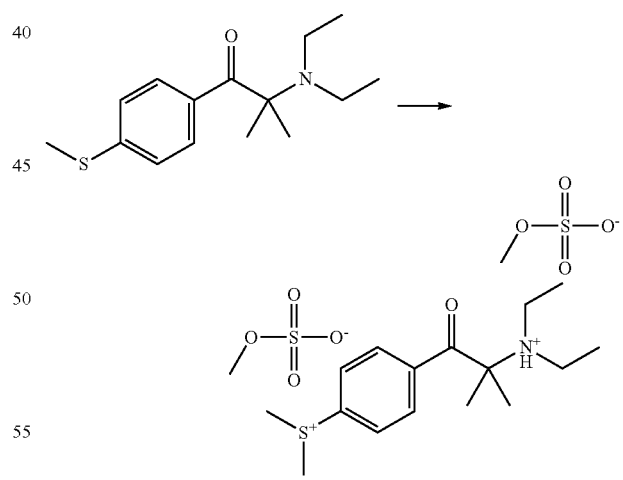

[2-(4-Dimethylsulfoniophenyl)-1,1-dimethyl-2-oxoethyl]-diethyl-ammonium methyl sulfate:

The title compound is prepared from 2-diethylamino-2-methyl-1-(4-methylsulfanylphenyl)propan-1-one (compound 17), water and dimethyl sulphate according to the preparation of compound 25. Red brown liquid;

MS (pos./neg. ESI), m/z (%): found 280 (25; M-H$^+$)/111.0 (100); calcd. for [C$_{16}$H$_{27}$NOS]+/[CH$_3$O$_4$S]$^-$: 281/111;

Compound 48

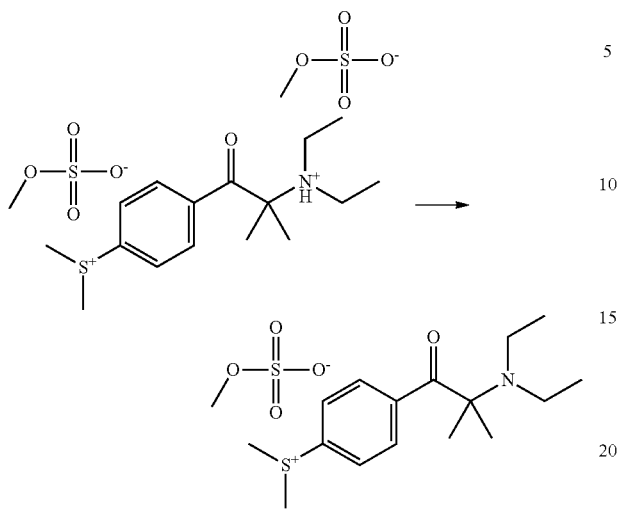

[4-(2-Diethylamino-2-methyl-propanoyl)phenyl]-dimethyl-sulfonium methyl sulfate: [2-(4-Dimethylsulfoniophenyl)-1,1-dimethyl-2-oxo-ethyl]-diethyl-ammonium methyl sulfate (compound 47; 16 g, 0.0318 mol) is dissolved in water (16 ml), the pH of the acidic solution (pH ca. 0.1) brought to pH 9.0 by portion wise addition of an aqueous solution of sodium carbonate (2 mol/L; ca. 27.1 g) and the resulting opaque solution stirred at 25° C. for 30 minutes. Extraction with dichloromethane and evaporation of the organic solvent affords the title compound as a yellow solid (8.44 g). Yellow solid;

$^1$H-NMR (300 MHz, D$_2$O), δ [ppm]: 0.91 (t, J=7.1 Hz, 6H), 1.29 (s, 6H), 2.52 (q, J=7.1 Hz, 4H), 3.20 (s, 6H), 3.64 (s, 3H), 7.92-7.95 (m, d-like, 2H), 8.37-8.40 (m, d-like, 2H);

MS (pos./neg. ESI), m/z (%): found 280 (100)/111.1 (100); calcd. for $[C_{16}H_{26}NOS]^+/[CH_3O_4S]^-$: 280/111.

Compound 49

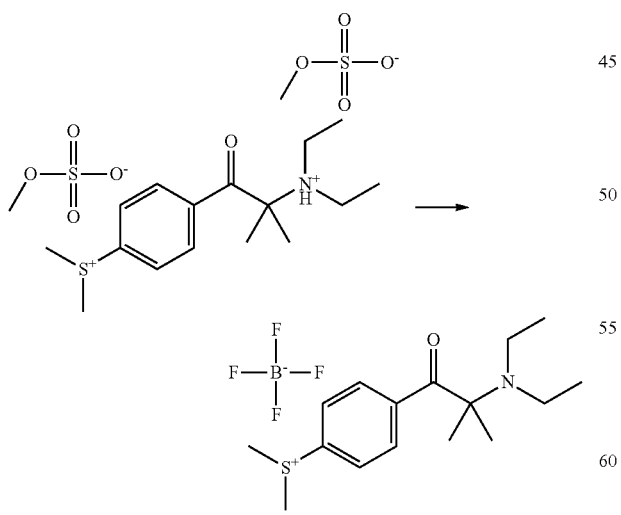

[4-(2-Diethylamino-2-methyl-propanoyl)phenyl]-dimethyl-sulfonium tetrafluoroborate: Sodium tetrafluoroborate (98%; 7.1 g, 0.0634 mol), dissolved in water (7.1 g), is added to a solution of [2-(4-dimethylsulfoniophenyl)-1,1-dimethyl-2-oxo-ethyl]-diethyl-ammonium methyl sulfate (compound 47; 16 g, 0.0318 mol) in water (16 ml). The resulting slightly opaque solution (pH ca. 1.2) is stirred at 25° C. for one hour and then the pH brought to 9.0 by portion wise addition of an aqueous solution of sodium carbonate (2 mol/L; ca. 31.3 g). The resulting suspension is stirred at 25° C. for 15 minutes, filtered and the filter-cake dried to afford the title compound (7.31 g). Yellow solid;

$^1$H-NMR (300 MHz, D$_2$O), δ [ppm]: 0.92 (t, J=7.0 Hz, 6H), 1.30 (s, 6H), 2.54 (q, J=7.0 Hz, 4H), 3.19 (s, 6H), 7.91-7.94 (m, d-like, 2H), 8.35-8.37 (m, d-like, 2H);

MS (pos./neg. ESI), m/z (%): found 280 (100)/87 (100); calcd. for $[C_{16}H_{26}NOS]^+/[BF_4]^-$: 280/87.

Compound 50

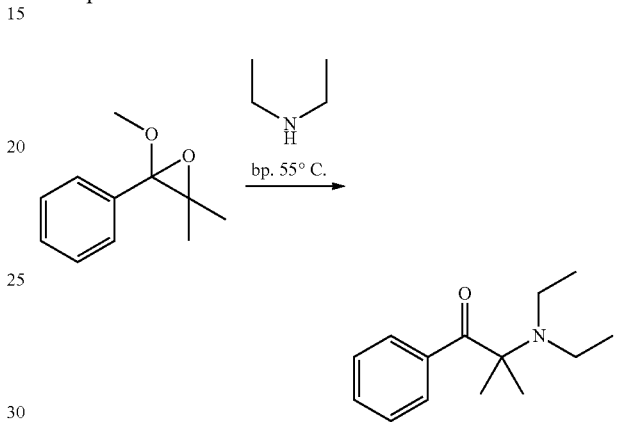

2-Diethylamino-2-methyl-1-phenyl-propan-1-one: The title compound is prepared from 2-methoxy-3,3-dimethyl-2-phenyl-oxirane (prepared according to FR1447116) and diethylamine (4 equivalents) according to the preparation of compound 21 (150° C., 44 hours). Yellow orange liquid;

$^1$H-NMR (300 MHz, CDCl$_3$), δ [ppm]: 1.07 (t, J=7.1 Hz, 6H), 1.35 (s, 6H), 2.60 (q, J=7.1 Hz, 4H), 7.38-7.43 (m, 2H), 7.48-7.53 (m, 1H), 8.56-8.59 (m, 2H);

MS (CI), m/z (%): found 220.15 (100; MH$^+$); calcd. for C$_{14}$H$_{21}$NO: 219.

Compound 52

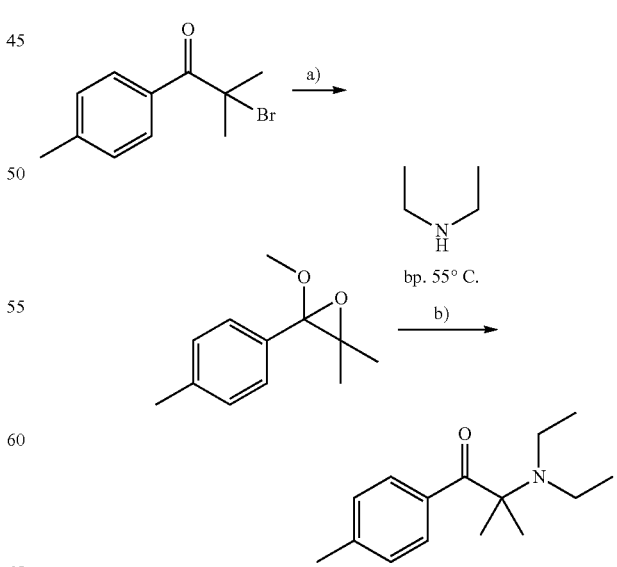

b) 2-Diethylamino-2-methyl-1-(p-tolyl)propan-1-one: The title compound is prepared from 2-methoxy-3,3-dimethyl-2-(p-tolyl)oxirane (prepared as described below) and diethylamine (4 equivalents) according to the preparation of compound 21 (150° C., 48 hours). Yellowish liquid;

$^1$H-NMR (300 MHz, CDCl$_3$), δ [ppm]: 1.07 (t, J=5.4 Hz, 6H), 1.34 (s, 6H), 2.41 (s, 3H), 2.60 (q, J=5.4 Hz, 4H), 7.21 (d, J=6.3 Hz, 2H), 8.51 (d, J=6.3 Hz, 2H);

MS (CI), m/z (%): found 234.2 (100; MH$^+$); calcd. for C$_{15}$H$_{23}$NO: 233.

a) 2-Methoxy-3,3-dimethyl-2-(p-tolyl)oxirane: The title compound is prepared from 2-bromo-2-methyl-1-(p-tolyl)propan-1-one (prepared according to *Journal of Organic Chemistry* 1956, 21, 1120-1123) and sodium methoxide according to the preparation of 1-methoxy-1-(4-methylsulfanylphenyl)-2-oxaspiro[2.5]octane (intermediate for the preparation of compound 18). Colourless liquid;

$^1$H-NMR (300 MHz, CDCl$_3$), δ [ppm]: 1.03 (s, 3H), 1.56 (s, 3H), 2.39 (s, 3H), 3.22 (s, 3H), 7.21 (d, J=6.3 Hz, 2H), 7.36 (d, J=6.3 Hz, 2H).

Compound 54

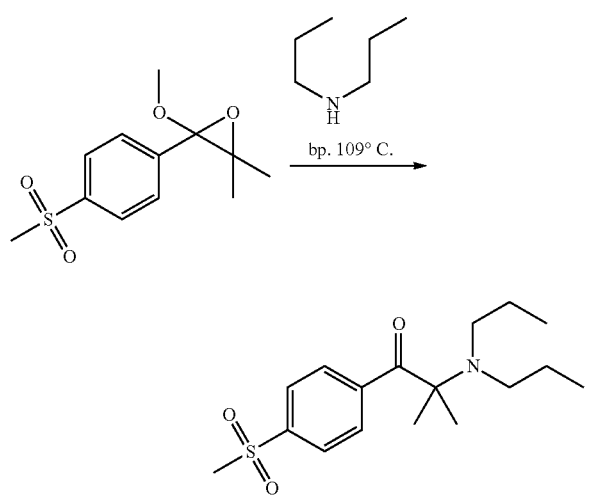

2-(Dipropylamino)-2-methyl-1-(4-methylsulfonylphenyl)propan-1-one: The title compound is prepared from 2-methoxy-3,3-dimethyl-2-(4-methylsulfonylphenyl)oxirane (intermediate for the preparation of compound 41) and dipropylamine (4 equivalents) according to the preparation of compound 21 (first ambient pressure, reflux, 44 hours and then pressure, 150° C., 24 hours). Yellow liquid;

$^1$H-NMR (300 MHz, CDCl$_3$), δ [ppm]: 0.79 (t, J=7.3 Hz, 6H), 1.34 (s, 6H), 1.42-1.55 (m, sextet-like, 4H), 2.41-2.47 (m, 4H), 3.10 (s, 3H), 7.97-7.80 (m, d-like, 2H), 8.70-8.73 (m, d-like, 2H);

MS (CI), m/z (%): found 327.2 (100; MH$_2^+$); calcd. for C$_{17}$H$_{27}$NO$_3$S: 325.

Compound 55

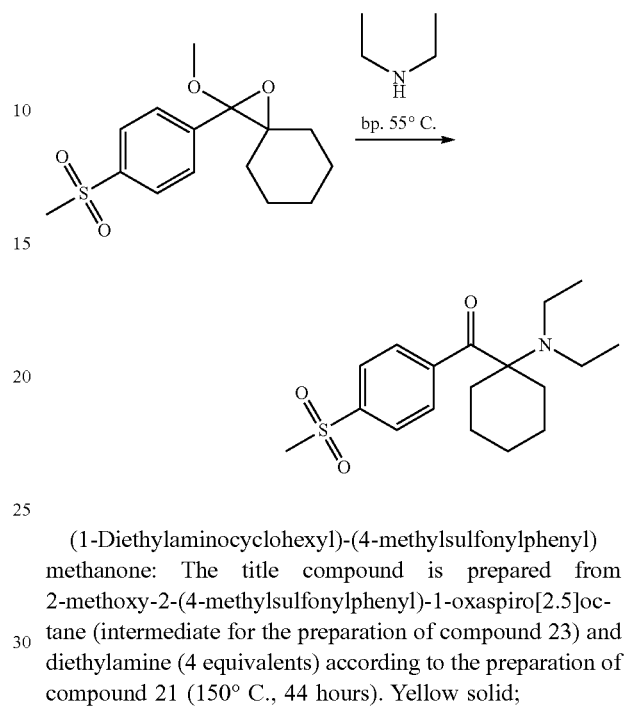

(1-Diethylaminocyclohexyl)-(4-methylsulfonylphenyl)methanone: The title compound is prepared from 2-methoxy-2-(4-methylsulfonylphenyl)-1-oxaspiro[2.5]octane (intermediate for the preparation of compound 23) and diethylamine (4 equivalents) according to the preparation of compound 21 (150° C., 44 hours). Yellow solid;

$^1$H-NMR (300 MHz, CDCl$_3$), δ [ppm]: 1.10 (t, J=7.1 Hz, 6H), ca. 1.13-1.29 (m, 3H), 1.49-1.67 (m, 5H), 2.20-2.24 (m, d-like, 2H), 2.72 (q, J=7.1 Hz, 4H), 3.1 (s, 3H), 7.95-7.98 (m, d-like, 2H), 8.53-8.56 (m, d-like, 2H);

MS (CI), m/z (%): found 338.18 (100; MH$^+$); calcd. for C$_{18}$H$_{27}$NO$_3$S: 337.

APPLICATION EXAMPLES

Solution Bleach

A solution of 213 μM Morin, 5 mM Peracetic acid and 20 μmol/l of the respective catalyst is prepared in 25 mmol/l carbonate buffer. The decay of the morin absorption is followed at 398 nm at 20° C. over time using a spectrophotometer. The time necessary to reach 50% of the initial morin absorption (t½) is given in the following table for each compound. Without the addition of catalyst (per acetic acid alone) t½ is 30 minutes. This value serves as the reference.

TABLE 1

| | α-Aminoketon | t ½ [Minuten] |
|---|---|---|
| Compound 1 | (structure) | 4.5 |

TABLE 1-continued

| α-Aminoketon | | t ½ [Minuten] |
|---|---|---|
| Compound 2 | (structure: 4-methylthiophenyl–C(=O)–C(CH₃)₂–N-morpholine) xHBF₄ | 6.5 |
| Compound 3 | (structure: 4-methylthiophenyl–C(=O)–C(CH₃)₂–N-morpholine) x HCl | 5.5 |
| Compound 4 | (structure: 4-butylthiophenyl–C(=O)–C(CH₃)₂–N-morpholine) | 5.3 |
| Compound 5 | (structure: 4-methylsulfinylphenyl–C(=O)–C(CH₃)₂–N-morpholine) | 3.5 |
| Compound 6 | (structure: 4-methylsulfonylphenyl–C(=O)–C(CH₃)₂–N-morpholine) | 3 |
| Compound 7 | (structure: phenyl–C(=O)–C(CH₃)₂–N-morpholine) | 8.1 |
| Compound 8 | (structure: HOOC–CH₂–S–(4-phenyl)–C(=O)–C(CH₃)₂–N-morpholine) xHCl | 8.3 |

Compound 1-8 prove to catalyze the per acetic acid oxidation of morin.

Stain Bleachin—1:

1.5 mM per acetic acid are added to 50 mM carbonate and phosphate buffer containing of different pH-values. 10 g bleached cotton and 0.8 g BC01 Tee (CFT) are washed with this buffer solution for 45 minutes at 30° C. Following the wash the textiles are rinsed with running tap water, spin dried and dried at 50° C. The lightness (Y) of the BC01 Tea fabric is measured before and after the wash, the difference of both Y values (ΔY) is a measure for the effectiveness of the bleach process. The higher the ΔY the more effective is the bleach. In a second experiment 200 μmol/l of compound 20 was added. The following table gives the ΔY values at different pH-values.

TABLE 2

|  | pH 6 | pH 7 | pH 7.9 | pH 8.3 | pH 9.5 | pH 9.9 | pH 10.3 |
|---|---|---|---|---|---|---|---|
| Per acetic acid | 8.2 | 9.6 | 11 | 10.8 | 9.8 | 8.1 | 7.1 |
| Compound 20 (diethylamino-methyl 4-methoxyphenyl ketone · xHCl) | 10 | 14 | 17.2 | 15.8 | 13.7 | 12.1 | 11.2 |

Compound 20 significantly boosts the per acetic acid bleach even at pH values >9.0.

Stain Bleaching—2:

1.5 mM per acetic acid are added to 50 mM carbonate and phosphate buffer containing of different pH-values. 10 g bleached cotton and 0.8 g BC01 Tee (CFT) are washed with this buffer solution for 45 minutes at 30° C. Following the wash the textiles are rinsed with running tap water, spin dried and dried at 50° C. The lightness (Y) of the BC03 Tea fabric is measured before and after the wash, the difference of both Y values (ΔY) is a measure for the effectiveness of the bleach process. The higher the ΔY the more effective is the bleach.

In the following experiments 25 µmol/l of different aminoketones are added. The following table gives the ΔY values at different pH-values.

TABLE 3

|  | pH 6 | pH 7 | pH 8.1 | pH 8.5 | pH 9 | pH 10 |
|---|---|---|---|---|---|---|
| Per acetic acid | 8.3 | 9.8 | 10.8 | 9.8 | 9.9 | 7.9 |
| + compound 1 | 9.4 | 13.1 | 14.7 | 12.6 | 12.3 | 9.6 |

TABLE 3-continued

|  | pH 6 | pH 7 | pH 8.1 | pH 8.5 | pH 9 | pH 10 |
|---|---|---|---|---|---|---|
| + compound 5 | 9.6 | 13 | 14.9 | 12.5 | 11.9 | 9.7 |
| + compound 6 | 9.6 | 13.1 | 15.4 | 13.1 | 12.7 | 10.1 |
| + compound 7 | 9.6 | 12.7 | 15.1 | 13 | 11.8 | 8.9 |

The α-aminoketones exhibit a clearly enhanced per acetic acid bleach performance.

Stain Bleaching—3:

20 g bleached cotton and 1.0 g BC01 tea (CFT) are washed in a wash liquor containing 5.6 g ECE98 standard detergent (ex WFK), 1.5 mmol/l per acetic acid, pH 9.8 for 45 minutes at 30° C. The lightness (Y) of the BC01 tea fabric is measured before and after the wash, the difference of both Y values (ΔY) is a measure for the effectiveness of the bleach process. The higher the ΔY the more effective is the bleach. In this example 12.5, 25, 50, 100 µmol/l of different aminoketones are added.

TABLE 4

ΔY α-aminoketone (BC01 Tee) at different concentrations

|  | 12.5 µM | 25 µM | 50 µM | 100 µM |
|---|---|---|---|---|
| Per Acetic Acid, no catalyst |  | 9.6 |  |  |
| Compound 20 |  |  | 11 | 13 |
| Compound 7 | 11.4 | 12.9 | 14.1 | 15.9 |
| Compound 2 | 10.4 | 11.3 | 12.3 | 15.6 |

TABLE 4-continued

| ΔY α-aminoketone (BC01 Tee) at different concentrations | | | | | |
|---|---|---|---|---|---|
| | | 12.5 μM | 25 μM | 50 μM | 100 μM |
| Compound 1 | | 10.8 | 11.9 | 13.5 | 15.4 |
| Compound 4 | | 10.4 | 10.6 | 11.6 | 13.4 |
| Compound 5 | | 12.1 | 13.4 | 15 | 17.3 |
| Compound 6 | | 11.8 | 13 | 14.8 | 16.4 |
| Compound 9 | | 12 | 12 | 14 | 16.1 |
| Compound 10 | | 11.9 | 13.5 | 15.3 | 17.6 |
| Compound 8 | xHCl | 11.1 | 12.3 | 13.9 | 15.6 |
| Compound 11 | | 10.1 | 10.7 | 11.6 | 12.6 |

TABLE 4-continued

ΔY α-aminoketone (BC01 Tee) at different concentrations

| | | 12.5 μM | 25 μM | 50 μM | 100 μM |
|---|---|---|---|---|---|
| Compound 12 | 4-(2-carboxyethyl)phenyl 2-methyl-2-morpholinopropan-1-one (HOOC-CH₂CH₂-C₆H₄-C(O)-C(CH₃)₂-morpholine) | 10.9 | 11.2 | 12.8 | 14.5 |

All α-Aminoketones used in this experiment clearly boost the bleach performance of per acetic acid.

Stain Bleaching—4:

20 g bleached cotton and 1.0 g BC01 tea (CFT) are washed in a wash liquor containing 5.6 g ECE98 standard detergent (ex WFK), 1.5 mmol/l per acetic acid, pH 9.8 for 45 minutes at 30° C. The lightness (Y) of the BC01 tea fabric is measured before and after the wash the difference of both Y values (ΔY) is a measure for the effectiveness of the bleach process. The results given in Table 5 are the difference of the ΔY of the peracetic acid plus catalyst and the ΔY of the peracetic acid alone (ΔΔY). Every value higher than zero indicates catalytic activity.

In this example 12.5, 25, 50, 100 μmol/l of different aminoketones are added.

TABLE 5

ΔΔY α-aminoketone (BC01 Tee) at different concentrations

| | | 12.5 μM | 25 μM | 50 μM | 100 μM |
|---|---|---|---|---|---|
| Comparative Experiment 1 | 1-(diethylamino)propan-2-one (CH₃-C(O)-CH₂-N(Et)₂) | 0 | 0.9 | 1.1 | 2.4 |
| Comparative Experiment 2 | 2-(diethylammonio)-1-phenylethan-1-one chloride (Ph-C(O)-CH₂-NH⁺(Et)₂ Cl⁻) | 0 | 1.4 | 2.3 | 3.7 |
| Compound 1 | 1-(4-(methylthio)phenyl)-2-methyl-2-morpholinopropan-1-one (MeS-C₆H₄-C(O)-C(CH₃)₂-morpholine) | 1.3 | 2.4 | 4.0 | 5.9 |
| Compound 5 | 1-(4-(methylsulfinyl)phenyl)-2-methyl-2-morpholinopropan-1-one (MeS(O)-C₆H₄-C(O)-C(CH₃)₂-morpholine) | 2.1 | 3.4 | 5.0 | 7.3 |
| Compound 6 | 1-(4-(methylsulfonyl)phenyl)-2-methyl-2-morpholinopropan-1-one (MeSO₂-C₆H₄-C(O)-C(CH₃)₂-morpholine) | 2.3 | 3.5 | 5.3 | 6.9 |

TABLE 5-continued
| ΔΔY α-aminoketone (BC01 Tee) at different concentrations | | 12.5 μM | 25 μM | 50 μM | 100 μM |
|---|---|---|---|---|---|
| Compound 13 | 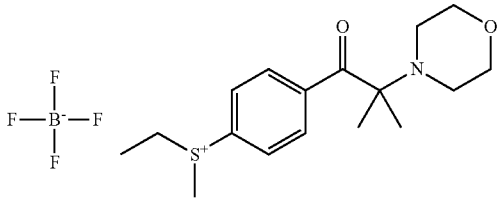 [SMILES: F[B-](F)(F)F ; CC[S+](C)c1ccc(C(=O)C(C)(C)N2CCOCC2)cc1] | 2.2 | 3.9 | 5.6 | 7.9 |
| Compound 14 | 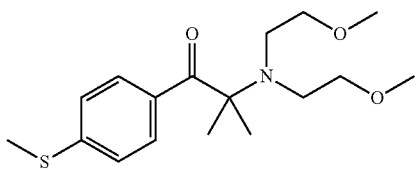 | 1.6 | 2.3 | 3.9 | 6.1 |
| Compound 15 | 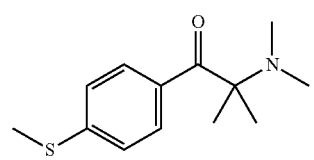 | 2.3 | 3.2 | 4.9 | 6.9 |
| Compound 16 | 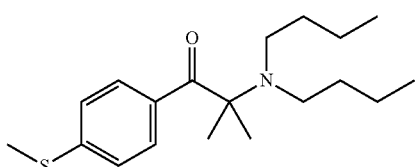 | 0.5 | 1.0 | 3.0 | 6.1 |
| Compound 17 | 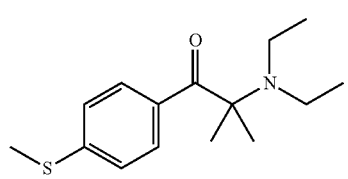 [SMILES: CCN(CC)C(C)(C)C(=O)c1ccc(SC)cc1] | 3.2 | 6.4 | 9.3 | 12.9 |
| Compound 18 | 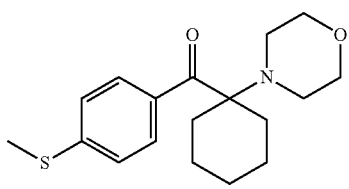 [SMILES: CSc1ccc(C(=O)C2(N3CCOCC3)CCCCC2)cc1] | 1.5 | 2.6 | 4.3 | 6.2 |
| Compound 19 | 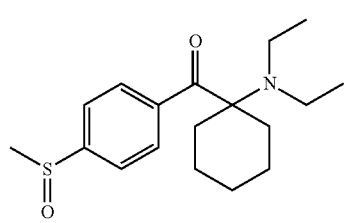 [SMILES: CCN(CC)C1(C(=O)c2ccc(S(C)=O)cc2)CCCCC1] | 1.7 | 2.5 | 4.5 | 6.9 |
| Compound 21 | 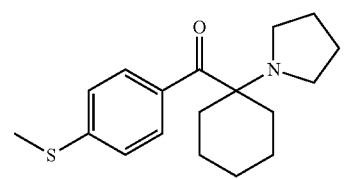 [SMILES: CSc1ccc(C(=O)C2(N3CCCC3)CCCCC2)cc1] | 2.2 | 3.9 | 6.0 | 8.5 |

TABLE 5-continued

| ΔΔY α-aminoketone (BC01 Tee) at different concentrations | | | | |
|---|---|---|---|---|
| | 12.5 μM | 25 μM | 50 μM | 100 μM |
| Compound 22 | 1.9 | 3.6 | 5.8 | 8.6 |
| Compound 23 | 2.8 | 4.4 | 7.5 | 10.1 |
| Compound 24 | 3.1 | 5.2 | 7.8 | 10.8 |
| Compound 25 | 1.0 | 2.4 | 3.1 | 5.0 |
| Compound 26 | 1.9 | 3.5 | 5.2 | 6.5 |
| Compound 27 | 2.5 | 3.5 | 5.8 | 7.8 |
| Compound 28 | 1.5 | 3.9 | 4.7 | 8.0 |

TABLE 5-continued

ΔΔY α-aminoketone (BC01 Tee) at different concentrations

| | | 12.5 μM | 25 μM | 50 μM | 100 μM |
|---|---|---|---|---|---|
| Compound 29 | | 1.9 | 3.5 | 6.3 | 8.7 |
| Compound 30 | | 1.8 | 2.8 | 6.4 | 8.7 |
| Compound 31 | | 2.3 | 4.8 | 7 | 10.9 |
| Compound 32 | | 1.2 | 3.3 | 6.8 | 11.1 |
| Compound 33 | | 2.8 | 5.5 | 8.7 | 12.9 |
| Compound 34 | | 1.2 | 1.6 | 3 | 6.1 |
| Compound 35 | | 1.1 | 2.6 | 3.3 | 7.3 |
| Compound 36 | | 5.8 | 9.2 | 13.2 | 17.5 |

TABLE 5-continued

ΔΔY α-aminoketone (BC01 Tee) at different concentrations

| | | 12.5 μM | 25 μM | 50 μM | 100 μM |
|---|---|---|---|---|---|
| Compound 37 | | 7.5 | 11.2 | 16.2 | 20.0 |
| Compound 40 | | 4.6 | 7.1 | 10.0 | 12.6 |
| Compound 41 | | 4.3 | 7.0 | 10.0 | 12.6 |
| Compound 42 | | 3.0 | 5.2 | 7.4 | 10.8 |
| Compound 43 | | 3.3 | 5.2 | 7.0 | 10.5 |
| Compound 44 | | 3.4 | 5.8 | 8.8 | 12.3 |
| Compound 45 | | 4.9 | 7.8 | 12.0 | 15.6 |

TABLE 5-continued

ΔΔY α-aminoketone (BC01 Tee) at different concentrations

| | 12.5 μM | 25 μM | 50 μM | 100 μM |
|---|---|---|---|---|
| Compound 46 | 4.9 | 8.4 | 11.9 | 16.1 |
| Compound 47 | 3.9 | 6.2 | 9.9 | 13.9 |
| Compound 48 | 5 | 7.7 | 11.6 | 15.3 |
| Compound 49 | 5.2 | 7.8 | 11.9 | 15.2 |
| Compound 50 | 3 | 5.3 | 8.1 | 13.1 |
| Compound 52 | 1.5 | 2.7 | 5.2 | 8.9 |
| Compound 54 | 3.2 | 6.5 | 9.8 | 14.3 |

TABLE 5-continued

ΔΔY α-aminoketone (BC01 Tee) at different concentrations

|  | 12.5 μM | 25 μM | 50 μM | 100 μM |
|---|---|---|---|---|
| Compound 55 | 0.8 | 1.4 | 2.9 | 5.3 |

All α-aminoketones used in this experiment clearly boost the bleach performance of per acetic acid.

Influence of Light

The same experiments as described above carried out without 1.5 mM peracetic acid do not result in a ΔΔY value different from zero. This indicates that light induced radical formation can not be responsible for the bleach effect.

A) Multistain Bleach Sodium Percarbonate/TAED 40 g bleach cotton fabric, BC01, tea, BC02 coffee, BC03 tea, and CS12 black currant stained cotton (0.4 g each) ex CFT are washed with a wash liquor containing: 4.7 g/l ECE98 standard detergent (WFK), 138 mg sodium per carbonate (SPC) and 30 mg Tetraacetylethylenediamine (TAED) for 60 minutes at 30° C. with and without 100 μmol/l of compound 1. The pH of the wash liquor is adjusted to pH 9.9 with 1M HCl. The lightness (Y) of the stained fabrics is measured before and after the wash, the difference of both Y values (ΔY) is a measure for the effectiveness of the bleach process. The higher the ΔY the more effective is the bleach.

TABLE 6

(ΔY) Values

|  | BC01 | BC02 | BC03 | CS12 |
|---|---|---|---|---|
| SPC/TAED | 9.0 | 7.1 | 7.8 | 51.8 |
| SPC/TAED + compound 1 | 15.5 | 14.1 | 11.3 | 55.9 |

The resulting ΔY values indicate a catalytic effect of compound 1 on all stains tested.

B) Multistain Bleach Sodium Percarbonate/TAED 40 g bleached cotton fabric, BC01, tea, BC02 coffee, BC03 tea, and CS12 black currant stained cotton (0.5 g each) ex CFT are washed with 250 ml wash liquor containing: 4.7 g/l ECE98 standard detergent (WFK), 165 mg sodium per carbonate (SPC) and 30 mg Tetraacetylethylenediamine (TAED) for 60 minutes at 30° C. with and without 80 μmol/l of catalyst. The pH of the wash liquor is adjusted to pH 10.1 with 1M HCl. The lightness (Y) of the stained fabrics is measured before and after the wash, the difference of both Y values (ΔY) is a measure for the effectiveness of the bleach process.

The results given in Table 7 are the difference of the ΔY of SPC+TAED plus catalyst and the ΔY of SPC+TAED alone (ΔΔY). Every value higher than zero indicates catalytic activity.

TABLE 7

(ΔΔY) Values

|  | BC01 | BC02 | BC03 | CS12 |
|---|---|---|---|---|
| SPC/TAED + | 3.0 | 3.9 | 2.8 | 2.7 |
| SPC/TAED + | 0.1 | 1.1 | 0.7 | 2.5 |

The resulting ΔΔY values indicate a catalytic effect of the catalysts tested

C) Multistain Bleach Sodium Percarbonate/DOBA 40 g bleached cotton fabric, BC01, tea, BC02 coffee, BC03 tea, and BC04 curry stained cotton (0.5 g each) ex CFT are washed with 250 ml wash liquor containing: 4.7 g/l ECE98 standard detergent (WFK), 165 mg sodium per carbonate (SPC) and 36 mg Dodecanoyloxybenzoic acid (DOBA) for 60 minutes at 30° C. with and without 80 μmol/l of catalyst. The pH of the wash liquor is adjusted to pH 10.1 with 1M HCl. The lightness (Y) of the stained fabrics is measured before and after the wash, the difference of both Y values (ΔY) is a measure for the effectiveness of the bleach process.

The results given in Table 8 are the difference of the ΔY of SPC+TAED plus catalyst and the ΔY of SPC+TAED alone (ΔΔY). Every value higher than zero indicates catalytic activity.

TABLE 8

| ΔΔY Values | BC01 | BC02 | BC03 | BC04 |
|---|---|---|---|---|
| SPC/DOBA + [structure] | 5.4 | 5.3 | 0.8 | 7.5 |

The resulting ΔΔY values indicate a catalytic effect of the catalyst tested

D) Multistain Bleach—Multiple Washes 10 g bleached cotton fabric, BC01 tea and BC02 coffee stained cotton (0.5 g each) ex CFT are washed in three subsequent washes with 250 ml wash liquor containing: 3 g/l ECE98 standard detergent (WFK), 42 mg sodium per carbonate (SPC) and 9 mg Dodecanoyloxybenzoic acid (DOBA) or Tetraacetylethylenediamine (TAED) for 20 minutes at 20° C. with and without 20 μmol/l of catalyst. The pH of the wash liquor is adjusted to pH 9.8 with 1M HCl. The lightness (Y) of the stained fabrics is measured before and after the wash, the difference of both Y values (ΔY) is a measure for the effectiveness of the bleach process.

The results given in Table 9 are the difference of the ΔY of SPC+DOBA or TAED plus catalyst and the ΔY of SPC+DOBA or TAED alone (ΔΔY). Every value higher than zero indicates catalytic activity.

TABLE 9

| ΔΔY Values | BC01 | BC02 |
|---|---|---|
| SPC/TAED + [structure] | 1.2 | 2.0 |
| SPC/DOBA + [structure] | 4.1 | 4.5 |

The resulting ΔΔY values after the 3$^{rd}$ wash indicate a catalytic effect of the catalyst tested with both bleach activators used E) Multistain Bleach Sodium Percarbonate/NOBS 40 g bleached cotton fabric, BC01, tea, BC02 coffee stained cotton (0.5 g each) ex CFT are washed with 250 ml wash liquor containing: 4.7 g/l ECE98 standard detergent (WFK), 165 mg sodium per carbonate (SPC) and 39 mg Nonyloxybenzolsulfonic acid (NOBS) for 60 minutes at 30° C. with and without 80 μmol/l of catalyst. The pH of the wash liquor is adjusted to pH 10.1 with 1M HCl. The lightness (Y) of the stained fabrics is measured before and after the wash, the difference of both Y values (ΔY) is a measure for the effectiveness of the bleach process.

The results given in Table 10 are the difference of the ΔY of SPC+TAED plus catalyst and the ΔY of SPC+TAED alone (ΔΔY). Every value higher than zero indicates catalytic activity.

TABLE 10

| ΔΔY Values | BC01 | BC02 |
|---|---|---|
| SPC/NOBS + [structure] | 3.2 | 2.7 |
| SPC/NOBS + [structure] | 1.4 | 0.5 |

The resulting ΔΔY values indicate a catalytic effect of the catalyst tested (100%).

F) Low Temperature Stain Bleaching:

20 g bleached cotton and 0.5 g BC01 tea (CFT) are washed in 100 ml 25 mM Carbonate buffer pH 9.6 containing 14 mg Tetraacetylethylenediamine (TAED) and 6.5 mM Hydrogen-peroxide (H$_2$O$_2$) and 100 μM Hydroxyethylenediphosphonate (HEDP) for 45 minutes at 10° C., with and without 30 μM of catalyst. The lightness (Y) of the BC01 tea fabric is measured before and after the wash the difference of both Y values (ΔY) is a measure for the effectiveness of the bleach process.

The results given in Table 11 are the difference of the ΔY of the TAED/H$_2$O$_2$ plus catalyst and the ΔY of the TAED/H$_2$O$_2$ alone (ΔΔY). Every value higher than zero indicates catalytic activity.

TABLE 11

| ΔΔY Values | BC01 |
|---|---|
| H$_2$O$_2$/TAED + Compound 1 [structure] | 5.7 |

TABLE 11-continued

ΔΔY Values

| | BC01 |
|---|---|
|  H₂O₂/TAED + Compound 5 | 6.9 |
| H₂O₂/TAED + Compound 6 | 7.5 |
| F—B⁻—F (BF₄⁻) H₂O₂/TAED + Compound 13 | 6.4 |

The resulting ΔΔY values indicate a catalytic effect of the catalyst tested.

The invention claimed is:

1. A process for the bleaching of stains or of soiling on textile materials or dishes in the context of a washing process or by the direct application of a stain remover comprising
   treating a textile material or dishes in an aqueous medium either by hand or in an automatic washing machine or dishwasher, at a pH between 7 and 11, together with a mixture comprising
   a) $H_2O_2$, a precursor of $H_2O_2$, or a peracid and
   b) a compound of formula (3)

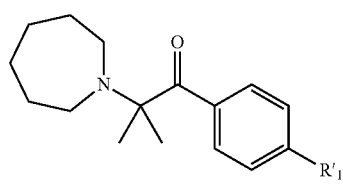

wherein
$R'_1$ is $SCH_3$, $S(O_2)CH_3$, H, $CH_3$, $S(O)CH_3$, $(CH_3)_2S^+$ $BF_4^-$ or $(CH_3)_2S^+(CH_3O)S(O_2)O^-$; or a compound of formula (4)

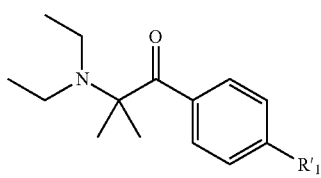

wherein
$R'_1$ is H, $CH_3$, $SCH_3$, $S(O)CH_3$, $S(O_2)CH_3$, $(CH_3)_2S^+$ $BF_4^-$ or $(CH_3)_2S^+(CH_3O)S(O_2)O^-$; or a compound of formula (5)

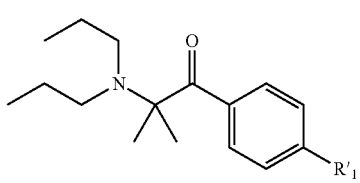

wherein
$R'_1$ is $SCH_3$, $S(O_2)CH_3$, H, $CH_3$, $S(O)CH_3$, $(CH_3)_2S^+$ $BF_4^-$ or $(CH_3)_2S^+(CH_3O)S(O_2)O^-$; or a compound of formula (6)

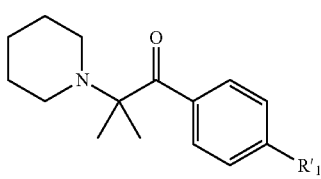

wherein
$R'_1$ = $SCH_3$, $S(O)CH_3$, $S(O_2)CH_3$, $(CH_3)_2S^+BF_4^-$ or $(CH_3)_2S^+(CH_3O)S(O_2)O^-$; or
a compound of formula (7)

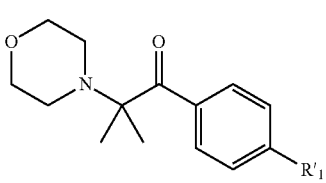

wherein
$R'_1$ =H, $S(O)CH_3$, $S(O_2)CH_3$, $(CH_3)(CH_3CH_2)S^+BF_4^-$, $(CH_3)_2S^+BF_4^-$, $(CH_3)_2S^+PF_6^-$ or $(CH_3)_2S^+(CH_3O)S(O_2)O^-$;

wherein the mixture is free of metal complexes, and wherein component a) is present in an amount of from 2 parts to 90 parts by weight and component b) is present in an amount of from 0.02 parts to 20 parts by weight; the sum being 100 parts.

2. The process according to claim 1 wherein component a) comprises a precursor of $H_2O_2$ and a bleach activator.

3. The process according to claim 1 wherein component b) is a compound of formula (3)

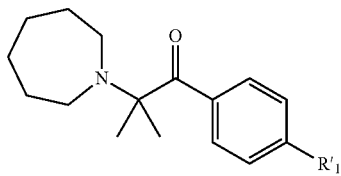

wherein
R'₁ is SCH₃, S(O₂)CH₃, H, CH₃, S(O)CH₃, (CH₃)₂S⁺BF₄⁻ or (CH₃)₂S⁺(CH₃O)S(O₂)O⁻.

4. The process according to claim 1 wherein component b is a compound of formula (4)

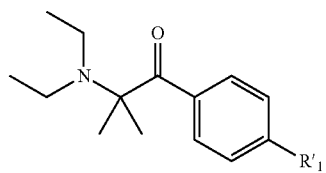

wherein
R'₁ is H, CH₃, SCH₃, S(O)CH₃, S(O₂)CH₃, (CH₃)₂S⁺BF₄⁻ or (CH₃)₂S⁺(CH₃O)S(O₂)O⁻.

5. The process according to claim 1 wherein component b is a compound of formula (5)

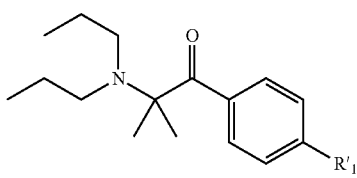

wherein
R'₁ is SCH₃, S(O₂)CH₃, H, CH₃, S(O)CH₃, (CH₃)₂S⁺BF₄⁻ or (CH₃)₂S⁺(CH₃O)S(O₂)O⁻.

6. The process according to claim 1 wherein component b is a compound of formula (6)

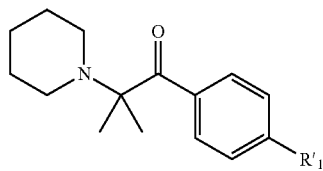

wherein
R'₁ =SCH₃, S(O)CH₃, S(O₂)CH₃, (CH₃)₂S⁺BF₄⁻ or (CH₃)₂S⁺(CH₃O)S(O₂)O⁻.

7. The process according to claim 1 wherein component b is a compound of formula (7)

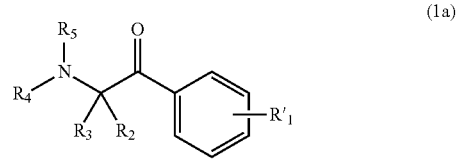
(1a)

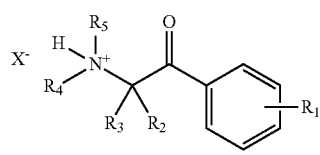
(2a)

wherein
R'₁ =H, S(O)CH₃, S(O₂)CH₃, (CH₃)(CH₃CH₂)S⁺BF₄⁻, (CH₃)₂S⁺BF₄⁻, (CH₃)₂S⁺PF₆⁻ or (CH₃)₂S⁺(CH₃O)S(O₂)O⁻.

\* \* \* \* \*